(12) United States Patent
Bhat et al.

(10) Patent No.: US 7,541,344 B2
(45) Date of Patent: Jun. 2, 2009

(54) MODULATION OF SURVIVIN EXPRESSION

(75) Inventors: Balkrishen Bhat, Carlsbad, CA (US); Bharvin Kumar Patel, Westfield, IN (US); Eric Swayze, Carlsbad, CA (US)

(73) Assignees: Eli Lilly and Company, Indianapolis, IN (US); ISIS Pharmaceuticals, Inc., Carlsbad, CA (US)

( * ) Notice: Subject to any disclaimer, the term of this patent is extended or adjusted under 35 U.S.C. 154(b) by 113 days.

(21) Appl. No.: 10/559,636

(22) PCT Filed: Jun. 3, 2004

(86) PCT No.: PCT/US2004/017490

§ 371 (c)(1), (2), (4) Date: Feb. 21, 2007

(87) PCT Pub. No.: WO2005/002507

PCT Pub. Date: Jan. 13, 2005

(65) Prior Publication Data

US 2007/0161547 A1 Jul. 12, 2007

Related U.S. Application Data

(60) Provisional application No. 60/475,324, filed on Jun. 3, 2003.

(51) Int. Cl.
A61K 31/70 (2006.01)
C07H 21/04 (2006.01)
C07H 21/02 (2006.01)
C12Q 1/68 (2006.01)
C12N 5/00 (2006.01)

(52) U.S. Cl. ............................. 514/44; 435/6; 435/375; 435/377; 536/23.1; 536/24.1; 536/24.5

(58) Field of Classification Search ........................ None
See application file for complete search history.

(56) References Cited

U.S. PATENT DOCUMENTS

| | | | |
|---|---|---|---|
| 3,687,808 | A | 8/1972 | Merigan et al. |
| 5,808,036 | A | 9/1998 | Kool |
| 5,898,031 | A | 4/1999 | Crooke |
| 6,060,456 | A * | 5/2000 | Arnold et al. ................. 514/44 |
| 6,077,709 | A * | 6/2000 | Bennett et al. ............... 435/375 |
| 6,107,094 | A | 8/2000 | Crooke |
| 6,165,788 | A | 12/2000 | Bennett et al. |
| 6,245,523 | B1 | 6/2001 | Altieri |
| 6,335,194 | B1 * | 1/2002 | Bennett et al. ............... 435/375 |
| 6,509,162 | B1 | 1/2003 | Altieri |
| 6,656,684 | B1 | 12/2003 | Sandler |
| 6,777,444 | B2 | 8/2004 | Huang et al. |
| 6,838,283 | B2 * | 1/2005 | Bennett et al. ............... 435/375 |
| 7,288,530 | B2 * | 10/2007 | Bennett et al. ................. 514/44 |
| 2002/0068708 | A1 | 6/2002 | Wengel et al. |
| 2002/0132788 | A1 | 9/2002 | Lewis et al. |
| 2002/0137708 | A1 | 9/2002 | Bennett et al. |
| 2002/0160393 | A1 | 10/2002 | Symonds et al. |
| 2003/0206887 | A1 * | 11/2003 | Morrissey et al. ........... 424/93.2 |
| 2003/0211607 | A1 | 11/2003 | Bennett et al. |
| 2004/0018999 | A1 | 1/2004 | Beach et al. |
| 2004/0259247 | A1 * | 12/2004 | Tuschl et al. ................. 435/375 |
| 2005/0100907 | A1 | 5/2005 | Kreutzer et al. |
| 2005/0143335 | A1 | 6/2005 | Bennett et al. |

FOREIGN PATENT DOCUMENTS

| | | |
|---|---|---|
| WO | WO 99/14226 | 3/1999 |
| WO | WO 99/32619 | 7/1999 |
| WO | WO 00/18781 | 4/2000 |
| WO | WO 00/44914 | 8/2000 |
| WO | WO 00/49035 | 8/2000 |
| WO | WO 01/29058 A1 | 4/2001 |
| WO | WO 01/36641 A2 | 5/2001 |
| WO | WO 01/36646 A1 | 5/2001 |
| WO | WO 01/48183 A2 | 7/2001 |
| WO | WO 01/57059 A1 | 8/2001 |
| WO | WO 01/75164 A2 | 10/2001 |
| WO | WO 02/44321 A2 | 6/2002 |

OTHER PUBLICATIONS

Vickers et al. The Journal of Biological Chemistry vol. 278(9):7108-7118, 2003.*
Adida et al., "Anti-apoptosis gene, surviving, and prognosis of neuroblastoma," *The Lancet*, Vo. 351, pp. 882-883 (1998).
Altieri, Dario, "Xa receptor EPR-1," *FASEB*, vol. 9, pp. 860-865 (1995).
Altieri, Dario, "Splicing of Effector Cell Protease Receptor-1 mRNA Is Modulated by an Unusual Retained Intron," *Biochemistry*, vol. 33, pp. 13848-13855 (1994).
Amarzguioui et al., "Tolerance for mutations and chemical modifications in a siRNA," *Nucleic Acids Research*, 31:2, pp. 589-595 (2003).
Ambrosini et al., "Induction of Apoptosis and Inhibition of Cell Proliferation by *surviving* Gene Targeting," *J. of Biological Chemistry*, 273:18, pp. 11177-11182 (1998).
Ambrosini et al., "A novel anti-apoptosis gene, *surviving*, expressed in cancer and lymphoma," *Nature Medicine*, 3:8, pp. 917-921 (1997).
Bass, Brenda, "Double-Stranded RNA as a Template for Gene Silencing," *Cell*, vol. 101, pp. 235-238 (2000).
Boutla et al., "Short 5'-phosphorylated double-stranded RNAs induce RNA interference in *Drosophila*," *Current Biology*, vol. 11, pp. 1776-1780 (2001).
Branch, Andrea, "A good antisense molecule is hard to find," *TIBS*, vol. 23, pp. 45-50 (1998).

(Continued)

Primary Examiner—Sean R McGarry
(74) Attorney, Agent, or Firm—Charles E. Cohen; Manisha A. Desai

(57) ABSTRACT

Compounds and compositions are provided for modulating the expression of survivin. The compounds, exemplified by those acting through an RNAi antisense mechanism of action, include double-stranded and single-stranded constructs, as well as siRNAs, canonical siRNAs, blunt-ended siRNAs and single-stranded antisense RNA compounds. Methods of using these compounds for modulation of survivin expression and for treatment of diseases associated with expression of survivin are provided.

24 Claims, No Drawings

OTHER PUBLICATIONS

Brantl, Sabine, "Antisense-RNA regulation and RNA interference," *Bioehimica et Biophysica Acta*, vol. 1575, pp. 15-25 (2002).

Caplen et al., "Specific inhibition of gene expression by small double-stranded RNAs in invertebrate and vertebrate systems," *PNAS*, 98:17, pp. 9742-9747 (2001).

Carmell et al., "The Argonaute family: tentacles that reach into RNAi, developmental control, stem maintenance, and tumorigenesis," *Genes & Development*, vol. 16, pp. 2733-2742 (2002).

Chui et al., "RNAi in Human Cells: Basic Structural and Functional Features of Small Interfering RNA," *Molecular Cell*, vol. 10, pp. 549-561 (2002).

Cogoni et al., "Post-transcriptional gene silencing across kingdoms," *Curr. Opinion in Genes Dev.*, vol. 10, pp. 638-643 (2000).

Cohen, Gerald, "Caspases: the executioners of apoptosis," *Biochem. J.*, vol. 326, pp. 1-16 (1997).

Czauderna et al., "Structural variations and stabilising modifications of synthetic siRNAs in mammalian cells," *Nucleic Acids Research*, 31:11, 2705-2716 (2003).

Elbashir et al., "Functional anatomy of siRNAs for mediating efficient RNAi in *Drosophila melanogaster* embryo lysate," *The EMBO Journal*, 20:23, pp. 6877-6888 (2001).

Elbashir et al., "RNA interference is mediated by 21- and 22-nucleotide RNAs," *Genes & Development*, vol. 15, pp. 188-200 (2001).

Elbashir, et al., "Duplexes of 21-nucleotide RNAs mediate RNA interference in cultured mammalian cells," *Nature*, vol. 411, pp. 494-498 (2001).

Fire et al., "Potent and specific genetic interference by double-stranded RNA in *Caenorhabditis elegans*," *Nature*, vol. 391, pp. 806-811 (1998).

Genbank Accession No. AW247335, Dec. 16, 1999.

Grossman et al., "Expression of the Apoptosis Inhibitor, Survivin, in Nonmelanoma Skin Cancer and Gene Targeting in a Keratinocyte Cell Line," *Laboratory Investigation*, United States and Canadian Academy of Pathology, 79:CX9, pp. 1121-1126 (1999).

Guo et al., "par-1, a Gene Required for Establishing Polarity in *C. elegans* Embryos, Encodes a Putative Ser/Thr Kinase That Is Asymmetrically Distributed," *Cell*, vol. 81, pp. 611-620 (1995).

Gura, Trisha, "A silence that speaks volumes," *Nature*, vol. 404, pp. 804-808 (2000).

Jen et al., "Suppression of Gene Expression by Targeted Disruption of Messange RNA: Available Options and Current Strategies," *Stem Cells*, vol. 18, pp. 307-319 (2000).

Kawasaki et al., "Uniformly Modified 2'-Deoxy-2'-fluoro Phosphorothioate Oligonucleotides as Nucleas-Resistant Antisense Compounds with High Affinity and Specificity for RNA Targets," *J. Med. Chem.*, vol. 36, pp. 831-841 (1993).

Kawasaki et al., "Synthesis and Biophysical Studies of 2'-dRibo-2'-F Modified Oligonucleotides," ISIS Pharmaceuticals, Inc., 2280 Faraday Avenue, Carlsbad, CA 92008, USA (1991).

Li et al., "Control of apoptosis and mitotic spindle checkpoint by surviving," *Nature*, vol. 396, pp. 580-584 (1998).

Li et al., "Pleiotropic cell-division defects and apoptosis induced by interference with surviving function," *Nature Cell Biology*, vol. 1, pp. 461-466 (1999).

Lu et al., "Expression of a Novel Antiapoptosis Gene, Survivin, Correlated with Tumor Cell Apoptosis and p53 Accumulation in Gastric Carcinomas," *Cancer Research*, vol. 58, pp. 1808-1812 (1998).

Martinez et al., "Single-Stranded Antisense siRNAs Guide Target RNA Cleavage in RNAi," *Cell*, vol. 110, pp. 563-574 (2002).

Metelev et al., "Study of Antisense Oligonucleotide Phosphorothioates Containing Segments of Oligodeoxynucleotides and 2'-O-Methyloligoribonucleotides," *Bioorganic & Medicinal Chemistry Letters*, 4:24, pp. 2929-2934 (1994).

Monia et al., "Evaluation of 2'-Modified Oligonucleotides Containing 2'-Deoxy Gaps as Antisense Inhibitors of Gene Expression," *J. of Biological Chemistry*, 268:19, pp. 14514-14522 (1993).

Montgomery et al., "RNA as a target of double-stranded RNA-mediated genetic interference in *Caenorhabditis elegans*," *Proc. Natl. Acad. Sci.*, vol. 95, pp. 15502-15507 (1998).

Paddison et al., "Stable suppression of gene expression by RNAi in mammalian cells," *PNAS*, 99:3, pp. 1443-1448 (2002).

Parrish et al., "Functional Anatomy of a dsRNA Trigger: Differential Requirement for the Two Trigger Strands in RNA Interference," *Molecular Cell*, vol. 6, pp. 1077-1087 (2000).

Schwarz et al., "Evidence that siRNAs Function as Guides, Not Primers, in the *Drosophila* and Human RNAi Pathways," *Molecular Cell*, vol. 10, pp. 537-538 (2002).

Sijen et al., "On the Role of RNA Amplification in dsRNA-Triggered Gene Silencing," *Cell*, vol. 107, pp. 465-476 (2001).

Sui et al., "A DNA vector-based RNAi technology to suppress gene expression in mammalian cells," *PNAS*, 99:8, pp. 5515-5520 (2002).

Yu et al., "RNA interference by expression of short-interfering RNAs and hairpin RNAs in mammalian cells," *PNAS*, 99:9, pp. 6047-6052 (2002).

Zhou et al., "Post-transcriptional suppression of gene expression in *Xenopus* embryos by small interfering RNA," *Nucleic Acids Research*, 30:7, pp. 1664-1669 (2002).

\* cited by examiner

MODULATION OF SURVIVIN EXPRESSION

This application is a United States national phase entry, pursuant to 35 U.S.C. 371, of PCT/US2004/017490, filed Jun. 3, 2004, which claims the benefit of U.S. patent application Ser. No. 60/475,324 (filed Jun. 3, 2003), Ser. No. 10/618, 553 (filed Jul. 11, 2003) and Ser. No. 10/823,448 (filed Apr. 13, 2004), each of which is herein incorporated by reference.

Information disclosed and/or claimed in this patent application has been generated pursuant to a joint research agreement among Eli Lilly and Company and Isis Pharmaceuticals, Inc.

FIELD OF THE INVENTION

The present invention provides compositions and methods for modulating the expression of survivin. In particular, this invention relates to antisense compounds, particularly double-stranded oligonucleotides, specifically hybridizable with nucleic acids encoding human survivin. Such oligonucleotides have been shown to modulate the expression of survivin.

BACKGROUND OF THE INVENTION

A hallmark feature of cancerous cells is uncontrolled proliferation. Among the differences that have been discovered between tumor and normal cells is resistance to the process of programmed cell death, also known as apoptosis (Ambrosini et al., *Nat. Med.*, 1997, 3, 917-921). Apoptosis is a process multicellular organisms have evolved to prevent uncontrolled cell proliferation as well as to eliminate cells that have become sick, deleterious, or are no longer necessary. The process of apoptosis involves a multistep cascade in which cells are degraded from within through the concerted action of proteolytic enzymes and DNA endonucleases, resulting in the formation of apoptotic bodies that are then removed by scavenger cells. Research to date has shown that much of the intracellular degradation is carried out through the action of the caspases, a family of proteolytic enzymes that cleave adjacent to aspartate residues (Cohen, *Biochemistry Journal*, 1997, 326, 1-16).

The finding that most tumor cells display resistance to the apoptotic process has led to the view that therapeutic strategies aimed at attenuating the resistance of tumor cells to apoptosis could represent a novel means to halt the spread of neoplastic cells (Ambrosini et al., *Nat. Med.*, 1997, 3, 917-921). One of the mechanisms through which tumor cells are believed to acquire resistance to apoptosis is by overexpression of survivin, a recently described member of the IAP (inhibitor of apoptosis) caspase inhibitor family. To date, overexpression of survivin has been detected in tumors of the lung, colon, pancreas, prostate, breast, stomach, non-Hodgkin's lymphoma, and neuroblastoma (Adida et al., *Lancet*, 1998, 351, 882-883; Ambrosini et al., *Nat. Med.*, 1997, 3, 917-921; Lu et al., *Cancer Res.*, 1998, 58, 1808-1812). A more detailed analysis has been performed in neuroblastoma where it was found that survivin overexpression segregated with tumor histologies known to associate with poor prognosis (Adida et al., *Lancet*, 1998, 351, 882-883). Finally, Ambrosini et al. describe transfection of HeLa cells with an expression vector containing a 708 nt fragment of the human cDNA encoding effector cell protease receptor 1 (EPR-1), the coding sequence of which is complementary to the coding strand of survivin (Ambrosini et al., *J. Bio. Chem.*, 1998, 273, 11177-11182). This construct caused a reduction in cell viability.

Survivin has recently been found to play a role in cell cycle regulation. It has been found to be expressed in the G2/M phase of the cell cycle in a cycle-regulated manner, and associates with microtubules of the mitotic spindle. Disruption of this interaction results in loss of survivin's anti-apoptotic function and increased caspase-3 activity during mitosis. Caspase-3 is associated with apoptotic cell death. It is therefore believed that survivin may counteract a default induction of apoptosis in G2/M phase. It is believed that the overexpression of survivin in cancer may overcome this apoptotic checkpoint, allowing undesired survival and division of cancerous cells. The survivin antisense construct described by Ambrosini above was found to downregulate endogenous survivin in HeLa cells and to increase caspase-3-dependent apoptosis in cells in G2/M phase. Li et al., *Nature*, 1998, 396, 580-584.

In many species, introduction of double-stranded RNA (dsRNA) induces potent and specific gene silencing. This phenomenon occurs in both plants and animals and has roles in viral defense and transposon silencing mechanisms. (Jorgensen et al., Plant Mol. Biol., 1996, 31, 957-973; Napoli et al., Plant Cell, 1990, 2, 279-289).

The first evidence that dsRNA could lead to gene silencing in animals came from work in the nematode, *Caenorhabditis elegans*, where it has been shown that feeding, soaking or injecting dsRNA (a mixture of both sense and antisense strands) results in much more efficient silencing than injection of either the sense or the antisense strands alone (Guo and Kemphues, Cell, 1995, 81, 611-620; Fire et al., *Nature* 391: 806-811 (1998); Montgomery et al., Proc. Natl. Acad. Sci. USA 95:15502-15507 (1998); PCT International Publication WO99/32619; (Fire et al., Nature, 1998, 391, 806-810; Timmons et al., Gene, 2001, 263, 103-112; Timmons and Fire, Nature, 1998, 395, 854). Since, the phenonmenon has been demonstrated in a number of organisms, including *Drosophila melanogaster* (Kennerdell et al., Cell 95:1017-1026 (1998)); and embryonic mice (Wianny et al, *Nat. Cell Biol.* 2:70-75 (2000)).

This posttranscriptional gene silencing phenomenon has been termed "RNA interference" (RNAi) and has come to generally refer to the process of gene silencing involving dsRNA which leads to the sequence-specific reduction of gene expression via target mRNA degradation (Tuschl et al., Genes Dev., 1999, 13, 3191-3197).

It has been demonstrated that 21- and 22-nt dsRNA fragments having 3' overhangs are the canonical sequence-specific mediators of RNAi. These fragments, which are termed short interfering RNAs (siRNAs), are generated by an RNase III-like processing reaction from longer dsRNA. Chemically synthesized siRNA also mediate efficient target RNA cleavage with the site of cleavage located near the center of the region spanned by the guiding strand of the siRNA. (Elbashir et al., Nature, 2001, 411, 494-498). Characterization of the suppression of expression of endogenous and heterologous genes caused by the 21-23 nucleotide siRNAs has been investigated in several mammalian cell lines, including human embryonic kidney (293) and HeLa cells (Elbashir et al., Genes and Development, 2001, 15, 188-200).

Recently, it has been shown that single-stranded RNA oligomers (ssRNAi or asRNA) of antisense polarity can be potent inducers of gene silencing and that single-stranded oligomers are ultimately responsible for the RNAi phenomenon (Tijsterman et al., Science, 2002, 295, 694-697).

U.S. Pat. Nos. 5,898,031 and 6,107,094, each of which is herein incorporated by reference, describe certain oligonucleotides having RNA-like properties. When hybridized with RNA, these oligonucleotides serve as substrates for a dsRNase enzyme with resultant cleavage of the RNA by the enzyme (Crooke, 2000; Crooke, 1999).

As a result of these advances in the understanding of apoptosis and the role that survivin expression is believed to play in conferring a growth advantage to a wide variety of tumor cell types, there is a great desire to provide compositions of matter which can modulate the expression of survivin. It is greatly desired to provide methods of diagnosis and detection of nucleic acids encoding survivin in animals. It is also desired to provide methods of diagnosis and treatment of conditions arising from survivin expression. In addition, improved research kits and reagents for detection and study of nucleic acids encoding survivin are desired. Thus, the present invention provides a class of novel inhibitors of survivin, compositions comprising these compounds, and methods of using the compounds.

SUMMARY OF THE INVENTION

The present invention is directed to oligomeric compounds, particularly single and double-stranded antisense compounds, which are targeted to a nucleic acid encoding survivin, and which modulate the expression of survivin. In some embodiments the antisense compounds are oligonucleotides. In some embodiments, the oligonucleotides are RNAi oligonucleotides (which are predominantly RNA or RNA-like). In other embodiments, the oligonucleotides are RNase H oligonucleotides (which are predominantly DNA or DNA-like). In still other embodiments, the oligonucleotides may be chemically modified. Pharmaceutical and other compositions comprising the antisense compounds of the invention are also provided. Further provided are methods of modulating the expression of survivin in cells or tissues comprising contacting said cells or tissues with one or more of the antisense compounds or compositions of the invention. Further provided are methods of treating an animal, particularly a human, suspected of having or being prone to a disease or condition associated with expression of survivin by administering a therapeutically or prophylactically effective amount of one or more of the oligonucleotides or compositions of the invention. In another embodiment, the present invention provides for the use of a compound of the invention in the manufacture of a medicament for the treatment of any and all conditions disclosed herein.

The disease or condition can be a hyperproliferative condition. In one embodiment, the hyperproliferative condition is cancer.

The oligomeric compounds of the present invention are inhibitors of survivin expression or overexpression. Because these compounds inhibit the effects of survivin expression or overexpression, the compounds are useful in the treatment of disorders related to survivin activity. Thus, the compounds of the present invention are antineoplastic agents.

The present compounds are believed to be useful in treating carcinomas such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic syndromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors.

Thus, in one embodiment, the present invention provides a method for the treatment of susceptible neoplasms comprising: administering to an animal, particularly a human, an effective amount of a single-stranded (ssRNA or ssRNAi or asRNA) or double-stranded (dsRNA or siRNA) oligonucleotide directed to survivin. The ssRNA or dsRNA oligonucleotide may be modified or unmodified. That is, the present invention provides for the use of a double-stranded RNA oligonucleotide targeted to survivin, or a pharmaceutical composition thereof, for the treatment of susceptible neoplasms.

In another aspect, the present invention provides for the use of a compound of an isolated double-stranded RNA oligonucleotide in the manufacture of a medicament for inhibiting survivin expression or overexpression. Thus, the present invention provides for the use of an isolated double-stranded RNA oligonucleotide targeted to survivin in the manufacture of a medicament for the treatment of susceptible neoplasms by means of the method described above.

The compounds of the present invention are especially useful for the treatment of pancreatic cancer, prostate cancer, colon cancer, breast cancer, lung cancer, bladder cancer, liver cancer, ovarian cancer, renal cancer, glioblastoma, and non-Hodgkins lymphoma.

Another embodiment of the present invention is a method of treating an animal, particularly a human, having a disease or condition characterized by a reduction in apoptosis comprising administering to the patient a therapeutically effective amount an of antisense compound 8 to 80 nucleobases in length targeted to a nucleic acid molecule encoding human survivin so that expression of survivin is inhibited.

The present invention also provides a method of modulating apoptosis in a cell comprising contacting a cell with an antisense compound 8 to 80 nucleobases in length targeted to a nucleic acid molecule encoding human survivin so that apoptosis is modulated.

Still another embodiment of the invention is a method of modulating cytokinesis in a cell comprising contacting a cell with an antisense compound 8 to 80 nucleobases in length targeted to a nucleic acid molecule encoding human survivin so that cytokinesis is modulated.

The present invention also provides a method of modulating the cell cycle in a cell comprising contacting a cell with an antisense compound 8 to 80 nucleobases in length targeted to a nucleic acid molecule encoding human survivin so that the cell cycle is modulated.

In still another embodiment of the invention, there is provided a method of inhibiting the proliferation of cells comprising contacting cells with an effective amount of an antisense compound 8 to 80 nucleobases in length targeted to a nucleic acid molecule encoding human survivin, so that proliferation of the cells is inhibited. In one embodiment, the cells are cancer cells. The method may further comprise administering to the patient a chemotherapeutic agent.

In yet another embodiment, there is provided a method of modulating apoptosis of hyperproliferative cells comprising contacting the cells with an effective amount of an antisense compound 8 to 80 nucleobases in length targeted to a nucleic acid molecule encoding human survivin, so that apoptosis of cells is modulated. In one embodiment, the cells are hyperproliferative cells and apoptosis is enhanced by the antisense compound. In another embodiment, the modulation of apoptosis is sensitization to an apoptotic stimulus. In one embodiment, the apoptotic stimulus is a cytotoxic chemotherapeutic agent. The method may further comprise contacting the cells with a chemotherapeutic agent.

DETAILED DESCRIPTION OF THE INVENTION

The present invention employs double and single-stranded oligomeric antisense compounds, particularly single or double-stranded oligonucleotides which are RNA or RNA-like and single-stranded oligonucleotides which are DNA or DNA-like for use in modulating the function of nucleic acid molecules encoding survivin, ultimately modulating the amount of survivin produced. This is accomplished by providing antisense compounds which specifically hybridize with one or more nucleic acids encoding survivin. As used herein, the terms "target nucleic acid" and "nucleic acid encoding survivin" encompass DNA encoding survivin, RNA (including pre-mRNA and mRNA or portions thereof) transcribed from such DNA, and also cDNA derived from such RNA. The specific hybridization of an oligomeric compound with its complementary sense-orientation target nucleic acid interferes with the normal function of the nucleic acid. This modulation of function of a target nucleic acid by compounds which specifically hybridize to it is generally referred to as "antisense," and such compounds can be described as being in the "antisense orientation" relative to the target.

The functions of DNA to be interfered with include replication and transcription. The functions of RNA to be interfered with include, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of survivin at the RNA and/or the protein level. In the context of the present invention, "modulation" means either an increase (stimulation) or a decrease (inhibition) in the expression. In the context of the present invention, inhibition is a desired form of modulation of gene expression and RNA, and in some embodiments mRNA, is a suitable target.

It is suitable to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding survivin. The targeting process also includes determination of a site or sites within this gene for the antisense interaction to occur such that the desired effect, e.g., detection or modulation of expression of the mRNA and or protein, will result. Within the context of the present invention, one intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG and 5'-CUG, while the translation initiation codons 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding survivin, regardless of the sequence(s) of such codons.

It is also known in the art that a translation termination codon (or "step codon") of a gene may have one of three sequences, i.e., 5'-UAA, 5'-UAG or 5'-UGA (the corresponding DNA sequences are 5'-TAA, 5'-TAG and 5'-TOA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be an effective target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions, and are particularly useful in situations where aberrant splicing is implicated in disease, or where an overproduction of a particular mRNA splice product is implicated in disease.

Once one or more target sites have been identified, antisense oligomeric compounds, typically an antisense oligonucleotide, are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a complete or partial loss of function, and there is a sufficient degree of complementarity to avoid non-specific binding of the antisense compound to non-target sequences under conditions in which specific binding is desired, i.e., under physiological conditions in the case of therapeutic treatment, or under conditions in which in vitro or in vivo assays are performed. Moreover, an oligonucleotide may hybridize over one or more segments such that intervening or adjacent segments are not involved in the hybridization event (e.g., a loop structure, mismatch or hairpin structure). The compounds of the present invention comprise at least 70%, at least 75%, at least 80%, at least 85%, at least 90%, at least 95%, at least 99%, or 100% sequence complementarity to a target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, homology, sequence identity or complementarity, between the antisense compound and target is between about 50% to about 60%. In some embodiments, homology, sequence identity or complementarity, is between about 60% to about 70%. In some embodiments, homology, sequence identity or complementarity, is between about 70% and about 80%. In some embodiments, homology, sequence identity or complementarity, is between about 80% and about 90%. In some embodiments, homology, sequence identity or complementarity, is about 90%, about 92%, about 94%, about 95%, about 96%, about 97%, about 98%, about 99% or about 100%.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

Multiple mechanisms exist by which short synthetic oligonucleotides can be used to modulate gene expression in mammalian cells. A commonly exploited antisense mechanism is RNase H-dependent degradation of the targeted RNA. RNase H is a ubiquitously expressed endonuclease that recognizes antisense DNA-RNA heteroduplex, hydrolyzing the RNA strand. A further antisense mechanism involves the utilization of enzymes that catalyze the cleavage of RNA-RNA duplexes. These reactions are catalyzed by a class of RNAse enzymes including but not limited to RNAse III and RNAse L. The antisense mechanism known RNA interference (RNAi) is operative on RNA-RNA hybrids and the like. Both RNase H-based antisense (usually using single-stranded compounds) and RNA interference (usually using double-stranded compounds known as siRNAs) are antisense mechanisms, typically resulting in loss of target RNA function.

Optimized siRNA and RNase H-dependent oligomeric compounds behave similarly in terms of potency, maximal effects, specificity and duration of action, and efficiency. Moreover it has been shown that in general, activity of dsRNA constructs correlated with the activity of RNase H-dependent single-stranded antisense compounds targeted to the same site. One major exception is that RNase H-dependent antisense compounds were generally active against target sites in pre-mRNA whereas siRNAs were not.

These data suggest that, in general, sites on the target RNA that were not active with RNase H-dependent oligonucleotides were similarly not good sites for siRNA. Conversely, a significant degree of correlation between active RNase H oligonucleotides and siRNA was found, suggesting that if a site is available for hybridization to an RNase H oligonucleotide, then it is also available for hybridization and cleavage by the siRNA complex. Consequently, once suitable target sites have been determined by either antisense approach, these sites can be used to design constructs that operate by the alternative antisense mechanism (Vickers et al., 2003, *J. Biol. Chem.* 278, 7108). Moreover, once a site has been demonstrated as active for either an RNAi or an RNAse H oligonucleotide, a single-stranded RNAi oligonucleotide (ssRNAi or asRNA) can be designed.

In some embodiments of the present invention, double-stranded antisense oligonucleotides are suitable. These double-stranded antisense oligonucleotides may be RNA or RNA-like, and may be modified or unmodified, in that the oligonucleotide, if modified, retains the properties of forming an RNA:RNA hybrid and recruitment and (activation) of a dsRNase. In other embodiments, the single-stranded oligonucleotides (ssRNAi or asRNA) may be RNA-like.

In other embodiments of the present invention, single-stranded antisense oligonucleotides are suitable. In some embodiments, the single-stranded oligonucleotides may be "DNA-like", in that the oligonucleotide has well characterized structural features, for example a plurality of unmodified 2' Hs or a stabilized backbone such as e.g., phosphorothioate, that is structurally suited for interaction with a target oligonucleotide and recruitment and (activation) of RNase H.

While oligonucleotides are one form of antisense compound, the present invention comprehends other oligomeric antisense compounds, including but not limited to oligonucleotide mimetics such as are described below. The compounds in accordance with this invention can comprise from about 8 to about 80 nucleobases. In another embodiment, the oligonucleotide is about 10 to 50 nucleotides in length. In yet another embodiment, the oligonucleotide is 12 to 30 nucleotides in length. In yet another embodiment, the oligonucleotide is 12 to 24 nucleotides in length. In yet another embodiment, the oligonucleotide is 19 to 23 nucleotides in length. Some embodiments comprise at least an 8-nucleobase portion of a sequence of an oligomeric compound which inhibits expression of survivin. dsRNA or siRNA molecules directed to survivin, and their use in inhibiting survivin mRNA expression, are also embodiments within the scope of the present invention.

The oligonucleotides of the present invention also include variants in which a different base is present at one or more of the nucleotide positions in the oligonucleotide. For example, if the first nucleotide is an adenosine, variants may be produced which contain thymidine (or uridine if RNA), guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of survivin mRNA.

Oligomeric Compounds

In the context of the present invention, the term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular and may also include branching. Oligomeric compounds can include double-stranded constructs such as, for example, two strands hybridized to form double-stranded compounds or a single strand with sufficient self complementarity to allow for hybridization and formation of a fully or partially double-stranded compound. In one embodiment of the invention, double-stranded antisense compounds encompass short interfering RNAs (siRNAs). As used herein, the term "siRNA" is defined as a double-stranded compound having a first and second strand and comprises a central complementary portion between said first and second strands and terminal portions that are optionally complementary between said first and second strands or with the target mRNA. Each strand may be from about 8 to about 80 nucleobases in length, 10 to 50 nucleobases in length, 12 to 30 nucleobases in length, 12 to 24 nucleobases in length or 19 to 23 nucleobases in length. The central complementary portion may be from about 8 to about 80 nucleobases in length, 10 to 50 nucleobases in length, 12 to 30 nucleobases in length, 12 to 24 nucleobases in length or 19 to 23 nucleobases in length. The terminal portions can be from 1 to 6 nucleobases in length. The siRNAs may also have no terminal portions. The two strands of an siRNA can be linked internally leaving free 3' or 5' termini or can be linked to form a continuous hairpin structure or loop. The hairpin structure may contain an overhang on either the 5' or 3' terminus producing an extension of single-stranded character.

In one embodiment of the invention, double-stranded antisense compounds are canonical siRNAs. As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

In another embodiment, the double-stranded antisense compounds are blunt-ended siRNAs. As used herein the term "blunt-ended siRNA" is defined as an siRNA having no terminal overhangs. That is, at least one end of the double-stranded compound is blunt. siRNAs whether canonical or blunt act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double-stranded. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

In general an oligomeric compound comprises a backbone of momeric subunits joined linking groups where each linked momeric subunit is directly or indirectly attached to a heterocyclic base moiety. Oligomeric compounds may also include monomeric subunits that are not linked to a heterocyclic base moiety thereby providing abasic sites. Any one of the repeated units making up an oligomeric compound can be modified giving rise to a variety of motifs including hemimers, gapmers and chimeras.

As is known in the art, a nucleoside comprises a sugar moiety attached to a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar giving the more common 3', 5-internucleoside linkage or the not so common 2',5'-internucleoside linkage. In forming oligonucleotides, the phosphate groups covalently link the sugar moieties of adjacent nucleosides. The respective ends can be joined to form a circular structure by hybridization or by formation of a covalent bond. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring form the backbone of the oligonucleotide. The normal internucleoside linkage that comprises the backbone of RNA and DNA is a 3' to 5' phosphodiester linkage. However, open linear structures are generally desired.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside linkages, as well as oligonucleotide analogs or chemically modified oligonucleotides that have one or more non-naturally occurring portions which function in a similar manner. Such modified or substituted oligonucleotides are suitable over the naturally occurring forms because of desirable properties such as, for example, enhanced cellular uptake, enhanced affinity for a nucleic acid target and enhanced nuclease stability.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic linkers and one or more short chain heterocyclic linkers. These internucleoside linkages include but are not limited to siloxane, sulfide, sulfoxide, sulfone, acetyl, formacetyl, thioformacetyl, methylene formacetyl, thioformacetyl, alken, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Further included in the present invention are antisense oligomeric compounds including antisense oligonucleotides, external guide sequence (EGS) oligonucleotides, alternate splicers, and other oligomeric compounds which hybridize to at least a portion of the target nucleic acid. As such, these antisense oligomeric compounds may be introduced in the form of single-stranded, double-stranded, circular or hairpin oligomeric compounds and may contain structural elements such as internal or terminal bulges, mismatches or loops. In general, nucleic acids (including oligonucleotides) may be described as "DNA-like" (i.e., having 2'-deoxy sugars and, generally, T rather than U bases) or "RNA-like" (i.e., having 2'-hydroxyl or 2'-modified sugars and, generally U rather than T bases). Once introduced to a system, the oligomeric compounds of the invention may elicit the action of one or more enzymes or structural proteins to effect modification of the target nucleic acid.

The oligomeric compounds in accordance with this invention can comprise from about 8 to about 80 nucleobases (i.e. from about 8 to about 80 linked nucleobases and/or monomeric subunits). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the oligomeric compounds of the invention are 10 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, or 30 nucleobases in length.

In a further embodiment, the oligomeric compounds of the invention are 12 to 24 nucleobases in length. One having ordinary skill in the art will appreciate that this embodies oligomeric compounds of 12, 13, 14, 15, 16, 17, 18, 19, 20, 21, 22, 23 or 24 nucleobases in length.

In another embodiment, the oligomeric compounds of the invention are 19 to 23 nucleobases in length. One having ordinary skill in the art will appreciate that this embodies oligomeric compounds of 19, 20, 21, 22 or 23 nucleobases in length.

One particularly length for oligomeric compounds is from about 12 to about 30 nucleobases. Another particularly length is from about 12 to about 24 nucleobases. A further particularly suitable length is from about 19 to about 23 nucleobases.

Chimeric Oligomeric Compounds

It is not necessary for all positions in a oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds containing two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, alteration of charge, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art. Similar observations are made for chimeras that form RNA:RNA hybrids and are substrates for dsRNases.

Chimeric oligomeric compounds of the invention may be formed as composite structures of two or more oligonucleotides, oligonucleotide analogs, oligonucleosides and/or oligonucleotide mimetics as described above. Routinely used chimeric compounds include but are not limited to hybrids, hemimers, gapmers, inverted gapmers and blockmers wherein the various point modifications and or regions are selected from native or modified DNA and RNA type units and or mimetic type subunits such as for example locked nucleic acids (LNA) (which encompasses ENA™ as described below), peptide nucleic acids (PNA), morpholinos, and others. These are described below. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Oligomer Mimetics

Another group of oligomeric compounds amenable to the present invention includes oligonucleotide mimetics. The term mimetic as it is applied to oligonucleotides is intended to include oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA). PNAs have favorable hybridization properties, high biological stability and are electrostatically neutral molecules. In one recent study PNAs were used to correct aberrant splicing in a transgenic mouse model (Sazani et al., *Nat. Biotechnol.*, 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—CH$_2$— as shown below) to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. PNAs can be obtained commercially from Applied Biosystems (Foster City, Calif., USA).

Numerous modifications have been made to the basic PNA backbone since it was introduced in 1991 by Nielsen and coworkers (Nielsen et al., *Science*, 1991, 254, 1497-1500).

The basic structure is shown below:

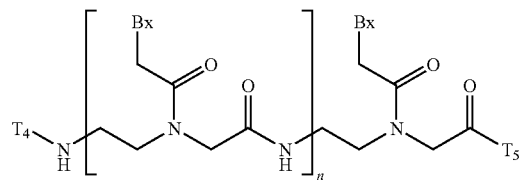

wherein

Bx is a heterocyclic base moiety;

$T_4$ is hydrogen, an amino protecting group, —C(O)R$_5$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N(Z$_1$)Z$_2$, R$_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, C$_1$-C$_6$ alkyl, or an amino protecting group;

$Z_2$ is hydrogen, C$_1$-C$_6$ alkyl, an amino protecting group, —C(=O)—(CH$_2$)$_n$-J-Z$_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —C$_1$-C$_6$ alkyl, —C(=O)—CH$_3$, benzyl, benzoyl, or —(CH$_2$)$_n$—N(H)Z$_1$;

each J is O, S or NH;

R$_5$ is a carbonyl protecting group; and n is from 7 to about 79.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds have been studied in zebrafish embryos (see: *Genesis*, volume 30, issue 3, 2001 and Heasman, J., *Dev. Biol.*, 2002, 243, 209-214). Further studies of morpholino-based oligomeric compounds have also been reported (see: Nasevicius et al., *Nat. Genet.*, 2000, 26, 216-220; and Lacerra et al., *Proc. Natl. Acad. Sci.*, 2000, 97, 9591-9596). Morpholino-based oligomeric compounds are disclosed in U.S. Pat. No. 5,034,506, issued Jul. 23, 1991.

The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

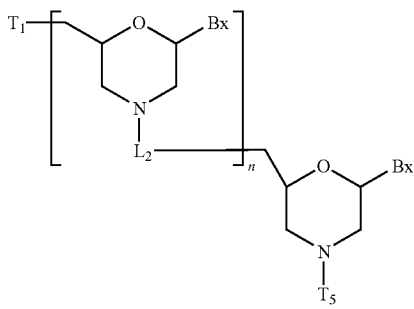

wherein $T_1$ is hydrogen, hydroxyl, a protected hydroxyl, a linked nucleoside or a linked oligomeric compound;

$T_5$ is hydrogen or a phosphate, phosphate derivative, a linked nucleoside or a linked oligomeric compound; and $L_2$ is a linking group which can be varied from chiral to achiral from charged to neutral (U.S. Pat. No. 5,166,315 discloses linkages including —O—P(=O)(N(CH$_3$)$_2$)—O—; U.S. Pat. No. 5,034,506 discloses achiral intermorpholino linkages such as for example: —S(—O)—X— where X is NH, NCH$_3$, O, S, or CH$_2$; —C(—Y)—O— where Y is O or S; —S(=O)(OH)—CH$_2$—; —S(=O)(OH)—N(R)—CH$_2$— where R is H or CH$_3$; and U.S. Pat. No. 5,185,444 discloses phosphorus containing chiral intermorpholino linkages such as for example: —P(=O)(—X)—O— where X is F, CH$_2$R, S—CH$_2$R or NR$_1$R$_2$ and each R, R$_1$ and R$_2$ is H, CH$_3$ or some other moiety that doesn't interfere with the base specific hydrogen bonding; and n is from 7 to about 79.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

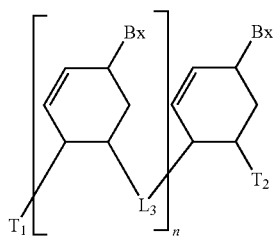

wherein
each Bx is a heterocyclic base moiety;
$L_3$ is an inter cyclohexenyl linkage such as for example a phosphodiester or a phosphorothioate linkage;
$T_1$ is hydrogen, hydroxyl, a protected hydroxyl, a linked nucleoside or a linked oligomeric compound; and
$T_2$ is hydrogen or a phosphate, phosphate derivative, a linked nucleoside or a linked oligomeric compound.

Another class of oligonucleotide mimetic (anhydrohexitol nucleic acid) can be prepared, from one or more anhydrohexitol nucleosides (see, Wouters and Herdewijn, *Bioorg. Med. Chem. Lett.*, 1999, 9, 1563-1566) and would have the general formula:

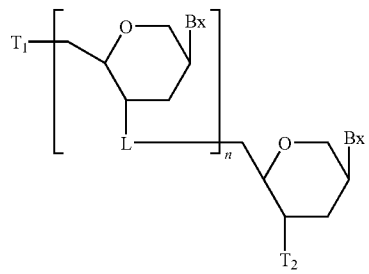

each Bx is a heterocyclic base moiety;
L is an inter anhydrohexitol linkage such as for example a phosphodiester or a phosphorothioate linkage;
$T_1$ is hydrogen, hydroxyl, a protected hydroxyl, a linked nucleoside or a linked oligomeric compound; and
$T_2$ is hydrogen or a phosphate, phosphate derivative, a linked nucleoside or a linked oligomeric compound.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs*, 2001, 2, 558-561; Braasch et al., *Chem. Biol.*, 2001, 8 1-7; and Orum et al., *Curr. Opinion Mol. Ther.*, 2001, 3, 239-243; see also U.S. Pat. Nos. 6,268,490 and 6,670,461). The linkage can be a (—CH$_2$—)x group bridging the 2' oxygen atom and the 4' carbon atom, wherein if x=1 the term LNA is used, if x=2 the term ENA™ is used (Singh et al., Chem. Commun., 1998, 4, 455-456; ENA™: Morita et al., *Bioorganic Medicinal Chemistry*, 2003, 11, 2211-2226). Thus, "ENA™ " is one non limiting example of an LNA. LNA and other bicyclic sugar analogs display very high duplex thermal stabilities with complementary DNA and RNA (Tm=+3 to +10 C), stability towards 3'-exonucleolytic degradation and good solubility properties. LNAs are commercially available from ProLigo (Paris, France and Boulder, Colo., USA). The basic structure of an LNA having a single $CH_2$ linkage in the bicyclic ring system is shown below. This is merely illustrative of one type of LNA.

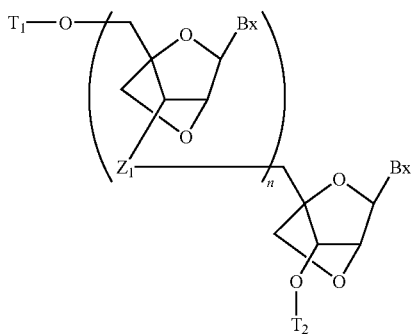

wherein each $T_1$ and $T_2$ is, independently, hydrogen, a hydroxyl protecting group, a linked nucleoside or a linked oligomeric compound, and each $Z_1$ is an internucleoside linking group such as for example phosphodiester or phosphorothioate.

An isomer of LNA that has also been studied is alpha-L-LNA which has been shown to have superior stability against a 3'-exonuclease (Frieden et al., *Nucleic Acids Research*, 2003, 21, 6365-6372). The alpha-L-LNA's were incorporated into antisense gapmers and chimeras that showed potent antisense activity. The structure of alpha-L-LNA is shown below:

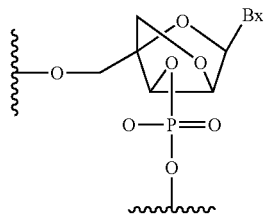

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes. (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of three (3) LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DN/LNA chimeras have been shown to efficiently inhibit gene expression when targeted to a variety of regions (5'-untranslated region, region of the start codon or coding region) within the luciferase mRNA (Braasch et al., *Nucleic Acids Research*, 2002, 30, 5160-5167).

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide-based drugs.

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense compounds. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.*, 2000, 97, 5633-5638) and in another study showed a blockage of the translation of the large subunit of RNA polymerase II (Fluiter et al., *Nucleic Acids Res.*, 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO03/020739; and WO99/14226). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-amino- and 2'-methylamino-LNA's have been prepared and the thermal stability of their duplexes with complementary RNA and DNA strands has been previously reported.

Another oligonucleotide mimetic amenable to the present invention that has been prepared and studied is threose nucleic acid. This oligonucleotide mimetic is based on threose nucleosides instead of ribose nucleosides and has the general structure shown below:

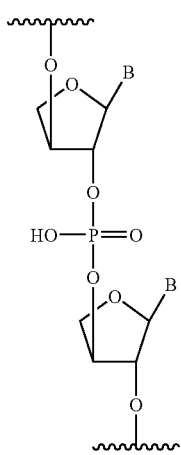

Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in C&EN/Jan. 13, 2003).

In another study it was determined that TNA is capable of antiparallel Watson-Crick base pairing with complementary DNA, RNA and TNA oligonucleotides (Chaput et al., *J. Am. Chem. Soc.*, 2003, 125, 856-857).

In one study (3',2')-alpha-L-threose nucleic acid was prepared and compared to the 2' and 3' amidate analogs (Wu et al., *Organic Letters*, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs having the formulas (amidite monomers shown):

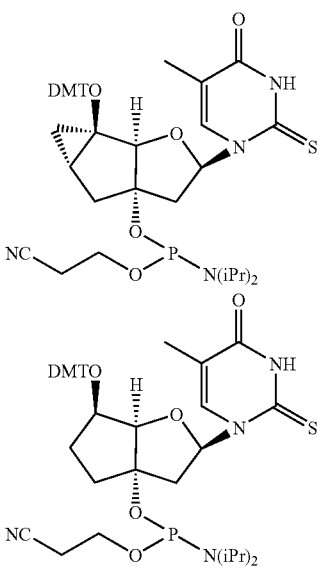

(see Steffens et al., *Helv. Chim. Acta*, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

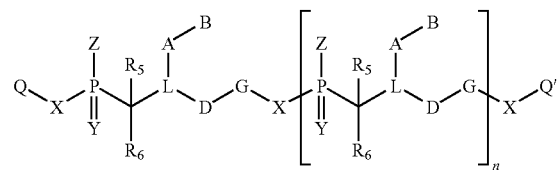

Further oligonucleotide mimetics amenable to the present invention have been prepared wherein a cyclobutyl ring replaces the naturally occurring furanosyl ring.

Modified Internucleoside Linkages

Specific examples of antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. One phosphorus containing modified internucleoside linkage is the phosphorothioate internucleoside linkage, which is linked in a 3'-5' linkage. Oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In some embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— (known as a methylene(methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and —$CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugars

Oligomeric compounds of the invention may also contain one or more substituted or other wise modified sugar moieties. Ribosyl and related sugar moieties are routinely modified at any reactive position not involved in linking. Thus a suitable position for a sugar substituent group is the 2'-position not usually used in the native 3' to 5'-internucleoside linkage. Other suitable positions are the 3' and the 5'-termini. 3'-sugar positions are open to modification when the linkage between two adjacent sugar units is a 2',5'-linkage. Sugar substituent groups include: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

One modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. Further modifications includes 2'-dimethylaminooxyethoxy, i.e., a $O(CH_2)_2ON(CH_3)_2$ group, also known as 2'-DMAOE, as described in examples hereinbelow, 2'-dimethylaminoethoxyethoxy (also known in the art as 2'-O-dimethyl-amino-ethoxy-ethyl or 2'-DMAEOE), i.e., 2'-O—$(CH_2)_2O$—$(CH_2)_2N(CH_3)_2$, and N-methylacetamide (also referred to as NMA, 2'-O—$CH_2$—C(=O)—N(H)$CH_3$.)

Other sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. One 2'-arabino modification is 2'-F (see: Loc et al., *Biochemistry*, 2002, 41, 3457-3467). Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747;5,700,920; and 6,147,200 each of which is herein incorporated by reference in its entirety.

Further representative sugar substituent groups include groups of formula $I_a$ or $II_a$:

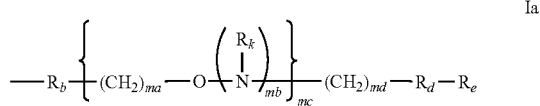

Ia

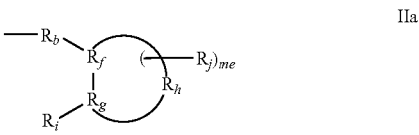

IIa wherein:

$R_b$ is O, S or NH;

$R_d$ is a single bond, O, S or C(=O);

$R_e$ is $C_1-C_{10}$ alkyl, $N(R_k)(R_m)$, $N(R_k)(R_n)$, $N=C(R_p)(R_q)$, $N=C(R_p)(R_r)$ or has formula $III_a$;

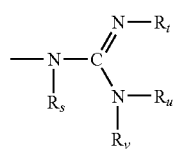

$R_p$ and $R_q$ are each independently hydrogen or $C_1-C_{10}$ alkyl;

$R_r$ is $-R_x-R_y$;

each $R_s$, $R_t$, $R_u$ and $R_v$ is, independently, hydrogen, C(O)$R_w$, substituted or unsubstituted $C_1-C_{10}$ alkyl, substituted or unsubstituted $C_2-C_{10}$ alkenyl, substituted or unsubstituted $C_2-C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1-C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or $-R_x-R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1-C_{10}$ alkyl, substituted or unsubstituted $C_2-C_{10}$ alkenyl, substituted or unsubstituted $C_2-C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$ guanidino and acyl where said acyl is an acid amide or an ester;

or $R_k$ and $R_m$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1-C_8$ alkyl, $C_1-C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

ma is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. Pat. No. 6,172,209, entitled "Capped 2'-Oxyethoxy Oligonucleotides," hereby incorporated by reference in its entirety.

Representative cyclic substituent groups of Formula II are disclosed in U.S. Pat. No. 6,271,358, entitled "RNA Targeted 2'-Oligomeric compounds that are Conformationally Preorganized," hereby incorporated by reference in its entirety.

Sugar substituent groups include $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3))_2$, where n and m are from 1 to about 10.

Representative guanidino substituent groups that are shown in formula III are disclosed in U.S. Pat. No. 6,593,466, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Publication No. WO00/08044895, entitled "2'-O-Dimethylaminoethyloxyethyl-Oligomeric compounds", hereby incorporated by reference in its entirety.

The oligomeric compounds of the invention may also comprise two or more of the same, or chemically distinct, sugar, base, and internucleoside linkage modifications in any combination. The term "chemically distinct" as used herein means different chemical entities whether entirely or partially distinct. For example, an oligomeric compound may comprise a 2'-fluoro and 2'-MOE modification. These two modifications are considered to be chemically distinct entities located within the same molecule.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH_3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer*

Science And Engineering, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently suitable base substitutions, even more particularly when combined with 2'-O-methoxyethyl sugar modifications.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

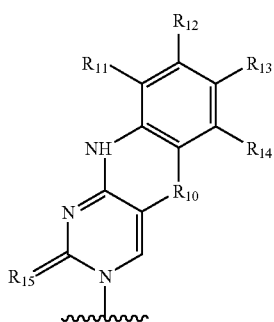

Representative cytosine analogs that make 3 hydrogen bonds with a guanosine in a second strand include 1,3-diazaphenoxazine-2-one ($R_{10}$=O, $R_{11}$—$R_{14}$=H) (Kurchavov, et al., *Nucleosides and Nucleotides*, 1997, 16, 1837-1846), 1,3-diazaphenothiazine-2-one ($R_{10}$=S, $R_{11}$—$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$—$R_{14}$=F) (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155, 920; and U.S. patent application entitled "Nuclease Resistant Chimeric Oligonucleotides" filed May 24, 2002, Ser. No. 10/013,295, both of which are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine. (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183 and U.S. Pat. No. 6,007, 992, the contents of both are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are herein incorporated by reference.

Conjugates

Oligomeric compounds used in the compositions of the present invention can also be modified to have one or more moieties or conjugates for enhancing the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes such as including Cy3 and Alexa. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., dihexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,1109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds used in the compositions of the present invention can also be modified to have one or more stabilizing groups that are generally attached to one or both termini of single-stranded oligomeric compounds or to one or more of the 3' or 5' termini of either strand of a double-stranded compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted a basic moiety; 3'-2'-inverted nucleotide moiety; 3'-2'-inverted a basic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; pbosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

3'-Endo Modifications

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.,* 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense mechanisms including RNAse H, RNAi or any mechanisms that require the binding of a oligomeric compound to an RNA target strand. In the case of antisense, effective inhibition of the mRNA requires that the antisense compound have a sufficiently high binding affinity with the mRNA. Otherwise the desired interaction between the oligomeric antisense compound and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and ¹H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of the RNA interference machinery which is supported in part by the fact that duplexes composed of 2'-deoxy-2'-F-nucleosides appear efficient in triggering an RNAi response in the *C. elegans* system. Properties that are enhanced by using more stable 3'-endo nucleosides include, but aren't limited to, modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds that can act as triggers of the RNAi pathway having one or more nucleosides modified in such a way as to favor a C3'-endo type conformation.

Conformation Scheme

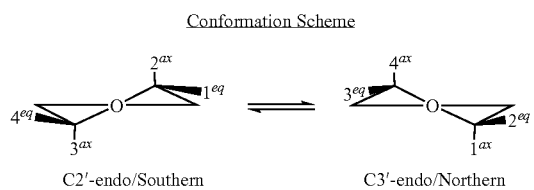

C2'-endo/Southern   C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754).

Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem.

(1976), 41, 3010-3017), or for example modification to yield methanocarba nucleoside analogs (Jacobson et al., *J. Med. Chem. Lett.* (2000), 43, 2196-2203 and Lee et al., *Bioorganic and Medicinal Chemistry Letters* (2001), 11, 1333-1337) also induce preference for the 3'-endo conformation. Along similar lines, oligomeric compounds which trigger an RNAi response might be composed of one or more nucleosides modified in such a way that conformation is locked into a C3'-endo type conformation, i.e. Locked Nucleic Acid (LNA, Singh et al, *Chem. Commun.* (1998), 4, 455-456), and ethylene bridged Nucleic Acids (ENA™, Morita et al, *Bioorganic & Medicinal Chemistry Letters* (2002), 12, 73-76.)

The preferred conformation of modified nucleosides and their oligomers can be estimated by various methods such as molecular dynamics calculations, nuclear magnetic resonance spectroscopy and CD measurements. Hence, modifications predicted to induce RNA-like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press, and the examples section below.)

In one aspect, the present invention is directed to oligomeric compounds that are prepared having enhanced properties, compared to native RNA, against nucleic acid targets. In designing enhanced oligomeric compounds, a target is identified and an oligomeric compound is selected having an effective length and sequence that is complementary to a portion of the target sequence. Each nucleoside of the selected sequence is scrutinized for possible enhancing modifications. One modification would be the replacement of one or more RNA nucleosides with nucleosides that have the same 3'-endo conformational geometry but, in addition, an enhancing property. Such modifications can enhance chemical and nuclease stability relative to native RNA while at the same time being much cheaper and easier to synthesize and/or incorporate into an oligonucleotide. The selected oligomeric compound sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position phosphate of a double-stranded sequence or sequences. Further modifications are also considered such as internucleoside linkages, conjugate groups, substitute sugars or bases, substitution of one or more nucleosides with nucleoside minetics and any other modification that can enhance the affinity of the selected sequence for its intended target.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligomers having the 2'-O-methoxyethyl substituent also have been shown to be antisense inhibitors of gene expression with promising features for in vivo use (Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926). Relative to DNA, the oligomers having the 2'-MOE modification displayed improved RNA affinity and higher nuclease resistance. Chimeric oligomers having 2'-MOE substituents in the wing nucleosides and an internal region of deoxy-phosphorothioate nucleotides (also termed a gapped oligomer or gapmer) have shown effective reduction in the growth of tumors in animal models at low doses. 2'-MOE substituted oligomers have also shown outstanding promise as antisense compounds in several disease states. One such MOE substituted oligomer is approved for the treatment of CMV retinitis.

Most of the 2'-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. $g^+$ or $g^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-MOE substituents, a conserved hydration pattern has been observed for the 2'-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications. The computer simulations were conducted on compounds of SEQ ID NO: 10, above, having 2'-O-modifications located at each of the nucleosides of the oligonucleotide. The simulations were performed with the oligonucleotide in aqueous solution using the AMBER force field method (Cornell et al., *J. Am. Chem. Soc.,* 1995, 117, 5179-5197)(modeling software package from UCSF, San Francisco, Calif.). The calculations were performed on an Indigo2 SGI machine (Silicon Graphics, Mountain View, Calif.).

Another 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, (1997) 25:4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and Tm. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should pre-organize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

In addition, for 2'-substituents containing an ethylene glycol motif, a gauche interaction between the oxygen atoms around the O—C=C—O torsion of the side chain may have a stabilizing effect on the duplex (Freier ibid.). Such gauche interactions have been observed experimentally for a number of years (Wolfe et al., *Acc. Chem. Res.*, 1972, 5, 102; Abe et al., *J. Am. Chem. Soc.*, 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Suitable for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application Ring structures of the invention for inclusion as a 2'-O modification include cyclohexyl, cyclopentyl and phenyl rings as well as heterocyclic rings having special footprints similar to cyclohexyl, cyclopentyl and phenyl rings. 2'-O-substituent groups of the invention included but are not limited to 2'-O-(trans 2-methoxy cyclohexyl, 2'-O-(trans 2-methoxy cyclopentyl, 2'-O-(trans 2-ureido cyclohexyl) and 2'-O-(trans 2-methoxyphenyl).

Chemistries Defined

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one, or about 1 to about 3, hetero atoms in the chain, including the terminal portion of the chain. Heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, from 1 to about 6, and the total number of ring members can vary from three to about 15, or from about 3 to about 8. Ring heteroatoms are N, O and S. Heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Aryl rings have about 6 to about 20 ring carbons. Aryl rings also include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, or from 1 to about 6, and the total number of ring members can vary from three to about 15, or from about 3 to about 8. Ring heteroatoms are N, O and S. Hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Halo (halogen) substituents are F, Cl, Br, and I.

The aforementioned optional substituents are, unless otherwise herein defined, suitable substituents depending upon desired properties. Included are halogens (F, Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate. Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The oligomeric compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Salts, Prodrugs and Bioequivalents:

The oligomeric compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl)phosphate)derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. In one embodiment, double-stranded oligomeric compounds are provided as sodium salts.

As used herein, the term "patient" refers to a mammal that is afflicted with one or more disorders associated with survivin expression or overexpression. It will be understood that the most suitable patient is a human. It is also understood that this invention relates specifically to the inhibition of mammalian survivin expression or overexpression.

It is recognized that one skilled in the art may affect the disorders associated with survivin expression or overexpression by treating a patient presently afflicted with the disorders with an effective amount of the compound of the present invention. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms.

As used herein, the term "effective amount" or "therapeutically effective amount" of a compound of the present invention refers to an amount that is effective in treating or preventing the disorders described herein.

The oligomeric compounds of the present invention can be utilized for diagnostics, therapeutics, prophylaxis and as research reagents and kits. For therapeutics, a patient, such as a human, suspected of having a disease or disorder which can be treated by modulating the expression of survivin is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The present invention also includes pharmaceutical compositions and formulations which include oligomeric compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols; including by nebulizer; intratracheal, intranasal, epidermal, intradermal and transdermal, oral or parenteral. Parenteral administration includes intravenous, intraarterial, subcutaneous, intraperitoneal or intramuscular injection, drip or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable. Compositions for oral administration also include pulsatile delivery compositions and bioadhesive composition as described in copending U.S. patent application Ser. No. 09/944,493, filed Aug. 22, 2001, and Ser. No. 09/935,316, filed Aug. 22, 2001, the entire disclosures of which are incorporated herein by reference. Oral administration for treatment of the disorders is described herein. However, oral administration is not the only route. For example, the intravenous route may be desirable as a matter of convenience or to avoid potential complications related to oral administration. When a compound of the present invention is administered through the intravenous route, an intravenous bolus or slow infusion may be desired.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligomeric compounds of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems,* 1991, 8, 91-192; Muranishi, *Critical Reviews in Therapeutic Drug Carrier Systems,* 1990, 7.1, 1-33). One or more penetration enhancers from one or more of these broad categories may be included. Various fatty acids and their derivatives which act as penetration enhancers include, for example, oleic acid, lauric acid (C12), capric acid (C10), myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, 8:2, 91-192; Muranishi, *Critical Reviews in Therapeutic Drug Carrier Systems,* 1990, 7:1, 1-33; El-Hariri et al., *J. Pharm. Pharmacol.,* 1992, 44, 651-654). Examples of some fatty acids are sodium caprate and sodium laurate, used singly or in combination at concentrations of 0.5 to 5%.

Various natural bile salts, and their synthetic derivatives, act as penetration enhancers. Thus, the term "bile salt" includes any of the naturally occurring components of bile as well as any of their synthetic derivatives. Examples of bile salts are chenodeoxycholic acid (CDCA) and/or ursodeoxycholic acid (UDCA), generally used at concentrations of 0.5 to 2%.

Complex formulations comprising one or more penetration enhancers may be used. For example, bile salts may be used in combination with fatty acids to make complex formulations. Suitable combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, 8:2, 92-192; Muranishi, *Critical Reviews in Therapeutic Drug Carrier Systems*, 1990, 7:1, 1-33; Buur et al., *J. Control Rel.*, 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, 8:2, 92-191); and perfluorochemical emulsions, such as FC-43 (Takahashi et al., *J. Pharm. Pharmacol.*, 1988, 40, 252-257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, 8:2, 92-191); and non-steroidal anti-inflammatory agents such as diclofenac sodium, indomethacin and phenylbutazone (Yamashita et al., *J. Pharm. Pharmacol.*, 1987, 39, 621-626).

A "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligomeric compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. One colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698-708).

Certain embodiments of the invention provide for liposomes and other compositions one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol; vincristine, vinblastine, etoposide (VP-16), trimetrexate, irinotecan, topotecan, gemcitabine, teniposide, cisplatin, carboplatin and diethylstilbestrol (DES). See, generally, *The Merck Manual of Diagnosis and Therapy*, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, weekly, monthly, or yearly. For double-stranded compounds, the dose must be calculated to account for the increased nucleic acid load of the second strand (as with compounds comprising two separate strands) or the additional nucleic acid length (as with self complementary single strands having double-stranded regions).

Double-stranded compounds can be introduced into cells in a number of different ways. For example, the double-stranded compounds can be administered by microinjection; bombardment by microparticles covered by the double-stranded compounds; soaking the cells in a solution of the double-stranded compounds; electroporation of cells in the presence of the double-stranded compounds; liposome-mediated delivery of double-stranded compounds; transfection mediated by chemicals such as calcium phosphate, cationic lipids, etc.; viral infection; transformation; and the like. The double-stranded compounds can be introduced along with components that enhance RNA uptake by the cells, stabilize the annealed strands, or otherwise increase the inhibition of function of the target polynucleotide sequence. In the case of a cell culture or tissue exponent, the cells are conveniently incubated in a solution containing the double-stranded compounds, or subjected to lipid-mediated transformation.

Determination of the optimal amounts of double-stranded compounds to be administered to human or animal patients for the prevention or treatment of pathologies associated with survivin expression or overexpression, as well as methods of administering therapeutic or pharmaceutical compositions comprising such double-stranded oligonucleotides, is within the skill of those in the pharmaceutical art. Dosing of a human or animal patient is dependent on the nature of the symptom, condition, or disease; the nature of the infected cell or tissue; the patient's condition; body weight; general health; sex; diet; time, duration, and route of administration; rates of absorption, distribution, metabolism, and excretion of the double-stranded compounds; combination with other drugs; severity of the pathology; and the responsiveness of the disease state being treated. The amount of double-stranded compounds administered also depends on the nature of the target polynucleotide sequence or region thereof, and the nature of the double-stranded compounds, and can readily be optimized to obtain the desired level of effectiveness. The course of treatment can last from several days to several weeks or several months, or until a cure is effected or an acceptable diminution or prevention of the disease state is achieved. Optimal dosing schedules can be calculated from measurements of drug accumulation in the body of the patient in conjunction with the effectiveness of the treatment. Persons of ordinary skill can easily determine optimum dosages, dosing methodologies, and repetition rates.

While the embodiments of the invention have been described with specificity in accordance with certain of the embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham, Mass. or Glen Research, Inc. Sterling, Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods (Sanghvi, et. al., *Nucleic Acids Research*, 1993, 21, 3197-3203) using commercially available phosphoramidites (Glen Research, Sterling Va. or ChemGenes, Needham, Mass.).

2'-Fluoro amidites

2'-Fluorodeoxyadenosine amidites

2'-fluoro oligonucleotides were synthesized as described previously (Kawasaki, et. al., *J. Med. Chem.*, 1993, 36, 831-841) and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom was introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with ThP to give diisobutyryl di-THP protected arabinofuranosylguanine.

Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites were prepared as follows, or alternatively, as per the methods of Martin, P., *Helvetica Chimica Acta*, 1995, 78, 486-504.

2,2'-Anhydro(1-(beta-D-arabinofuranosyl)-5-methyluridine)

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methyl-cytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(iso-propyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/Hexane (3:1) as the eluting solvent. The pure fractions were combined to give 90.6 g (87%) of the title compound.

2'-(Aminooxyethyl) nucleoside amidites and 2'-(dimethylaminooxyethyl) nucleoside amidites Aminooxyethyl and dimethylaminooxyethyl amidites are prepared as per the methods of U.S. Pat. No. 6,127,533 which is herein incorporated by reference.

Example 2

Oligonucleotide Synthesis

Unsubstituted and substituted phosphodiester (P=O) oligonucleotides were synthesized on an automated DNA synthesizer (Applied Biosystems model 380B) using standard phosphor-amidite chemistry with oxidation by iodine.

Phosphorothioates (P=S) were synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hours), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference. 3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

4-Ribonucleoside and 2'-deoxy-4'-ribonucleoside compositions may be made by the method taught by Naka et al., *J. Am. Chem. Soc.* 122:7233-7243, 2000 and U.S. Pat. No. 5,639,873, which are incorporated by reference herein in their entirety.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference. The oligomeric compounds of the invention may also comprise mixed linkages in which any number of two or more types of linkages are present in any order and at any position within the oligomeric compound, for example the 5' half of the compound comprising phosphorothioate linkages and the 3' half comprising phosphodiester linkages. These are referred to as mixed phosphorothioate and phosphodiester linkages Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5-23. They may alsb be prepared in accordance with U.S. Pat. Nos. 5,539,082, 5,700,922, and 5,719,262; herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

Double-stranded compounds of the invention can be of several types including but not limited to, siRNAs, canonical siRNAs, blunt-ended siRNAs or hairpins. Single-stranded compounds of the invention which elicit the RNAi antisense mechanism are also within the scope of the invention. These include, but are not limited to, ssRNAi and antisense RNA (asRNA).

(2'-O-Me)-(2'-deoxy)-(2'-O-Me)chimeric phosphorothioate oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-MOE modified nucleotides. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

(2'-O-(2-Methoxyethyl))-(2'-deoxy)-(2'-O-(Methoxyethyl))ohimeric phosphorothioate oligonucleotides (2'-O-(2-methoxyethyl))-(2'-deoxy)-(–2'-O-(methoxyethyl))chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl)Phosphodiester)chimeric oligonucleotides (2'-O-(2-methoxyethyl phosphodiester)-(2'-deoxy phosphorothioate)-(2'-O-(methoxyethyl)phosphodiester)chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides, whether single or double stranded) of the present invention can be synthesized by the methods herein or purchased from Dharmacon Research, Inc (Lafayette, Colo.). Once synthesized, complementary RNA antisense compounds can then be annealed by methods known in the art to form double-stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis-96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACEJ MDQ) or, for individually prepared samples, on a commercial CE apparatus (e.g., Beckman P/ACEJ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used.

MCF7:

The human breast carcinoma cell line MCF-7 was obtained from the American Type Culture Collection (Manassas, Va.).

MCF-7 cells were routinely cultured in DMEM low glucose (Invitrogen Life Technologies, Carlsbad, Calif.) supplemented with 10% fetal calf serum (Invitrogen Life Technologies, Carlsbad, Calif.). Cells were routinely passaged by trypsinization and dilution when they reached about 90% confluence. Cells were seeded into 96-well plates (Falcon-Primaria #3872) at a density of about 7000 cells/well for use in RT-PCR analysis. For Northern blotting or other analyses, cells may be seeded onto 100 mm or other standard tissue culture plates and treated similarly, using appropriate volumes of medium and oligonucleotide.

HeLa Cells:

The human epitheloid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached approximately 90% confluence. Cells were seeded into 24-well plates (Falcon-Primaria #3846) at a density of approximately 50,000 cells/well or in 96-well plates at a density of approximately 5,000 cells/well for use in RT-PCR analysis. For Northern blotting or other analyses, cells were harvested when they reached approximately 90% confluence.

U-87 MG Cells:

The human glioblastoma U-87 MG cell line was obtained from the American Type Culture Collection (Manassas, Va.). U-87 MG cells were cultured in DMEM (Invitrogen Life Technologies, Carlsbad, Calif.) supplemented with 10% fetal bovine serum (Invitrogen Life Technologies, Carlsbad, Calif.) and antibiotics. Cells were routinely passaged by trypsinization and dilution when they reached appropriate confluence. Cells were seeded into 96-well plates (Falcon-Primaria #3872) at a density of about 10,000 cells/well for use in RT-PCR analysis.

For Northern blotting or other analyses, cells may be seeded onto 100 mm or other standard tissue culture plates and treated similarly, using appropriate volumes of medium and oligonucleotide. For Northern blotting or other analyses, cells may be seeded onto 100 mm or other standard tissue culture plates and treated similarly, using appropriate volumes of medium and oligonucleotide.

HUVEC Cells:

HUVEC were obtained from ATCC and routinely cultured in EBM (Clonetics Corp, Walkersille, Md.) supplemented with SingleQuots supplements. Cells were routinely passaged by trypsinizaiton and dilution when they reached 90% confluence were maintained for up to 15 passages. For cells grown in 96-well plates (10,000 cells/well), wells were washed once with 200 µL OPTI-MEM-1™ reduced-serum medium (Gibco BRL) and then treated with 130 µL of OPTI-MEM-1™ containing 12 µg/mL LIPOFECTIN™ (Gibco BRL) and the desired double-stranded compounds at a final concentration of 25 nM. After 5 hours of treatment, the medium was replaced with fresh medium. Cells were harvested 16 hours after dsRNA treatment, at which time RNA was isolated and target reduction measured by RT-PCR.

Treatment with Oligomeric Compounds:

When cells reached 80% confluency, they were treated with oligonucleotide. For cells grown in 96-well plates, wells were washed once with 200 µL OPTI-MEMJ-1 reduced-serum medium (Gibco BRL) and then treated with 130 µL of OPTI-MEM-1 containing 3.75 µg/mL LIPOFECTINJ (Gibco BRL) and the desired oligonucleotide at a final concentration of 150 nM. For dsRNA compounds, 2×130 µL of OPTI-MEM-1 was used. After 4 hours of treatment, the medium was replaced with fresh medium. Cells were harvested 16 hours after oligonucleotide treatment. The concentration of oligonucleotide used varies from cell line to cell line. To determine the optimal oligonucleotide concentration for a particular cell line, the cells are treated with a positive control oligonucleotide at a range of concentrations. For human cells the positive control RNAse H oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGC-CCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of H-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Survivin Expression

Antisense modulation of survivin expression can be assayed in a variety of ways known in the art. For example, survivin mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM 7700 Sequence Detection System, available from PE-Applied Biosystems, Foster City, Calif. and used according to manufacturer's instructions. Other methods of PCR are also known in the art.

Survivin protein levels can be quantitated in a variety of ways well known in the art, such as immunoprecipitation, Western blot analysis (immunoblotting), ELISA or fluorescence-activated cell sorting (FACS). Antibodies directed to survivin can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Auslibel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758-1764. Other methods for poly (A)+ mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96 kit and buffers purchased from Qiagen, Inc. (Valencia, Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pippeting three times up and down. The samples were then transferred to the RNEASY 96 well plate attached to a QIAVAC manifold fitted with a waste collection tray and attached to a vacuum source. Vacuum was applied for 15 seconds. 1 mL of Buffer RW1 was added to each well of the RNEASY 96 plate and the vacuum again applied for 15 seconds. 1 mL of Buffer RPE was then added to each well of the RNEASY 96 plate and the vacuum applied for a period of 15 seconds. The Buffer RPE wash was then repeated and the vacuum was applied for an additional 10 minutes. The plate was then removed from the QIAVAC manifold and blotted dry on paper towels. The plate was then re-attached to the QIAVAC manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

Example 13

Real-time Quantitative PCR Analysis of Survivin mRNA Levels

Quantitation of survivin mRNA levels was determined by real-time quantitative PCR using the ABI PRISM 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 µL PCR cocktail (1× TAQMAN buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD, and 12.5 Units MuLV reverse transcriptase) to 96 well plates containing 25 µL poly(A) mRNA solution. The RT reaction was carried out by incubation for 30 minutes at 48° C. Following a 10 minute incubation at 95° C. to activate the AMPLITAQ GOLD, 40 cycles of a two-step PCR protocol were carried out: 95° C. for 15 seconds (denaturation) followed by 60° C. for 1.5 minutes (annealing/extension). Probes and primers to human survivin were designed to hybridize to a human survivin sequence, using published sequence information (GenBank accession number U75285, incorporated herein as SEQ ID NO:3). For human survivin the PCR primers were: forward primer: AAGGACCACCG-CATCTCTACA (SEQ ID NO: 4) reverse primer:

CCAAGTCTGGCTCGTTCTCAGT (SEQ ID NO: 5) and the PCR probe was: FAM-CGAGGCTGGCTTCATCCACT-GCC-TAMRA (SEQ ID NO: 6) where FAM (PE-Applied Biosystems, Foster City, Calif.) is the fluorescent reporter dye) and TA A (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGG-GATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye and TAMRA (PE-Applied Biosystems, Foster City, Calif.) is the quencher dye.

Example 14

Western Blot Analysis of Survivin Protein Levels

Western blot analysis (immunoblot analysis) is carried out using standard methods. Cells are harvested 16-20 hours after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to survivin is used, with a radiolabelled or fluorescently labeled secondary antibody directed against the primary antibody species. Bands are visualized using a PHOSPHORIMAGER™ (Molecular Dynamics, Sunnyvale, Calif.).

Example 15

Design and Screening of Double-stranded Antisense Compounds (siRNAs) Targeting Survivin In accordance with the present invention, a series of double-stranded oligomeric compounds (siRNAs) comprising the antisense compounds of the present invention and their complements can be designed to target survivin. The nucleobase sequence of the antisense strand of the duplex comprises at least a portion of an oligonucleotide targeted to survivin as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence: CGAGAGGCGGACGGGACCG (SEQ ID NO: 10) and having a two-nucleobase overhang of deoxythymidine(dT) would have the following structure:

```
cgagaggcggacgggaccgTT  Antisense   (SEQ ID NO:11)

TTgctctccgcctgccctggc  Complement  (SEQ ID NO:12)
```

As shown, this double-stranded compound represents a canonical siRNA.

In another embodiment, a duplex comprising an antisense strand having the same sequence CGAGAGGCGGACGG-GACCG (SEQ ID NO: 10) may be prepared with blunt ends (no single-stranded overhang) as shown:

```
cgagaggcggacgggaccg  Antisense   (SEQ ID NO:10)

gctctccgcctgccctggc  Complement  (SEQ ID NO:13)
```

As shown, this double-stranded compound represents a blunt-ended siRNA.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds (siRNAs) are evaluated for their ability to modulate survivin expression according to the protocols described herein.

Cell Culture Conditions, Determination of $IC_{50}$ Values for dsRNAs In Vitro IC50

In vitro $IC_{50}$ values for dsRNAs of the present invention can be determined by contacting in vitro varying concentrations of dsRNAs and appropriate cell lines, tissues, or organs exhibiting pathologies associated with survivin expression or overexpression, and determining the quantitative effect(s) of these dsRNAs at such concentrations on parameters including, but not limited to, various steps, stages, or aspects of survivin pathology or pathogenesis. Representative parameters that can be studied include, for example, translation of survivin mRNAs or survivin protein synthesis; effect on surrogate markers; or any other parameter that is indicative of potential dsRNA therapeutic effectiveness that can be conveniently measured in vitro.

Given the state of the art, it should be possible for one of ordinary skill to either adapt currently existing cell-based assays, or develop completely novel in vitro assays, to determine $IC_{50}$ values for the dsRNAs disclosed herein without undue experimentation.

Western Blots:

For western blot analysis, cells are plated in 10 cm tissue culture dishes (Falcon, #3003) at a density of $7.5 \times 10^5$ cells/dish. For RT-PCR analysis, 96-well plates (Corning Incorporated, #3596) are plated with $1 \times 10^4$ cells/well. Lipofectin (GIBCO/Invitrogen) transfection reagent is used at a concentration of 3 ul/ml OPTIMEM reduced serum medium (Gibco/Invitrogen)/100 nM siRNA duplex. Lipofectin reagent is incubated with OPTIMEM medium for 30 minutes prior to the addition of siRNA. The desired amount of siRNA is added and mixed. Further 1:1 dilutions are performed in OPTIMEM. Cells are washed twice with 1× phosphate buffered saline and then treated with the siRNA/Lipofectin mixture in OPTIMEM. After a 4 hr incubation period, OPTIMEM medium is replaced with complete growth medium. Cells are harvested after additional 16-20 hrs for Western blot or RT-PCR analysis.

At the end of the incubation period culture medium is removed and cells are washed twice with PBS. Cells are lysed in RIPA buffer (20 mM Tris-HCl, pH 7.4, 5 mM EDTA, 50 mM NaCl, 10 mM Sodium Pyrophosphate, 50 mM Sodium Fluoride, and 1% Nonidet P40) plus Complete™ Mini protease inhibitor tablets (Roche, #1836153) and 1 mM Sodium orthovanadate (Sigma) by directly adding buffer to the plate. Lysates are collected by scrapping, transferred to microfuge tubes and cleared from the cellular debris by centrifugation at 14,000 rpm for 30 minutes at 4° C. Protein concentrations are determined using BCA protein assay yeagents (Pierce). Total cellular protein is subjected to SDS-PAGE and transferred onto Immobilon-P membranes (Millipore, #IPVHO91). Membranes are probed with primary antibodies to survivin (R&D Systems, #AF886) and to β-Actin (Sigma, #A5441). Horseradish peroxidase linked Anti-rabbit Ig, and anti-mouse Ig, antibodies (Pharmacia) are used as secondary antibodies. Antigen-antibody complexes are visualized by incubation of membrane in SuperSignal West Pico chemiluminescence reagents (Pierce) for 5 minutes followed by capturing of the chemiluminescence using Fluor-S imager (Biorad) equipped with the cool CCD camera. The protein bands of interest for each sample are quantified using Quantity One software (Biorad). The percentage inhibition for each samples are calculated by comparing the survivin/Actin protein ratio for the sample to survivin/Actin protein ratio for the untreated control. The $IC_{50}$ is derived from the non-linear regression analysis of the percentage inhibition data using GraphPad Prism software (GraphPad Software).

RNA Isolation:

Total RNA is isolated using RNeasy® 96 kit according to recommended protocol (Qiagen). Briefly, cells are washed with 200 ul PBS after removal of growth medium. Following washing, 100 μl buffer RLT is added, plate is shaken vigorously for about 20 seconds. To each well 100 μl 70% ethanol are added and mixed by pipetting up and down three times. Samples are then applied into the wells of the RNeasy 96 plate placed in the QIAvac top base of the QIAvac 96 manifold, which is attached to a vacuum source. Vacuum is applied for 30 seconds or until transfer is complete. To each well 80 μl of DNase I incubation mix (20 mM Tris-HCl, pH 8.4, 2 mM $MgCl_2$, 50 mM KCl and 225 Units/ml DNase I from Invitrogen) is added and incubated at room temperature for 30 minutes. Buffer RW1 (1 ml/well) is added and the vacuum is applied for 30 seconds. Buffer RPE (1 ml/well) is added to each well and vacuum is applied for 30 seconds. Washing steps with buffer RW1 and RPE1 are repeated once more. The plate is then removed from the manifold and blotted dry on paper towels. The plate is placed back in the QIAvac manifold and the vacuum is applied for 10 minutes. To elute RNA 30 μl of RNase-free water is added directly onto the membrane of each well, incubated for 1 minutes and vacuum is applied for 30 seconds. In order to maximize the recovery of total RNA the elution step is repeated with additional 30 μl/well RNase-free water.

Quantitation of Surviving:

Quantitation of survivin and GAPDH mRNA levels is determined by real-time quantitative RT-PCR using the ABI PRISM® 7900 Sequence Detection System (Applied Biosystems). RT-PCR reactions are carried out by adding 15 ul of TaqMan One Step PCR Master Mix (Applied Biosystems, #4309169) reagents (containing 100 nM each of forward primer and reverse primer, and 200 nM probe) to 96-well plates with 10 μl total RNA. For human survivin, the forward PCR primer is: 5'GCACCACTTCCAGGGTTTATTC3' (SEQ ID NO: 186), and the reverse primer is: 5'TCTCCTTTCCTAAGACATTGCTAAGG3' (SEQ ID NO: 187). The survivin TaqMan® probe used is 5'(FAM)TGGTGCCACCAGCCTTCCTGTG3' (SEQ ID NO: 188) (Biosearch Technologies, Inc.). This primer-probe set, designed to SEQ ID No 14 was used for all experiments in Examples 15 to the end. For human GAPDH, TaqMan GAPDH Control Reagent Kit is used (Applied Biosystems, #402869). The percentage inhibition for each samples are calculated by comparing the survivin/GAPDH mRNA ratio for the sample to survivin/GAPDH mRNA ratio for the untreated control. The $IC_{50}$ is derived from the non-linear regression analysis of the percentage inhibition data using GraphPad Prism software (GraphPad Software).

Example 16

Design of Phenotypic Assays and In Vivo Studies for the Use of Survivin Inhibitors Phenotypic Assays Once active oligomeric compounds targeting survivin have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of survivin in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with survivin inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the survivin inhibitors. Hallmark genes, or those genes suspected to be associated with a specific disease state, condition, or phenotype, are measured in both treated and untreated cells.

Example 17

Modulation of Human Survivin Expression by Double-stranded RNA (dsRNA)

In accordance with the present invention, a series of double-stranded oligomeric compounds comprising the antisense compounds of the present invention and their complements thereof, were designed to target survivin mRNA. The sense strand of the dsRNA is designed and synthesized as the reverse complement of the antisense strand, a list of which is shown in Table 1. The oligomeric compounds were evaluated in HeLa cells. Culture methods used for HeLa cells are found, for example, at www.atcc.org.

For cells grown in 96-well plates, wells were washed once with 200 μL OPTI-MEM-1™ reduced-serum medium (Gibco BRL) and then treated with 130 μL of OPTI-MEM-1™ containing 12 μg/mL LIPOFECTIN™ (Gibco BRL) and the desired dsRNA at a final concentration of 25 nM. After 5 hours of treatment, the medium was replaced with fresh medium. Cells were harvested 16 hours after dsRNA treatment, at which time RNA was isolated and target reduction measured by RT-PCR as described above.

The antisense sequences of the dsRNA oligomeric compounds are shown in Table 1. Prior to treatment of the HeLa cells, the dsRNA oligomers were generated by annealing the antisense and sense strands according to the method outlined in Example 16. Target sites are indicated by the first (5' most) nucleotide number, as given in the sequence source reference (Genbank accession no. NM_001168.1, incorporated herein as SEQ ID NO: 14), to which the antisense strand of the dsRNA oligonucleotide binds.

All compounds in Table 1 are dsRNAs, 20 nucleotides in length with the antisense strand listed first (top strand) in the 5' to 3' orientation, and the sense strand listed second (bottom strand), also in the 5' to 3' orientation. All nucleosides are ribose and backbone linkages are phosphate (P=O). "Target site" refers to the 5'-most position of the target region on the survivin mRNA to which the antisense strand is targeted. As such, these compounds are blunt-ended siRNAs.

Data were obtained by real-time quantitative PCR as described herein. HeLa cells were treated with double stranded oligomeric compounds (composed of antisense strands hybridized to their corresponding sense strands) targeting human survivin mRNA.

TABLE 1

Inhibition of human survivin mRNA levels by dsRNA oligomeric compounds

| Strand | ISIS # | REGION | TARGET SITE | SEQUENCE | SEQ ID NO | % INHIB |
|---|---|---|---|---|---|---|
| AS | 339044 | coding | 67 | agggcugccaggcagggggc | 15 | ND |
| S | 339074 | | | gcccugccuggcagcccu | 16 | |
| AS | 339045 | coding | 456 | auccauggcagccagcugcu | 17 | 86 |
| S | 339075 | | | agcagcuggcugccauggau | 18 | |
| AS | 339046 | 3'UTR | 512 | aacccuggaaguggugcagc | 19 | 28 |
| S | 339076 | | | gcugcaccacuuccagggu | 20 | |
| AS | 339047 | 3'UTR | 534 | aggcugguggcaccagggaa | 21 | 9 |
| S | 339077 | | | uucccuggugccaccagccu | 22 | |
| AS | 339048 | 3'UTR | 586 | auuugaaaauguugaucucc | 23 | 86 |
| S | 339078 | | | ggagaucaacauuuucaaau | 24 | |
| AS | 339049 | 3'UTR | 605 | agcacaguugaaacaucuaa | 25 | 71 |
| S | 339079 | | | uuagauguuucaacugugcu | 26 | |
| AS | 339050 | 3'UTR | 642 | agaagcaccucuggugccac | 27 | 51 |
| S | 339080 | | | guggcaccagaggugcuucu | 28 | |
| AS | 339051 | 3'UTR | 756 | ucccucacuucucaccuggu | 29 | 48 |
| S | 339081 | | | accaggugagaagugaggga | 30 | |
| AS | 339052 | 3'UTR | 780 | gcaaaagggacacugccuuc | 31 | 85 |
| S | 339082 | | | gaaggcagugucccuuuugc | 32 | |
| AS | 339053 | 3'UTR | 815 | aggcucugcccacgcgaaca | 33 | 21 |
| S | 339083 | | | uguucgcgugggcagagccu | 34 | |
| AS | 339054 | 3'UTR | 846 | caacaugagguccagacaca | 35 | 50 |
| S | 339084 | | | ugugucuggaccucauguug | 36 | |
| AS | 339055 | 3'UTR | 876 | aguccacucaggacugug | 37 | 59 |
| S | 339085 | | | cacaguccugagugugacu | 38 | |
| AS | 339056 | 3'UTR | 914 | uaaggaaccugcagcucaga | 39 | 86 |
| S | 339086 | | | ucugagcugcagguuccuua | 40 | |
| AS | 339057 | 3'UTR | 1030 | cagggacucugucuccauuc | 41 | 48 |
| S | 339087 | | | gaauggagacagaguccog | 42 | |

TABLE 1-continued

Inhibition of human survivin mRNA levels by dsRNA oligomeric compounds

| Strand | ISIS # | REGION | TARGET SITE | SEQUENCE | SEQ ID NO | % INHIB |
|---|---|---|---|---|---|---|
| AS | 339058 | 3'UTR | 1070 | aacaaaauaagaaagccaug | 43 | 78 |
| S | 339088 | | | cauggcuuucuuauuuuguu | 44 | |
| AS | 339059 | 3'UTR | 978 | gcuauucgugaauuaacaa | 45 | 65 |
| S | 339089 | | | uuguuaauucacagaauagc | 46 | |
| AS | 339060 | 3'UTR | 1101 | aguuugugcuauucugugaa | 47 | 85 |
| S | 339090 | | | uucacagaauagcacaaacu | 48 | |
| AS | 339061 | 3'UTR | 1130 | agaauggcuuugugcuuagu | 49 | 48 |
| S | 339091 | | | acuaagcacaaagccauucu | 50 | |
| AS | 339062 | 3'UTR | 1165 | uccaccugaaguucaccccg | 51 | 73 |
| S | 339092 | | | cggggugaacuucaggugga | 52 | |
| AS | 339063 | 3'UTR | 1212 | aaggaguaucugccagacgc | 53 | 67 |
| S | 339093 | | | gcgucuggcagauacuccuu | 54 | |
| AS | 339064 | 3'UTR | 1232 | uaaucacacagcaguggcaa | 55 | 73 |
| S | 339094 | | | uugccacugcuguguugauua | 56 | |
| AS | 339065 | 3'UTR | 1258 | gugcccgcggcucacuggg | 57 | 19 |
| S | 339095 | | | cccagugagccgcggggcac | 58 | |
| AS | 339066 | 3'UTR | 1305 | aaaggauuuaggccacugcc | 59 | 73 |
| S | 339096 | | | ggcaguggccuaaauccuuu | 60 | |
| AS | 339067 | 3'UTR | 1329 | acagcaucgagccaagucau | 61 | 63 |
| S | 339097 | | | augacuuggcucgaugcugu | 62 | |
| AS | 339068 | 3'UTR | 1366 | acagacacacggccugcagc | 63 | 20 |
| S | 339098 | | | gcugcaggccgugugucugu | 64 | |
| AS | 339069 | 3'UTR | 1394 | gaacgugacagaugugaagg | 65 | 43 |
| S | 339099 | | | ccuucacaucugucacguuc | 66 | |
| AS | 339070 | 3'UTR | 1487 | uccaucaucuuacgccagac | 67 | 74 |
| S | 339100 | | | gucuggcguaagaugaugga | 68 | |
| AS | 339071 | 3'UTR | 1498 | ggcgaaucaaauccaucauc | 69 | 57 |
| S | 339101 | | | gaugauggauuugauucgcc | 70 | |
| AS | 339072 | 3'UTR | 1529 | auccacccugcagcucuaug | 71 | 31 |
| S | 339102 | | | cauagagcugcagggguqgau | 72 | |
| AS | 339073 | 3'UTR | 1569 | gccgagaugaccuccagagg | 73 | 50 |
| S | 339103 | | | ccucuggaggucaucucggc | 74 | |
| AS | 341881 | 3'UTR | 584 | uuugaaaauguugaucucctt | 75 | 93 |
| S | 341880 | | | ggagaucaacauuuucaaatt | 76 | |
| AS | 341883 | 3'UTR | 1068 | acaaaauaagaaagccaugtt | 77 | 80 |
| S | 341882 | | | cauggcuuucuuauuuugutt | 78 | |
| AS | 341885 | 3'UTR | 1303 | aaggauuuaggccacugcctt | 79 | 78 |
| S | 341884 | | | ggcaguggccuaaauccuutt | 80 | |

All dsRNA compounds except ISIS 339046, 339047, 339053, 339065, 339068 and 339072 demonstrated over 45% inhibition of survivin expression.

In a dose-response experiment, HeLa cells were treated with 1.1, 3.3, 10 and 30 nM of the indicated oligonucleotide mixed with 3 ug/mL LIPOFECTIN per 100 nM oligonucleotide as described by other examples herein. Untreated cells served as controls. Following 16 hours of treatment, RNA was prepared from cells for subsequent real-time PCR analysis.

Human survivin mRNA expression levels were quantitated by real-time PCR and gene target quantities were normalized using Ribogreen as described in other examples herein. Data are averages from two experiments and are shown in Table 2.

The identity of the two strands of the duplex are shown separated by an underscore, with the antisense strand shown first (antisense strand_sense strand).

TABLE 2

Inhibition of human survivin mRNA levels by dsRNA oligomeric compounds: dose response
Percentage of Inhibition of survivin expression in HeLa cells

| | Oligonucleotide Concentration | | | |
|---|---|---|---|---|
| Isis # | 1.1 nM | 3.3 nM | 10 nM | 30 nM |
| 339045_339075 | 24 | 44 | 62 | 81 |
| 339048_339078 | 42 | 59 | 74 | 83 |
| 339052_339082 | 26 | 55 | 70 | 83 |
| 339056_339086 | 35 | 54 | 72 | 81 |
| 339058_339088 | 22 | 44 | 63 | 75 |
| 339060_339090 | 20 | 50 | 70 | 85 |

As shown in Table 2, the compounds tested inhibit human survivin mRNA expression in HeLa cells in a concentration-dependent manner.

Example 18

Modulation of Human Survivin Expression by Double-stranded RNA (dsRNA) with a 5'-phosphate Cap In accordance with the present invention, a series of double-stranded oligomeric compounds comprising the antisense compounds shown in Table 1 (ISIS 339045-339073), each modified with a 5'-terminal phosphate group, and the complements thereof, were designed to target survivin mRNA. The corresponding dsRNA compounds are ISIS 341201-341229 (Table 35. The sense strand of the dsRNA was designed and synthesized as the complement of the antisense strand, a list of which is shown in Table 2. The oligomeric compounds were evaluated in HeLa cells. Culture methods used for HeLa cells are found, for example, at www.atcc.org.

For cells grown in 96-well plates, wells were washed once with 200 μL OPTI-MBM-1™ reduced-serum medium (Gibco BRL) and then treated with 130 μL of OPTI-MEM-1™ containing 12 μg/mL LIPOFECTIN™ (Gibco BRL) and the desired dsRNA at a final concentration of 25 nM. After 5 hours of treatment, the medium was replaced with fresh medium. Cells were harvested 16 hours after dsRNA treatment, at which time RNA was isolated and target reduction measured by RT-PCR.

The dsRNA oligomeric compounds are shown in Table 3. Prior to treatment of the HeLa cells, the dsRNA oligomers were generated by annealing the antisense and sense strands according to the method outlined in Example 17. Target sites are indicated by the first (5' most) nucleotide number, as given in the sequence source reference (Genbank accession no. NM_001168.1, incorporated herein as SEQ ID NO: 14), to which the antisense strand of the dsRNA oligonucleotide binds.

All compounds in Table 3 are oligoribonucleotides, 20 nucleotides in length with the antisense strand shown first, and the sense strand shown second, both in the 5' to 3' direction. Compounds in Table 3 have phosphate (P=O) backbones and also comprise a terminal 5'-phosphate cap on each strand. The compounds in Table 3 are blunt-ended siRNAs.

Data were obtained by real-time quantitative PCR as described in other examples herein. HeLa cells were treated with double stranded oligomeric compounds targeting human survivin mRNA.

TABLE 3

Inhibition of human survivin mRNA levels by dsRNA oligomeric compounds with a 5'-phosphate cap

| Strand | ISIS # | REGION | SEQUENCE | SEQ ID NO | % INHIB |
|---|---|---|---|---|---|
| AS | 341201 | Coding | auccauggcagccagcugcu | 17 | 85 |
| S | 341231 | | agcagcuggcugccauggau | 18 | |
| AS | 341202 | 3'UTR | aacccuggaaguggugcagc | 19 | 42 |
| S | 341232 | | gcugcaccacuuccaggguu | 20 | |
| AS | 341203 | 3'UTR | aggcugguggcaccagggaa | 21 | 23 |
| S | 341233 | | uucccuggugccaccagccu | 22 | |
| AS | 341204 | 3'UTR | auuugaaaauguugaucucc | 23 | 84 |
| S | 341234 | | ggagaucaacauuuucaaau | 24 | |
| AS | 341205 | 3'UTR | agcacaguugaaacaucuaa | 25 | 78 |
| S | 341235 | | uuagauguuucaacugugcu | 26 | |
| AS | 341206 | 3'UTR | agaagcaccucuggugccac | 27 | 61 |
| S | 341236 | | guggcaccagaggugcuucu | 28 | |
| AS | 341207 | 3'UTR | ucccucacuucucaccuggu | 29 | 58 |
| S | 341237 | | accaggugagaagugaggga | 30 | |
| AS | 341208 | 3'UTR | gcaaaagggacacugccuuc | 31 | 84 |
| S | 341238 | | gaaggcagugucccuuuugc | 32 | |
| AS | 341209 | 3'UTR | aggcucugcccacgcgaaca | 33 | 33 |
| S | 341239 | | uguucgcgugggcagagccu | 34 | |
| AS | 341210 | 3'UTR | caacaugagguccagacaca | 35 | 66 |
| S | 341240 | | ugugucuggaccucauguug | 36 | |
| AS | 341211 | 3'UTR | aguccacacucaggacugug | 37 | 71 |
| S | 341241 | | cacaguccugagugugggacu | 38 | |
| AS | 341212 | 3'UTR | uaaggaaccugcagcucaga | 39 | 85 |
| S | 341242 | | ucugagcugcagguuccuua | 40 | |
| AS | 341213 | 3'UTR | cagggacucugucuccauuc | 41 | 52 |
| S | 341243 | | gaauggagacagaguccug | 42 | |
| AS | 341214 | 3'UTR | aacaaaauaagaaagccaug | 43 | 85 |
| S | 341244 | | cauggcuuucuuauuuuguu | 44 | |
| AS | 341215 | 3'UTR | gcuauucugugaauuaacaa | 45 | 71 |
| S | 341245 | | uuguuaauucacagaauagc | 46 | |
| AS | 341216 | 3'UTR | aguuugugcuauucugugaa | 47 | 85 |
| S | 341246 | | uucacagaauagcacaaacu | 48 | |
| AS | 341217 | 3'UTR | agaauggcuuugugcuuagu | 49 | 50 |
| S | 341247 | | acuaagcacaaagccauucu | 50 | |
| AS | 341218 | 3'UTR | uccaccugaaguucaccccg | 51 | 71 |
| S | 341248 | | cggggugaacuucaggugga | 52 | |
| AS | 341219 | 3'UTR | aaggaguaucugccagacgc | 53 | 65 |
| S | 341249 | | gcgucuggcagauacuccuu | 54 | |
| AS | 341220 | 3'UTR | uaaucacacagcaguggcaa | 55 | 72 |
| S | 341250 | | uugccacugcugugauua | 56 | |
| AS | 341221 | 3'UTR | gugccccgcggcucacuggg | 57 | 34 |
| S | 341251 | | cccagugagccgcggggcac | 58 | |
| AS | 341222 | 3'UTR | aaaggauuuaggccacugcc | 59 | 69 |
| S | 341252 | | ggcaguggccuaaauccuuu | 60 | |

TABLE 3-continued

Inhibition of human survivin mRNA levels by dsRNA oligomeric compounds with a 5'-phosphate cap

| Strand | ISIS # | REGION | SEQUENCE | SEQ ID NO | % INHIB |
|---|---|---|---|---|---|
| AS | 341223 | 3'UTR | acagcaucgagccaagucau | 61 | 59 |
| S | 341253 | | augacuuggcucgaugcugu | 62 | |
| AS | 341224 | 3'UTR | acagacacacggccugcagc | 63 | 20 |
| S | 341254 | | gcugcaggccgugugucugu | 64 | |
| AS | 341225 | 3'UTR | gaacgugacagaugugaagg | 65 | 39 |
| S | 341255 | | ccuucacaucugucacguuc | 66 | |
| AS | 341226 | 3'UTR | uccaucaucuuacgccagac | 67 | 73 |
| S | 341256 | | gucuggcguaagaugaugga | 68 | |
| AS | 341227 | 3'UTR | ggcgaaucaaauccaucauc | 69 | 59 |
| S | 341257 | | gaugauggauuugauucgcc | 70 | |
| AS | 341228 | 3'UTR | auccacccugcagcucuaug | 71 | 46 |
| S | 341258 | | cauagagcugcaggguggau | 72 | |
| AS | 341229 | 3'UTR | gccgagaugaccuccagagg | 73 | 61 |
| S | 341259 | | ccucuggaggucaucucggc | 74 | |

All dsRNA compounds except ISIS 341203, 341209, 341221, 341224 and 341225 demonstrated greater than 40% inhibition of survivin expression. These data suggest that at certain target sites, double-stranded compounds with a 5' phosphate display greater potentcy in inhibiting survivin expression (compare Tables 1 and 3).

Example 19

Comparison of siRNA Constructs Targeting the Same Site of Survivin mRNA: Dose Response In accordance with the present invention, the effects of altering the sequence of ISIS 339048 on inhibition of human survivin mRNA in HeLa cells was investigated. ISIS 343867 (5'-UUUGAAAAUGWUGAUCUCC-3': SEQ ID NO:81) is the antisense strand for a blunt-ended siRNA binding to the same site on the survivin mRNA as ISIS 339048, the difference being that ISIS 343867 is a 19-mer compound which lacks the 5'-terminal adenine residue of ISIS 339048. ISIS 341881 (UUUGAAAAUGUUGAUCUCCTT; SEQ ID NO:82) is the antisense strand for a canonical siRNA binding to the same site on the survivin mRNA as ISIS 339048, the difference being that ISIS 341881 contains a dTdT (deoxythymidine-deoxythymidine) at the 3'-terminus ("dTdT "overhang"). ISIS 343868 has the sequence 5'-GGAGAUCAACAUUUUCAAA-3' (SEQ ID NO:83), and is the sense strand corresponding to ISIS 343867. ISIS 341880 (SEQ ID NO: 84) is the sense strand corresponding to ISIS 341881. The constructs are shown in Table 4 with the antisense strand shown first followed by the sense strand, both in 5' to 3' orientation. The sequences of the survivin siRNA constructs are shown in Table 4, and the dose response results are shown in Table 5.

TABLE 4 siRNA constructs tested in dose response experiment in HeLa cells for inhibition of human survivin mRNA expression

| ISIS # | REGION | SEQUENCE | SEQ ID NO |
|---|---|---|---|
| 339048 | 3'UTR | auuugaaaauguugaucucc | 23 |
| 339078 | | ggagaucaacauuuucaaau | 24 |
| 343867 | 3'UTR | uuugaaaauguugaucucc | 81 |
| 343868 | | ggagaucaacauuuucaaa | 83 |
| 341881 | 3'UTR | uuugaaaauguugaucucctt | 82 |
| 341880 | | ggagaucaacauuuucaaatt | 84 |

TABLE 5

Inhibition of human survivin mRNA levels by siRNA oligomeric compounds targeting the same site of survivin mRNA: dose response
Percentage of Inhibition of survivin expression in HeLa cells

| | | Oligonucleotide Concentration (nM) | | | | | |
|---|---|---|---|---|---|---|---|
| Isis # | SEQ ID: | 0.02 | 0.08 | 0.4 | 2.0 | 10 | 50 |
| 339048_339078 | 23_24 | 27 | 31 | 58 | 70 | 83 | 88 |
| 343867_343868 | 81_83 | 20 | 44 | 66 | 82 | 90 | 92 |
| 341881_341880 | 82_84 | 38 | 52 | 70 | 81 | 88 | 91 |

As shown in Table 5, the compounds tested inhibit human survivin mRNA expression in HeLa cells in a dose-dependent manner. ISIS 343867 and ISIS 341881 are more effective at inhibition of survivin mRNA levels at all but the lowest doses, indicating that a blunt-ended 19-mer siRNA or a canonical 21-mer siRNA with a dTdT modification at the 3'-terminus may be advantageous modifications of ISIS 339048, the original blunt-ended 20-mer siRNA.

The IC50 values (nM) of these three compounds were as follows:

Blunt-ended siRNA (20-mer) 339048_339078, 0.28 nM;
Blunt-ended siRNA (19-mer) 343867_343868, 0.19 nM and
Canonical siRNA 341881_341880, 0.15 nM.

IC50 is defined as the concentration of oligomeric compound which results in 50% inhibition of mRNA (or protein) expression compared to an unreated control. From these data, the canonical siRNA and the blunt-ended siRNA (19-mer) both performed significantly better than the blunt-ended siRNA (20-mer).

Additional Blunt-ended Constructs Targeting Human Survivin: Modified Compounds:

A series of siRNA compounds targeting human survivin (GenBank accession no. NM_01168.1; SEQ ID NO: 14) were designed and are shown in Table 6 in the 5' to 3' orientation.

TABLE 6 siRNA compounds targeted to human survivin

| Strand | ISIS# | SEQUENCE | SEQ ID NO. |
|---|---|---|---|
| AS | 346272 | uuugaaaauguugaucuccu | 85 |
| AS | 346279 | uuugaaaauguugaucuccuu | 86 |
| AS | 346280 | uuugaaaauguugaucuccu | 85 |
| AS | 346281 | uuugaaaauguugaucucc | 81 |
| AS | 346282 | uuugaaaauguugaucuccuu | 86 |
| AS | 346283 | uuugaaaauguugaucuccu | 85 |
| AS | 346284 | uuugaaaauguugaucucc | 81 |
| S | 346286 | aggagaucaacauuuucaaa | 87 |
| S | 346287 | ggagaucaacauuuucaaa | 83 |
| S | 346289 | aggagaucaacauuuucaaa | 87 |
| S | 346290 | ggagaucaacauuuucaaa | 83 |
| AS | 346291 | uuugaaaauguugaucuccuu | 86 |
| AS | 346292 | uuugaaaauguugaucucc | 81 |
| S | 346294 | aggagaucaacauuuucaaa | 87 |
| S | 346295 | ggagaucaacauuuucaaa | 83 |
| AS | 346296 | uuugaaaauguugaucuccu | 85 |
| AS | 348310 | uuugaaaauguugaucuccuu | 86 |
| AS | 352505 | uuugaaaauguugaucucc | 81 |
| AS | 352506 | uuugaaaauguugaucucc | 81 |
| AS | 352507 | uuugaaaauguugaucucc | 81 |
| AS | 352508 | uuugaaaauguugaucucc | 81 |
| AS | 352509 | uuugaaaauguugaucucc | 81 |
| AS | 352510 | uuugaaaauguugaucucc | 81 |
| S | 352511 | ggagaucaacauuuucaaa | 83 |
| S | 352512 | ggagaucaacauuuucaaa | 83 |
| S | 352513 | ggagaucaacauuuucaaa | 83 |
| S | 352514 | ggagaucaacauuuucaaa | 83 |
| AS | 352515 | uuugaaaauguugaucucc | 81 |
| AS | 353537 | uuugaaaauguugaucucc | 81 |
| AS | 353538 | uuugaaaauguugaucucc | 81 |
| AS | 353539 | uuugaaaauguugaucucc | 81 |
| AS | 353540 | uuugaaaauguugaucucc | 81 |
| AS | 355710 | uuugaaaauguugaucucc | 81 |
| AS | 355711 | uuugaaaauguugaucucc | 81 |
| AS | 355712 | uuugaaaauguugaucucc | 81 |
| AS | 355713 | uuugaaaauguugaucucc | 81 |
| S | 355714 | ggagaucaacauuuucaaa | 83 |
| AS | 355715 | uuugaaaauguugaucucc | 81 |
| AS | 355716 | aauuugaaaauguugaucucc | 88 |

The modifications to the sequences in Table 6 are as follows:

ISIS 346272: all ribose, all P=O linkages

ISIS 346279-346281, 346286, 346287: all P=S linkages

ISIS 346282-346284, 346289 and 346290: alternating P=O/P=S linkages, beginning with P=O ISIS 346291, 346292, 346294, 346295 and 346296: alternating P=S/P=O linkages; beginning with P=S ISIS 348310: all ribose with P=O backbone ISIS 352505: 2'-O-methylribose at positions 5, 8, 11, 14 and 17-19. P=O backbone.

ISIS 352506: 2'-O-methylribose at positions 6, 7, 10, 1 and 17-19. P=O backbone.

ISIS 352507: 2'-O-methylribose at positions 1, 3, 5, 7, 9, 11, 13, 15, 17 and 19. P=O backbone.

ISIS 352508: 2'-MOE at positions 5, 8, 11 and 14; 2'-O-methyl at position 17-19. P=O backbone.

ISIS 352509: 2'-MOE at positions 4, 9 and 18. P=O backbone.

ISIS 352510: 2'-MOE at positions 1, 3, 5, 7, 9, 11, 13, 15, 17 and 19. P=O backbone.

ISIS 352511: 2'-MOE at positions 2, 4, 6, 8, 10, 12, 14, 16, and 18. P=O backbone.

ISIS 352512: 2'-O-methyl at every position, P=O backbone.

ISIS 352513: 2'-O-methyl at positions 2-18. P=O backbone.

ISIS 352514: 2'-MOE at positions 2, 4, 6, 8, 10, 12, 14, 16, and 18, P=O backbone.

ISIS 352515: 2'-O-methylribose at positions 15-19. P=O backbone.

ISIS 352516: P=S linker at linkages 1-7, P=O linker at linkages 8-18.

ISIS 353537: 4'-thioribose at positions 1-3 and 17-19, P=O backbone.

ISIS 353538: 4'thioribose at positions 3, 9, 12 and 17-19, P=O backbone.

ISIS 353539: 4'-thioribose at positions 1-3, 9 and 12; 2'-O-methylribose at positions 17-19, P=O backbone.

ISIS 353540: 4'-thioribose at positions 1-3; 2'-O-methyribose at positions 17-19, P=O backbone.

ISIS 355710: 2'-ara-fluoro-2'-deoxyribose at positions 1-5; 2'-O-methylribose at positions 15-19, P=O backbone.

ISIS 355711: 2'-ara-fluoro-2'-deoxyribose at positions 1-5, 8, 9 and 12-16; 2'-O-methylribose at positions 6, 7, 10, 11 and 17-19, P=O backbone.

ISIS 355712: LNA at positions 5, 8, 11, 14, 2'-O-methyl at 17-19. P=O backbone. ISIS 355713: alternating 2'-O-methylribose/2'-ara-fluoro-2'-deoxyribose, starting with 2'OMe at position 1. P=O backbone.

ISIS 355714: alternating 2'-O-methylribose/2'-ara-fluoro-2'-deoxyribose, starting with 2'-ara-fluoro at position 1. P=O backbone.

ISIS 355715: LNA at positions 4, 9, 18. P=O backbone.

ISIS 355716: LNA at positions 1, 2, 6, 11, 20. P=O backbone.

Example 20

Modulation of Human Survivin Expression by Single-stranded RNAi Compounds

A series of single-stranded olgometric compounds (asRNA) was evaluated for their ability to inhibit human survivin in human umbilical vein endothelial cells (HUVEC). Culture methods used for HUVEC are found, for example, at www.atcc.org.

The sequences of the asRNA oligomeric compounds are shown in Table 7. Target sites are indicated by the first (5' most) nucleotide number, as given in the sequence source reference (Genebank accession no. NM_001168.1, incorporated herein as SEQ ID NO: 14), to which the asRNA oligonucleotide binds.

All compounds in Table 7 are oligoribonucleotides, 20 nucleotides in length having phosphorothioate backbone linkages throughout and a terminal phosphate on the 5p end and all are depicted in the 5' to 3' direction.

Data were obtained by real-time quantitative PCR as described in other examples herein.

TABLE 7

Inhibition of human survivin mRNA levels by asRNA oligomeric compounds

| ISIS # | TARGET SITE | SEQUENCE | % INHIB | SEQ ID NO |
|---|---|---|---|---|
| 347423 | 456 | auccauggcagccagcugcu | 55 | 17 |
| 347424 | 512 | aacccuggaaguggugcagc | 69 | 19 |
| 347425 | 534 | aggcuggugccaccagggaa | 90 | 21 |
| 347426 | 568 | auuugaaaauguugaucucc | 60 | 23 |
| 347427 | 605 | agcacaguugaaacaucuaa | 54 | 25 |
| 347428 | 642 | agaagcaccucuggugccac | 60 | 27 |
| 347429 | 756 | ucccucacuucucaccuggu | 62 | 29 |
| 347430 | 780 | gcaaaagggacacugccuuc | 66 | 31 |
| 347431 | 815 | aggcucugcccacgcgaaca | 67 | 33 |
| 347432 | 846 | caacaugagguccagacaca | 66 | 35 |
| 347433 | 876 | aguccacacucaggacugug | 60 | 37 |
| 347434 | 914 | uaaggaaccugcagcucaga | 70 | 39 |
| 347435 | 1030 | cagggacucugucuccauuc | 44 | 41 |
| 347436 | 1070 | aacaaaauaagaaagccaug | 51 | 43 |
| 347437 | 978 | gcuauucugugaauuaacaa | 54 | 45 |
| 347438 | 1101 | aguuugugcuauucugugaa | 64 | 47 |
| 347439 | 1130 | agaauggcuuugugcuuagu | 62 | 49 |
| 347440 | 1165 | uccaccugaaguucaccccg | 57 | 51 |
| 347441 | 1212 | aaggaguaucugccagacgc | 66 | 53 |
| 347442 | 1232 | uaaucacacagcaguggcaa | 66 | 55 |
| 347443 | 1258 | gugccccgcggcucacuggg | 54 | 57 |
| 347444 | 1305 | aaaggauuuaggccacugcc | 60 | 59 |

TABLE 7-continued

Inhibition of human survivin mRNA levels by asRNA oligomeric compounds

| ISIS # | TARGET SITE | SEQUENCE | % INHIB | SEQ ID NO |
|---|---|---|---|---|
| 347445 | 1329 | acagcaucgagccaagucau | 53 | 61 |
| 347446 | 1366 | acagacacacggccugcagc | 52 | 63 |
| 347447 | 1394 | gaacgugacagaugugaagg | 47 | 65 |
| 347448 | 1487 | uccaucaucuuacgccagac | 58 | 67 |
| 347449 | 1498 | ggcgaaucaaauccaucauc | 51 | 69 |
| 347450 | 1529 | auccacccugcagcucuaug | 55 | 71 |
| 347451 | 1569 | gccgagaugaccuccagagg | 59 | 73 |

As shown in Table 7, all asRNA compounds demonstrated at least 44% inhibition of survivin expression.

Example 21

Inhibition of Survivin mRNA Expression in HeLa Cells Using dsRNA Constructs to Human Survivin Various dsRNA constructs were tested in HeLa cells as described above using the human survivin primer probe set (SEQ IDs 186-188) to determine the effect of PS substitution on the ISIS 343867 19-mer (SEQ ID NO:81), the 339048 20-mer (SEQ ID NO: 23), and the effect of 2'-O-methyl (2'-OMe), 2'-fluoro (2'-F), 2'-O-methoxyethyl (2'-MOE) and 4'-thio (4'-S) chemistries. The results are shown in Tables 8 and 9. The first ISIS number is the antisense strand, and the second ISIS number is the sense strand.

TABLE 8

Inhibition of human survivin mRNA levels by blunt-ended siRNA algometric compounds: effect of PS substitution on 19-mer

| | Length-backbone (antisense/sense) | ISIS # (antisense 5'-3'/sense 3'-5') | % INHIB | IC50 (nM) | SEQ ID NO |
|---|---|---|---|---|---|
| A | 19 PO/PO | 343867_343868 | 89 | 0.19 | 81_83 |
| B | 20 PO/PO | 339048_339078 | 77 | 1.8 | 23_24 |
| C | 19 PS/PS | 346281_346287 | 76 | 2-20 | 81_83 |
| D | 19 PS/PS-PO | 346281_346295 | 88 | 2-20 | 81_83 |
| E | 19 PS/PO-PS | 346281_346290 | 68 | 2-20 | 81_83 |
| F | 19 PO-PS/PS | 346284_346287 | 78 | 3.24 | 81_83 |
| G | 19 PS-PO/PS | 346292_346287 | 77 | 3.17 | 81_83 |
| H | 19 PS-PO/PS-PO | 346292_346295 | 88 | 1.6 | 81_83 |
| I | 19 PS-PO/PO-PS | 346292_346290 | 94 | 0.13 | 81_83 |
| J | 19 PO-PS/PO-PS | 346284_346290 | 91 | 2.0 | 81_83 |
| K | 19 PO-PS/PS-PO | 346284_346295 | 78 | 2.9 | 81_83 |

These data illustrate that the 19-mer blunt phosphodiester siRNA is more effective at inhibiting survivin expression and has a ten fold lower IC50 than its 20-mer counterpart (compare lines A and B). Furthermore, this increased potentcy, as measured by IC50, is lost when the backbone linkages are replaced by full phosphorothioate linkages. However, target reduction is maintained (compare lines A and C).

It is also shown that re-introduction of phosphodiester linkages in the antisense strand in an alternating register results in recovery of the efficacy, as measured by lowered IC50 values, but not to the level of the full P=O backbone (for example, compare lines D and H). Finally, alternating phosphodiester/phosphorothioate linkages in each strand when in opposing register (P=O in one strand opposite P=S in the other) had the greatest effect on IC50 values and expression levels, resulting in values that were better than the native optimal construct (compare lines I and A).

TABLE 9

Inhibition of human survivin mRNA levels by blunt-ended siRNA oligomeric compounds: effect of PS substitution on 20-mer

| Length-backbone (antisense/sense) | ISIS # (antisense 5'-3'/sense 3'-5') | % INHIB | IC50 (nM) | SEQ ID NO |
|---|---|---|---|---|
| A 19 PO/PO | 343867_343868 | 89 | 0.19 | 81_83 |
| B 20 PO/PO | 339048_339078 | 77 | 1.8 | 23_24 |
| C 20 PS/PS | 346280_346286 | 88 | 1.5 | 85_87 |
| D 20 PS/PS-PO | 346280_346294 | 84 | 1.7 | 85_87 |
| E 20 PS/PO-PS | 346280_346289 | 90 | 2.5 | 85_87 |
| F 20 PO-PS/PS | 346283_346286 | 77 | 3.9 | 85_87 |
| G 20 PS-PO/PS | 346296_346286 | 86 | 1.8 | 85_87 |
| H 20 PS-PO/PS-PO | 346296_346294 | 86 | 0.85 | 85_87 |
| I 20 PS-PO/PO-PS | 346296_346289 | 97 | 0.13 | 85_87 |
| J 20 PO-PS/PO-PS | 346283_346294 | 86 | 0.53 | 85_87 |
| K 20 PO-PS/PS-PO | 346283_346289 | 86 | 0.83 | 85_87 |

These data suggest that, in contrast to 19-mers, blunt-ended 20-mers have greater tolerance for phosphorothioate backbone modifications in both strands with IC50 values of 20-mer full P=S being comparable to 20-mer with full P=O in both strands (compare lines B and C). However, both 20 mer constructs fail to achieve the IC50 seen with the 19-mer (compare lines B and C to line A).

Surprisingly, the presence of alternating internucleoside linkeages in opposite register (P=O in one strand opposite P=S in the other) was able to reduce the IC50 to that seen with the 19-mer native P=O construct (compare lines I and A).

Effects of Chemical Modifications to the Sugar

A series of blunt-ended siRNAs were designed to investigate the effect of sugar modifications on the ability, of the double-stranded compounds to inhibit expression of human survivn mRNA. The study was performed in HeLa cells as described in other examples herein and the mRNA levels determined by RT-PCR.

The modifications to the compounds was as follows: ISIS 352511 comprises 2'-O-methyl modifications (underlined) at positions 2, 4, 6, 8, 10, 12, 14, 16 and 18.

ISIS 352512 comprises 2'-O-methyl modifications (underlined) at every 2'site.

ISIS 355714 comprises 2'-fluoro modifications (in BOLD) at positions 1, 3, 5, 7, 9, 11, 13, 15, 17 and 19; and 2'-O-methyl modifications at positions 2, 4, 6, 8, 10, 12, 14, 16 and 18.

ISIS 352514 comprises alternating 2'-MOE modifications positions 2, 4, 6, 8, 10, 12, 14, 16 and 18.

All other compounds were native RNA compounds. The results are shown in Table 10.

TABLE 10

Inhibition of human survivin mRNA levels by siRNA oligomeric compounds: effect of sugar modifications

| Compound | Sequence 5'→3' | SEQ ID NO: | IC50 (nM) | % INHIB |
|---|---|---|---|---|
| 343867 | uuugaaaauguugaucucc | 81 | 0.60 | 86 |
| 343868 | ggagaucaacauuuucaaa | 83 | | |
| 352507 | uuugaaaauguugaucucc | 81 | 0.24 | 89 |
| 352511 | ggagaucaacauuuucaaa | 83 | | |
| 352507 | uuugaaaauguugaucucc | 81 | 0.04 | 83 |
| 352512 | ggagaucaacauuuucaaa | 83 | | |
| 355713 | uuugaaaauguugaucucc | 81 | 0.06 | 92 |
| 355714 | ggagaucaacauuuucaaa | 83 | | |
| 352506 | uuugaaaauguugaucucc | 81 | 0.12 | 92 |
| 352514 | ggagaucaacauuuucaaa | 83 | | |
| 352507 | uuugaaaauguugaucucc | 81 | 0.21 | 89 |
| 352514 | ggagaucaacauuuucaaa | 83 | | |
| 352507 | uuugaaaauguugaucucc | 81 | 0.49 | 86 |
| 352514 | ggagaucaacauuuucaaa | 83 | | |

These data suggest that double stranded compounds containing alternating motifs of 2'F and 2'OMe are optimal constructs for the inhibition of human survivin expression.

Example 22

Dose Response Experiments in HeLa Cells Using dsRNA Constructs to Human Survivin In a dose-response experiment, HeLa cells were treated with 0.02, 0.2, 2.0 and 20.0 nM of the indicated dsRNA oligonucleotide mixed with 3 µg/mL LIPOFECTIN per 100 nM oligonucleotide as described by other examples herein. Untreated cells served as controls. Following 16 hours of treatment, RNA was prepared from cells for subsequent real-time PCR analysis.

Human survivin mRNA expression levels were quantitated by real-time PCR and gene target quantities were normalized using Ribogreen as described in other examples herein. Data are averages from two experiments are shown in Table 11. The Isis number of the antisense strand is shown first, followed by the Isis number of the sense strand (antisense_sense).

TABLE 11

Inhibition of human survivin mRNA levels by dsRNA oligomeric compounds: dose response
Percentage of Inhibition of survivin expression in HeLa cells

| | | Oligonucleotide Concentration | | | |
| --- | --- | --- | --- | --- | --- |
| Isis # | Seq ID Nos | 0.02 nM | 0.2 nM | 2.0 nM | 20.0 nM |
| 343867_343868 | 81_83 | 0 | 54 | 14 | 84 |
| 355710_343868 | 81_83 | 17 | 72 | 86 | 71 |
| 355711_343868 | 81_83 | 29 | 51 | 20 | 93 |
| 355712_343868 | 81_83 | 38 | 63 | 61 | 92 |
| 355715_343868 | 81_83 | 40 | 72 | 75 | 84 |
| 355716_343868 | 88_83 | 0 | 18 | 0 | 41 |
| 355713_355714 | 81_83 | 23 | 69 | 86 | 96 |
| 346280_352511 | 85_83 | 0 | 0 | 54 | 77 |
| 346280_352512 | 85_83 | 0 | 13 | 56 | 81 |
| 352507_346287 | 81_83 | 0 | 31 | 74 | 89 |
| 352505_352511 | 81_83 | 5 | 40 | 65 | 80 |
| 352505_352513 | 81_83 | 22 | 41 | 60 | 81 |
| 352507_352513 | 81_83 | 17 | 30 | 67 | 86 |
| 339048_339078 | 23_24 | N.D. | 27 | 58 | 78 |
| 339048_346286 | 23_87 | N.D. | 29 | 67 | 82 |
| 339048_346289 | 23_87 | N.D. | 18 | 55 | 82 |
| 339048_346294 | 23_87 | N.D. | 39 | 65 | 85 |
| 346280_339078 | 85_24 | N.D. | 2 | 39 | 71 |
| 346283_339078 | 85_24 | N.D. | 41 | 70 | 83 |
| 346296_339078 | 85_24 | N.D. | 38 | 69 | 86 |
| 343867_343868 | 81_83 | 19 | 60 | 78 | 90 |
| 353537_343868 | 81_83 | 25 | 49 | 68 | 81 |
| 353538_343868 | 81_83 | 17 | 41 | 72 | 82 |
| 353539_343868 | 81_83 | 19 | 48 | 76 | 88 |
| 353540_343868 | 81_83 | 21 | 51 | 77 | 90 |

As shown in Table 11, many of the dsRNA compounds inhibited human survivin mRNA expression in HeLa cells in a dose-dependent manner.

Example 23

Dose Response Experiments in HeLa Cells Using dsRNA Constructs to Human Survivin In a dose-response experiment, HeLa cells were treated with 0.014, 0.04, 0.12, 0.37, 1.11, 3.33, 10 and 30 nM of the indicated dsRNA oligonucleotide mixed with 3 μg/mL LIPOFECTIN per 100 nM oligonucleotide as described by other examples herein. Untreated cells served as controls. Following 16 hours of treatment, RNA was prepared from cells for subsequent real-time PCR analysis.

Human survivin mRNA expression levels were quantitated by real-time PCR and gene target quantities were normalized using Ribogreen as described in other examples herein. Data are averages from two experiments are shown in Table 12. The Isis number of the antisense strand is shown first, followed by the Isis number of the sense strand (antisense_sense).

TABLE 12

Inhibition of human survivin mRNA levels by dsRNA oligomeric compounds: dose response
Percentage of Inhibition of survivin expression in HeLa cells

| | | Oligonucleotide Concentration | | | | | | | |
| --- | --- | --- | --- | --- | --- | --- | --- | --- | --- |
| Isis # | Seq ID No. | 0.014 nM | 0.04 nM | 0.12 nM | 0.37 nM | 1.11 nM | 3.33 nM | 10 nM | 30 nM |
| 353537_343868 | 81_83 | 0 | 0 | 0 | 15 | 17 | 48 | 77 | 82 |
| 353538_343868 | 81_83 | 3 | 25 | 22 | 37 | 43 | 70 | 83 | 82 |
| 353539_343868 | 81_83 | 0 | 20 | 10 | 38 | 72 | 80 | 90 | 91 |
| 352507_352511 | 81_83 | 12 | 45 | 25 | 30 | 29 | 59 | 78 | 80 |
| 352507_352512 | 81_83 | 0 | 45 | 8 | 25 | 57 | 65 | 73 | 83 |
| 353540_343868 | 81_83 | 0 | 22 | 0 | 24 | 60 | 59 | 82 | 81 |
| 352506_352514 | 81_83 | 22 | 25 | 25 | 42 | 45 | 80 | 88 | 90 |
| 352507_352514 | 81_83 | 14 | 12 | 10 | 41 | 57 | 77 | 84 | 90 |
| 355713_355714 | 81_83 | 30 | 23 | 40 | 56 | 65 | 87 | 91 | 92 |

As shown in Table 12, most of the dsRNA compounds inhibited human survivin mRNA expression in HeLa cells in a dose-dependent manner.

Example 24

Dose-dependent Inhibition of Survivin mRNA Expression in U-87 MG Cells

Double-stranded compounds were tested for their ability to inhibit expression of human survivin mRNA in U-87 MG cells using the methods described above. Various dsRNA constructs targeting human survivin were tested at concentrations of 0.0019 nM, 0.0096 nM, 0.048 nM, 0.24 nM, 1.2 nM, 6.0 nM, 30.0 nM and 150.0 nM. The results are summarized in Table 13. The Isis number of the antisense strand is shown first, followed by the Isis number of the sense strand (antisense_sense).

TABLE 13

Dose dependent inhibition of human survivin mRNA expression with dsRNA compounds
Percentage of Inhibition of survivin expression in U-87 MG cells

| Isis # | Seq ID No. | Oligonucleotide Concentration (nM) | | | | | | | |
|---|---|---|---|---|---|---|---|---|---|
| | | 0.0019 | 0.0096 | 0.048 | 0.24 | 1.2 | 6.0 | 30 | 150 |
| 352506_352514 | 81_83 | 7 | 9 | 15 | 40 | 60 | 74 | 82 | 85 |
| 352507_352514 | 81_83 | 0 | 0 | 10 | 30 | 47 | 65 | 79 | 84 |
| 355713_355714 | 81_83 | 21 | 17 | 34 | 48 | 70 | 82 | 85 | 86 |
| 353537_343868 | 81_83 | 7 | 12 | 9 | 22 | 44 | 75 | 69 | 77 |
| 353538_343868 | 81_83 | 8 | 10 | 16 | 25 | 50 | 65 | 77 | 79 |
| 353539_343868 | 81_83 | 5 | 12 | 17 | 25 | 57 | 65 | 80 | 82 |
| 352507_352511 | 81_83 | 12 | 15 | 22 | 28 | 60 | 71 | 83 | 90 |
| 352507_352512 | 81_83 | 17 | 3 | 18 | 27 | 52 | 66 | 82 | 85 |
| 353540_343868 | 81_83 | 16 | 22 | 33 | 44 | 58 | 73 | 83 | 86 |
| 343867_343868 | 81_83 | 15 | 10 | 20 | 25 | 46 | 68 | 78 | 83 |
| 346280_346286 | 85_87 | 2 | 0 | 0 | 4 | 20 | 45 | 75 | 70 |
| 346296_346289 | 85_87 | 6 | 2 | 1 | 17 | 35 | 62 | 82 | 85 |

As shown in Table 13, most of the dsRNA compounds inhibited human survivin mRNA expression in U-87 MG cells in a dose-dependent manner.

Example 25

Inhibition of Survivin by Canonical siRNA Oligonucleotides

A series of canonical siRNAs were designed to target human survivin. Each of the dsRNA sequences specific to survivin and depicted below contain two deoxythymidine nucleotides at the 3' terminal end of each strand of the RNA oligonucleotide duplex (not shown). Synthesis, duplex formation and purification of gene-specific siRNAs were performed by Dharmacon Research Inc. In the Table, "Position" refers to the position of the gene to which the antisense strand of the dsRNA binds. Each sequence in the table is listed such that the antisense strand (top strand) is written in 5' to 3' direction; its complementary sense strand (bottom strand) is also written in the 5' to 3' direction.

TABLE 14

Canonical siRNA oligonucleotides designed to target to human survivin

| Compound | Strand | SEQ ID NO | Position | Sequence (5'→3') |
|---|---|---|---|---|
| U1 | AS | 89 | 015-033 | ucgcgggacccguuggcag |
| | S | 90 | | cugccaacgggucccgcga |
| U2 | AS | 91 | 094-112 | ggaccaccgcaucucuaca |
| | S | 92 | | uguagagaugcggugucc |
| U3 | AS | 93 | 121-139 | cuggcccuucuuggagggc |
| | S | 94 | | gcccuccaagaagggccag |
| U4 | AS | 95 | 173-191 | ggcuucauccacugcccca |
| | S | 96 | | uggggcaguggaugaagcc |

TABLE 14-continued

Canonical siRNA oligonucleotides designed to target to human survivin

| Compound | Strand | SEQ ID NO | Position | Sequence (5'→3') |
|---|---|---|---|---|
| U5 | AS | 97 | 199-217 | cgagccagacuuggcccag |
| | S | 98 | | cugggccaagucuggcucg |
| U6 | AS | 99 | 235-253 | ggagcuggaaggcugggag |
| | S | 100 | | cucccagccuuccagcucc |
| U7 | AS | 101 | 283-301 | aaagcauucguccgguugc |
| | S | 102 | | gcaaccggacgaaugcuuu |
| U8 | AS | 103 | 278-296 | cauaaaaagcauucguccg |
| | S | 104 | | cggacgaaugcuuuuuaug |
| U9 | AS | 105 | 332-350 | gaauuaacccuuggugaau |
| | S | 106 | | auucaccaagggguuaauuc |

TABLE 14-continued

Canonical siRNA oligonucleotides designed to target to human survivin

| Compound | Strand | SEQ ID NO | Position | Sequence (5'→3') |
|---|---|---|---|---|
| U10 | AS | 107 | 358-376 | acuggacagagaaagagcc |
|  | S | 108 |  | ggcucuuucucuguccagu |
| U11 | AS | 109 | 368-386 | gaaagagccaagaacaaaa |
|  | S | 110 |  | uuuuguucuuggcucuuuc |
| U12 | AS | 111 | 372-390 | gagccaagaacaaaauugc |
|  | S | 112 |  | gcaauuuuguucuuggcuc |
| U13 | AS | 113 | 387-405 | uugcaaaggaaaccaacaa |
|  | S | 114 |  | uuguugguuccuuugcaa |
| U14 | AS | 115 | 399-417 | ccaacaauaagaagaaaga |
|  | S | 116 |  | ucuuucuucuuauuguugg |
| U15 | AS | 117 | 409-427 | gaagaaagaauuugaggaa |
|  | S | 118 |  | uuccucaaauucuuucuuc |
| U16 | AS | 119 | 429-447 | cugcgaagaaagugcgccg |
|  | S | 120 |  | cggcgcacuuucuucgcag |
| U17 | AS | 121 | 586-604 | ggagaucaacauuuucaaa |
|  | S | 122 |  | uuugaaaauguugaucucc |
| U18 | AS | 123 | 618-636 | cugugcuccuguuuugucu |
|  | S | 124 |  | agacaaaacaggagcacag |
| U19 | AS | 125 | 642-660 | guggcaccagaggugcuuc |
|  | S | 126 |  | gaagcaccucuggugcaac |
| U20 | AS | 127 | 780-798 | gaaggcaguguccccuuuug |
|  | S | 128 |  | caaaagggacacugccuuc |
| U21 | AS | 129 | 1005-1023 | gaugcaugacuugugugug |
|  | S | 130 |  | cacacacaagucaugcauc |
| U22 | AS | 131 | 1033-1051 | uggagacagagucccuggc |
|  | S | 132 |  | gccagggacucugucucca |
| U23 | AS | 133 | 1070-1088 | cauggcuuucuuauuuugu |
|  | S | 134 |  | acaaaauaagaaagccaug |
| U24 | AS | 135 | 1094-1112 | uuguuaauucacagaauag |
|  | S | 136 |  | cuauucgugaauuaacaa |
| U25 | AS | 137 | 1119-1137 | cuacaauuaaaacuaagca |
|  | S | 138 |  | ugcuuaguuuuaauuguag |
| U26 | AS | 139 | 1030-1048 | acuaagcacaaagccauuc |
|  | S | 140 |  | gaauggcuuugugcuuagu |
| U27 | AS | 141 | 1198-1216 | uagagugauaggaagcguc |
|  | S | 142 |  | gacgcuuccuaucacucua |
| U28 | AS | 143 | 1212-1230 | gcgucuggcagauaucccu |
|  | S | 144 |  | agggauaucugccagacgc |
| U29 | AS | 145 | 1303-1321 | aaggcaguggccuaaaucc |
|  | S | 146 |  | ggauuuaggccacugccuu |
| U30 | AS | 147 | 1305-1323 | ggcaguggccuaaauccuu |
|  | S | 148 |  | aaggauuuaggccacugcc |
| U31 | AS | 149 | 1329-1347 | augacuuggcucgaugcug |
|  | S | 150 |  | cagcaucgagccaagucau |
| U32 | AS | 151 | 1394-1412 | ccuucacaucugucacguu |
|  | S | 152 |  | aacgugacagaugugaagg |
| U33 | AS | 153 | 1101-1119 | uucacagaauagcacaaac |
|  | S | 154 |  | guuugugcuauucugugaa |
| U34 | AS | 155 | 143-121 | gccugcaccccggagcgga |
|  | S | 156 |  | uccgcuccggggugcaggc |
| U35 | AS | 157 | 078-096 | cauaaaaagcauucguccg |
|  | S | 158 |  | cggacgaaugcuuuuuaug |
| U36 | AS | 159 | 456-474 | agcagcuggcugccaugga |
|  | S | 160 |  | uccauggcagccagcugcu |
| U37 | AS | 161 | 512-530 | gcugcaccacuuccagggu |
|  | S | 162 |  | acccuggaaguggugcagc |
| U38 | AS | 163 | 534-552 | uucccguggccaccagcc |
|  | S | 164 |  | ggcugguggcaccagggaa |
| U39 | AS | 165 | 559-577 | ugggccccuuagcaauguc |
|  | S | 166 |  | gacauugcuaaggggccca |
| U40 | AS | 167 | 580-598 | aggaaaggagaucaacauu |
|  | S | 168 |  | aauguugaucuccuuuccu |
| U41 | AS | 169 | 605-623 | uuagauguuucaacugugc |
|  | S | 170 |  | gcacaguugaaacaucuaa |
| U42 | AS | 171 | 688-706 | caguggcugcuucucucuc |
|  | S | 172 |  | gagagagaagcagccacug |
| U43 | AS | 173 | 726-744 | cucauuuugcuguuuuga |
|  | S | 174 |  | ucaaaacagcaaaaaugag |
| U44 | AS | 175 | 815-833 | uguucgcgugggcagagcc |
|  | S | 176 |  | ggcucugcccacgcgaaca |
| U45 | AS | 177 | 846-864 | ugugucuggaccucauguu |
|  | S | 178 |  | aacaugagguccagacaca |
| U46 | AS | 179 | 876-894 | cacaguccugaguguggac |
|  | S | 180 |  | guccacacucaggacugug |
| U47 | AS | 181 | 890-908 | uggacuuggcaggugccug |
|  | S | 182 |  | caggcaccugccaagucca |
| U48 | AS | 183 | 914-932 | ucugagcugcagguuccuu |
|  | S | 184 |  | aaggaaccugcagcucaga |
| U49 | AS | 185 | 946-964 | gugccuccucagaggacag |
|  | S | 186 |  | cuguccucugaggaggcac |
| U50 | AS | 187 | 972-990 | guuguuguguuuuuuuguu |
|  | S | 188 |  | aacaaaaaaacacaacaac |
| U51 | AS | 189 | 1130-1148 | acuaagcacaaagccauuc |
|  | S | 190 |  | gaauggcuuugugcuuagu |
| U52 | AS | 191 | 1142-1160 | gccauucuaagucauuggg |
|  | S | 192 |  | cccaaugacuuagaauggc |
| U53 | AS | 193 | 1152-1170 | gucauuggggaaacgggu |
|  | S | 194 |  | accccguuucccaaugac |
| U54 | AS | 195 | 1165-1183 | cggggugaacuucaggugg |
|  | S | 196 |  | ccaccugaaguucacccg |
| U55 | AS | 197 | 067-085 | gccccugccuggcagccc |
|  | S | 198 |  | gggcugccaggcaggggc |
| U57 | AS | 199 | 1435-1453 | guccgcccaggucccgcu |
|  | S | 200 |  | agcggggaccugggcggac |
| U58 | AS | 201 | 1487-1505 | gucuggcguaagaugaugg |
|  | S | 202 |  | ccaucaucuuacgccagac |

TABLE 14-continued

Canonical siRNA oligonucleotides designed to target to human survivin

| Compound | Strand | SEQ ID NO | Position | Sequence (5'→3') |
|---|---|---|---|---|
| U59 | AS | 203 | 1498-1516 | gaugauggauuugauucgc |
|  | S | 204 |  | gcgaaucaaauccaucauc |
| U60 | AS | 205 | 1569-1587 | ccucuggaggucaucucgg |
|  | S | 206 |  | ccgagaugaccuccagagg |
| U61 | AS | 207 | 008-026 | auuugaaucgcgggacccg |
|  | S | 208 |  | cgggucccgcgauucaaau |
| U62 | AS | 209 | 046-064 | cggcaugggugccccgacg |
|  | S | 210 |  | cgucggggcacccaugccg |
| U63 | AS | 211 | 211-229 | ggcccaguguuucuucugc |
|  | S | 212 |  | gcagaagaaacacugggcc |
| U64 | AS | 213 | 667-685 | ugcagcgggugcugcuggu |
|  | S | 214 |  | accagcagcacccgcugca |
| U65 | AS | 215 | 756-774 | accaggugagaagugaggg |
|  | S | 216 |  | cccucacuucucaccuggu |
| U66 | AS | 217 | 1232-1250 | uugccacugcugugugauu |
|  | S | 218 |  | aaucacacagcaguggcaa |
| U67 | AS | 219 | 1281-1299 | cuggccgcuccucccucag |
|  | S | 220 |  | cugagggaggagcggccag |
| U68 | AS | 221 | 1258-1276 | cccagugagccgcggggca |
|  | S | 222 |  | ugccccgcggcucacuggg |
| U69 | AS | 223 | 1366-1384 | gcugcaggccgugugucug |
|  | S | 224 |  | cagacacacggccugcagc |
| U70 | AS | 225 | 1529-1547 | cauagagcugcagggugga |
|  | S | 226 |  | uccacccugcagcucuaug |
| U71 | AS | 227 | 1547-1565 | auuguuacagcuucgcugg |
|  | S | 228 |  | ccagcgaagcuguaacaau |
| U72 | AS | 229 | 1597-1615 | agaaauaaaaagccuguca |
|  | S | 230 |  | ugacaggcuuuuuauuucu |

Compounds U17, U20, U23, U36, U48, and U54, when tested for inhibition of survivin mRNA using the above-described RT-PCR and quantitative Western blot assays, exhibit an $IC_{50}$ of less than 100 nM.

Compound U17 exhibits potent activity in both quantitative RT-PCR analysis and Western blot analysis, and is therefore especially preferred for the indications described herein.

Example 26

IC50 Values of Additional Double-stranded Compounds Targeting Human Survivin Tables 15 and 16 summarize IC50 values using various dsRNAs which were performed using the methods described herein. The constructs tested comprise the antisense strand in the 5'-3' orientation, and the sense strand in the 5' to 3' orientation, In Table 15, "D" is dose response (mRNA levels) and "W" is Western blot. All internucleoside linkages are phosphodiester unless otherwise noted by a lowercase "s" indicating a phosphorothioate linkage.

TABLE 15

IC50 data for dsRNA constructs targeted to human survivin

| siRNA Construct (antisense_sense) | Antisense Strand (5'-3')<br>Sense Strand (5'-3') | Assay/cell line | IC50 | SEQ ID NOs |
|---|---|---|---|---|
| 339044_339074 | AGGGCUGCCAGGCAGGGGC<br>GCCCCCUGCCUGGCAGCCCU | W/HeLa | 5.3 | 15_16 |
| 339045_339075 | AUCCAUGGCAGCCAGCUGCU<br>AGCAGCUGGCUGCCAUGGAU | W/HeLa | 5.5 | 17_18 |
| 339045_339075 | AUCCAUGGCAGCCAGCUGCU<br>AGCAGCUGGCUGCCAUGGAU | D/U-87 MG | .68 | 17_18 |
| 339045_339075 | AUCCAUGGCAGCCAGCUGCU<br>AGCAGCUGGCUGCCAUGGAU | D/HeLa | 3.3 | 17_18 |
| 339046_339076 | AACCCUGGAAGUGGUGCAGC<br>GCUGCACCACUUCCAGGGUU | W/HeLa | 3.5 | 19_20 |
| 339047_339077 | AGGCUGGUGGCACCAGGGAA<br>UUCCCUGGUGCCACCAGCCU | W/HeLa | 99.2 | 21_22 |
| 339048_339078 | AUUUGAAAAUGUUGAUCUCC<br>GGAGAUCAACAUUUUCAAAU | W/HeLa | 3.97 | 23_24 |
| 339048_339078 | AUUUGAAAAUGUUGAUCUCC<br>GGAGAUCAACAUUUUCAAAU | D/HeLa | 0.42 | 23_24 |
| 339048_339078 | AUUUGAAAAUGUUGAUCUCC<br>GGAGAUCAACAUUUUCAAAU | D/HeLa | 0.28 | 23_24 |

TABLE 15-continued

IC50 data for dsRNA constructs targeted to human survivin

| siRNA Construct (antisense_sense) | Antisense Strand (5'-3') Sense Strand (5'-3') | Assay/ cell line | IC50 | SEQ ID NOs |
|---|---|---|---|---|
| 339048_339078 | AUUUGAAAAUGUUGAUCUCC GGAGAUCAACAUUUUCAAAU | D/HeLa | 0.28 | 23_24 |
| 339048_339078 | AUUUGAAAAUGUUGAUCUCC GGAGAUCAACAUUUUCAAAU | D/U-87 MG | 0.34 | 23_24 |
| 339048_339078 | AUUUGAAAAUGUUGAUCUCC GGAGAUCAACAUUUUCAAAU | D/HeLa | 1.24 | 23_24 |
| 339048_346286 | AUUUGAAAAUGUUGAUCUCC AsGsGsAsGsAsUsCsAsAsCsAsUsUsUs UsCsAsAsA | D/HeLa | 0.40 | 23_40 |
| 339048_346289 | AUUUGAAAAUGUUGAUCUCC AGsGAsGAsUCsAAsCAsUUsUUsCAs AA | D/HeLa | 0.96 | 23_46 |
| 339048_346294 | AUUUGAAAAUGUUGAUCUCC AsGGsAGsAUsCAsACsAUsUUsUCsA AsA | D/HeLa | 0.24 | 23_87 |
| 339049_339079 | AGCACAGUUGAAACAUCUAA UUAGAUGUUUCAACUGUGCU | W/HeLa | 6.12 | 25_26 |
| 339050_339080 | AGAAGCACCUCUGGUGCCAC GUGGCACCAGAGGUGCUUCU | W/HeLa | 100 | 27_28 |
| 339051_339081 | UCCCUCACUUCUCACCUGGU ACCAGGUGAGAAGUGAGGGA | W/HeLa | 100 | 29_30 |
| 339052_339082 | GCAAAAGGGACACUGCCUUC GAAGGCAGUGUCCCUUUUGC | W/HeLa | 100 | 31_32 |
| 339052_339082 | GCAAAAGGGACACUGCCUUC GAAGGCAGUGUCCCUUUUGC | D/U-87 MG | 1.15 | 31_32 |
| 339052_339082 | GCAAAAGGGACACUGCCUUC GAAGGCAGUGUCCCUUUUGC | D/HeLa | 2.41 | 31_32 |
| 339053_339083 | AGGCUCUGCCCACGCGAACA UGUUCGCGUGGGCAGAGCCU | W/HeLa | 99.6 | 33_34 |
| 339054_339084 | CAACAUGAGGUCCAGACACA UGUGUCUGGACCUCAUGUUG | W/HeLa | 100 | 35_36 |
| 339055_339085 | AGUCCACACUCAGGACUGUG CACAGUCCUGAGUGUGGACU | W/HeLa | 100 | 37_38 |
| 339056_339086 | UAAGGAACCUGCAGCUCAGA UCUGAGCUGCAGGUUCCUUA | W/HeLa | 7.5 | 39_40 |
| 339056_339086 | UAAGGAACCUGCAGCUCAGA UCUGAGCUGCAGGUUCCUUA | D/U-87 MG | 0.51 | 39_40 |
| 339056_339086 | UAAGGAACCUGCAGCUCAGA UCUGAGCUGCAGGUUCCUUA | D/HeLa | 1.72 | 39_40 |
| 339057_339087 | CAGGGACUCUGUCUCCAUUC GAAUGGAGACAGAGUCCCUG | W/HeLa | 100 | 41_42 |
| 339058_339088 | AACAAAAUAAGAAAGCCAUG CAUGGCUUUCUUAUUUUGUU | W/HeLa | 7.23 | 43_44 |
| 339058_339088 | AACAAAAUAAGAAAGCCAUG CAUGGCUUUCUUAUUUUGUU | D/HeLa | 2.96 | 43_44 |
| 339059_339089 | GCUAUUCUGUGAAUUAACAA UUGUUAAUUCACAGAAUAGC | W/HeLa | 6.41 | 45_46 |
| 339060_339090 | AGUUUGUGCUAUUCUGUGAA UUCACAGAAUAGCACAAACU | W/HeLa | 4.43 | 47_48 |

TABLE 15-continued

IC50 data for dsRNA constructs targeted to human survivin

| siRNA Construct (antisense_sense) | Antisense Strand (5'-3') Sense Strand (5'-3') | Assay/ cell line | IC50 | SEQ ID NOs |
|---|---|---|---|---|
| 339060_339090 | AGUUUGUGCUAUUCUGUGAA UUCACAGAAUAGCACAAACU | D/HeLa | 3.38 | 47_48 |
| 339061_339091 | AGAAUGGCUUUGUGCUUAGU ACUAAGCACAAAGCCAUUCU | W/HeLa | 100 | 48_50 |
| 339062_339092 | UCCACCUGAAGUUCACCCCG CGGGGUGAACUUCAGGUGGA | W/HeLa | 65.2 | 51_52 |
| 339062_339092 | UCCACCUGAAGUUCACCCCG CGGGGUGAACUUCAGGUGGA | D/HeLa | 1.80 | 51_52 |
| 339063_339093 | AAGGAGUAUCUGCCAGACGC GCGUCUGGCAGAUACUCCUU | W/HeLa | 6.2 | 53_54 |
| 339064_339094 | UAAUCACACAGCAGUGGCAA UUGCCACUGCUGUGUGAUUA | W/HeLa | 5.45 | 55_56 |
| 339065_339095 | GUGCCCCGCGGCUCACUGGG CCCAGUGAGCCGCGGGGCAC | W/HeLa | 94.2 | 57_58 |
| 339066_339096 | AAAGGAUUUAGGCCACUGCC GGCAGUGGCCUAAAUCCUUU | W/HeLa | 1.72 | 59_60 |

TABLE 16

IC50 values for dsRNA to human survivin

| dsRNA (antisense_sense) | SEQ ID NOS: | IC50 (nM) mRNA |
|---|---|---|
| 352505_343868 | 81_83 | 0.88 |
| 352505_346287 | 81_83 | 2.2 |
| 352505_352512 | 81_83 | 0.39 |
| 352505_352514 | 81_83 | 1.3 |
| 352506_346287 | 81_83 | 0.23 |
| 352506_352511 | 81_83 | 0.11 |
| 352506_352512 | 81_83 | 0.23 |
| 352506_352513 | 81_83 | 0.43 |
| 352507_346287 | 81_83 | 0.8 |
| 352515_343868 | 81_83 | 0.29 |
| 353537_352512 | 81_83 | 1.5 |
| 353537_352513 | 81_83 | 1.5 |
| 353537_352514 | 81_83 | 1.6 |
| 355710_343868 | 81_83 | 0.1 |
| 346280_352514 | 85_83 | N.D. |
| 343867_346295 | 81_83 | N.D. |
| 346280_339078 | 85_24 | N.D. |
| 346280_343868 | 85_83 | N.D. |
| 346281_343868 | 81_83 | N.D. |
| 339048_346286 | 23_87 | N.D. |
| 343867_346287 | 81_83 | N.D. |
| 353537_343868 | 81_83 | 0.18 |
| 353538_343868 | 81_83 | 0.16 |
| 353539_343868 | 81_83 | 0.13 |
| 353540_343868 | 81_83 | 0.11 |
| 346284_346287 | 81_83 | 3.24 |
| 352506_352514 | 81_83 | 0.12 |
| 352507_352512 | 81_83 | 0.04 |
| 352507_352514 | 81_83 | 0.21 |
| 352507_352511 | 81_83 | 0.24 |
| 352506_343868 | 81_83 | 0.16 |
| 355713_355714 | 81_83 | 0.06 |

Example 27

Measurement of Antitumor Activity in a Human Glioblastoma Xenograft Tumor Model

One or more of the oligomeric compounds described herein, including dsRNA compounds, is tested for antitumor activity in an animal model known in the art. Two such animal models are (1) U-87MG human glioblastoma xenograft tumor model (Kiaris H, Schally A V, Varga J L, Antagonists of growth hormone-releasing hormone inhibit the growth of U-87MG human glioblastoma in nude mice Neoplasia. 2000 May-June; 2(3):242-50), and (2) a YUSAC-2 human melanoma xenograft tumor model (Grossman D, Kim P J, Schechner J S, Altieri D C, Inhibition of melanoma tumor growth in vivo by survivin targeting. Proc Natl Acad Sci USA. 2001 Jan. 16; 98(2):635-40). A total of 10 CD1 nu/nu (Charles River) mice is used for each group. For implantation, tumor cells are trypsinized, washed in PBS and resuspended in PBS at $6 \times 10^7$ cells/ml (U-87MG) and at $4 \times 10^7$ cells/ml (YUSAC-2) in DMEM. Just before implantation, animals are irradiated (450 TBI) and cells are mixed in Matrigel (1:1). A total of $6 \times 10^6$ (U-87MG) and at $4 \times 10^6$ (YUSAC-2) tumor cells in a 0.2 ml volume are injected subcutaneously (s.c.) in the left rear flank. Treatment with the test oligomeric compound (dissolved in 0.9% NaCl, injection grade), or a mismatch control oligonucleotide (dissolved in 0.9% NaCl) or vehicle (0.9% NaCl) is started 3 days post tumor cell implantation. Compounds are administered intraperitoneally (i.p.) and intravenously (i.v.) for U-87MG and YUSAC-2 studies respectively in a 0.2 ml volume every other day for a total of about 12 doses for the U-87MG study and about 13 doses for the YUSAC-2 study. Tumor length and width are measured twice a week, and tumor volume is calculated using the formula: Tumor volume=(L×W2)×0.536. Tumor volumes are plotted against days post tumor implantation for each treatment group.

Treatment with one or more of the oligomeric compounds delays human glioblastoma and melanoma tumor growth when compared with tumor bearing animals treated with vehicle or 25 mg/kg mismatch control oligonucleotide.

Example 28

Stability of Alternating 2'-O-methyl/2'-fluoro siRNA Constructs in Mouse Plasma

Intact duplex RNA was analyzed from diluted mouse-plasma using an extraction and capillary electrophoresis method similar to those previously described (Leeds, J. M., et al., 1996, *Anal. Biochem.*, 235, 36-43; Geary, R. S., et al., 1999, *Anal. Biochem.*, 274, 241-248. Heparin-treated mouse plasma, from 3-6 month old female Balb/c mice (Charles River Labs) was thawed from −80° C. and diluted to 25% (v/v) with phosphate buffered saline (140 mM NaCl, 3 mM KCl, 2 mM potassium phosphate, 10 mM sodium phosphate). Approximately 10 nmol of pre-annealed siRNA, at a concentration of 100 µM, was added to the 25% plasma and incubated at 37° C. for 0, 15, 30, 45, 60, 120, 180, 240, 360, and 420 minutes. Aliquots were removed at the indicated time, treated with EDTA to a final concentration of 2 mM, and placed on ice at 0° C. until analyzed by capillary gel electrophoresis (Beckman P/ACE MDQ-UV with eCap DNA Capillary tube). The area of the siRNA duplex peak was measured and used to calculate the percent of intact siRNA remaining. Adenosine triphosphate (ATP) was added at a concentration of 2.5 mM to each injection as an internal calibration standard. A zero time point was taken by diluting siRNA in phosphate buffered saline followed by capillary electrophoresis. Percent intact siRNA was plotted against time, allowing the calculation of a pseudo first-order half-life. Results are shown in Table 18.

TABLE 17

Stability of alternating 2'-O-methyl/2'-fluoro blunt siRNA constructs in mouse plasma

| Construct | SEQ ID | Stability (t ½ in hours) |
|---|---|---|
| 353537_343868 | 81_83 | 3 |
| 355713_355714 | 81_83 | >4 |

ISIS 353538, the antisense strand contains 4' thio modifications at positions 3, 8, 11, 17-19 and is paired with a sense RNA strand which is unmodified.

ISIS 355713, the antisense strand contains alternating 2'Omethy/2'F modifications to the sugar and is paired with a sense strand having alternating 2'F/2'Omethyl modifications. The alternate modifications are in opposing register with the antisense strand being modified with 2'Ome at position 1 while the sense strand is modified with 2'F at position 1. It is evident that the alternating 2'-O-methyl/2'-fluoro construct remains relatively unchanged and is stable in serum.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

The invention claimed is:

1. A compound comprising a chemically modified or unmodified double-stranded nucleic acid compound 19-23 nucleotides in length,
   wherein a first strand of said compound has at least 19 contiguous nucleotides of nucleotide sequence SEQ ID NO: 81, and
   wherein a second strand of said compound is 100% complementary to said first strand.

2. The compound of claim 1, which is blunt-ended or canonical.

3. The compound of claim 1, comprising at least one chemical modification to a sugar, nucleobase, or internucleoside linkage.

4. The compound of claim 3, wherein each chemical modification to said sugar is a 2' modification.

5. The compound of claim 4, wherein each 2' sugar modification is independently selected from the group consisting of 2'-O-(2-methoxyethyl)(2'-MOE), 2'-O-methyl, locked nucleic acid (LNA), and 2'-fluoro.

6. The compound of claim 5, wherein each 2' sugar modification is a 2'-O-(2-methoxyethyl) (2'-MOE).

7. The compound of claim 5, wherein each 2' sugar modification is a 2'-O-methyl.

8. The compound of claim 5, wherein each 2' sugar modification is a 2'-fluoro.

9. The compound of claim 5, wherein each 2' modification of said sugar results in a bicyclic sugar.

10. The compound of claim 9, wherein said 2' modification is a locked nucleic acid (LNA).

11. The compound of claim 3, wherein said chemical modification to said sugar is a 4' thio.

12. The compound of claim 4, comprising two or more chemically distinct 2' sugar modifications.

13. The compound of claim 3, comprising at least one internucleoside linkage modification.

14. The compound of claim 13, comprising mixed phosphorothioate and phosphodiester linkages.

15. The compound of claim 14, comprising alternating phosphorothioate and phosphodiester internucleoside linkages.

16. The compound of claim 5, comprising at least one internucleoside linkage modification.

17. The compound of claim 16, comprising mixed phosphorothioate and phosphodiester linkages.

18. The compound of claim 17, comprising alternating phosphorothioate and phosphodiester internucleoside linkages.

19. The compound of claim 1, comprising a conjugate.

20. The compound of claim 2, wherein said compound is canonical.

21. A pharmaceutical composition, comprising said compound of claim 1 and a pharmaceutically acceptable carrier, diluent, or excipient.

22. A method for treating a condition associated with survivin expression or overexpression, comprising administering to a human an effective amount of said compound of claim 1.

23. The method of claim 22, wherein said condition is cancer.

24. The method of claim 23, wherein said cancer is selected from the group consisting of hepatocellular cancer, breast cancer, colon cancer, prostate cancer, lung cancer, bladder cancer, ovarian cancer, renal cancer, glioblastoma, pancreatic cancer, and non-Hodgkin's lymphoma.

* * * * *

SEQUENCE LISTING

```
<160> NUMBER OF SEQ ID NOS: 233

<210> SEQ ID NO 1
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 2
atgcattctg cccccaagga                                              20

<210> SEQ ID NO 3
<211> LENGTH: 14796
<212> TYPE: DNA
<213> ORGANISM: Artificial Sequence
<220> FEATURE:
<223> OTHER INFORMATION: H. sapien

<400> SEQUENCE: 3
```

```
tctagacatg cggatatatt caagctgggc acagcacagc agccccaccc caggcagctt      60
gaaatcagag ctggggtcca aagggaccac accccgaggg actgtgtggg ggtcggggca     120
cacaggccac tgcttccccc cgtctttctc agccattcct gaagtcagcc tcactctgct     180
tctcagggat ttcaaatgtg cagagactct ggcacttttg tagaagcccc ttctggtcct     240
aacttacacc tggatgctgt ggggctgcag ctgctgctcg ggctcgggag gatgctgggg     300
gcccggtgcc catgagcttt tgaagctcct ggaactcggt tttgagggtg ttcaggtcca     360
ggtggacacc tgggctgtcc ttgtccatgc atttgatgac attgtgtgca gaagtgaaaa     420
ggagttaggc cgggcatgct ggcttatgcc tgtaatccca gcactttggg aggctgaggc     480
gggtggatca cgaggtcagg agttcaatac cagcctggcc aagatggtga aacccccgtct    540 ctactaaaaa tacaaaaaaa ttagccgggc atggtggcgg cgcatgtaa tcccagctac      600 tgggggggct gaggcagaga attgctggaa cccaggagat ggaggttgca gtgagccaag     660
attgtgccac tgcactgcac tccagcctgg cgacagagca agactctgtc tcaaaaaaaa     720
aaaaaaaaag tgaaaaggag ttgttccttt cctccctcct gagggcaggc aactgctgcg     780
gttgccagtg gaggtggtgc gtccttggtc tgtgcctggg ggccacccca gcagaggcca     840
tggtggtgcc agggcccggt tagcgagcca atcagcagga cccaggggcg acctgccaaa     900
gtcaactgga tttgataact gcagcgaagt taagtttcct gattttgatg attgtgttgt     960
ggttgtgtaa gagaatgaag tatttcgggg tagtatggta atgccttcaa cttacaaacg    1020
gttcaggtaa accacccata tacatacata tacatgcatg tgatatatac acatacaggg    1080
atgtgtgtgt gttcacatat atgaggggag agagactagg ggagagaaag taggttgggg    1140
agagggagag agaaaggaaa acaggagaca gagagagagc ggggagtaga gagagggaag    1200
gggtaagaga gggagaggag gagagaaagg gaggaagaag cagagagtga atgttaaagg    1260
aaacaggcaa aacataaaca gaaaatctgg gtgaagggta tatgagtatt ctttgtacta    1320
ttcttgcaat tatcttttat ttaaattgac atcgggccgg gcgcagtggc tcacatctgt    1380
aatcccagca ctttgggagg ccgaggcagg cagatcactt gaggtcagga gtttgagacc    1440
agcctggcaa acatggtgaa accccatctc tactaaaaat acaaaaatta gcctggtgtg    1500
gtggtgcatg cctttaatct cagctactcg ggaggctgag gcaggagaat cgcttgaacc    1560
cgtggcgggg aggaggttgc agtgagctga gatcatgcca ctgcactcca gcctgggcga    1620
tagagcgaga ctcagtttca aataaataaa taaacatcaa ataaaaagt tactgtatta    1680 aagaatgggg gcggggtggg aggggtgggg agaggttgca aaaataaata aataaataaa    1740
taaaccccaa aatgaaaaag acagtggagg caccaggcct gcgtgggget ggagggctaa    1800 taaggccagg cctcttatct ctggccatag aaccagagaa gtgagtggat gtgatgccca    1860
gctccagaag tgactccaga acaccctgtt ccaaagcaga ggacacactg attttttttt    1920
taataggctg caggacttac tgttggtggg acgcccctgct ttgcgaaggg aaaggaggag   1980
tttgccctga gcacaggccc ccacccctcca ctgggctttc cccagctccc ttgtcttctt    2040
atcacggtag tggcccagtc cctggcccct gactccagaa ggtggccctc ctggaaaccc    2100
aggtcgtgca gtcaacgatg tactcgccgg gacagcgatg tctgctgcac tccatccctc    2160
ccctgttcat ttgtccttca tgcccgtctg gagtagatgc tttttgcaga ggtggcaccc    2220
tgtaaagctc tcctgtctga cttttttttt tttttagac tgagttttgc tcttgttgcc    2280
taggctggag tgcaatggca caatctcagc tcactgcacc ctctgcctcc cgggttcaag    2340
cgattctcct gcctcagcct cccgagtagt tgggattaca ggcatgcacc accacgccca    2400
```

```
gctaattttt gtatttttag tagagacaag gtttcaccgt gatggccagg ctggtcttga   2460
actccaggac tcaagtgatg ctcctgccta ggcctctcaa agtgttggga ttacaggcgt   2520
gagccactgc acccggcctg cacgcgttct ttgaaagcag tcgaggggc gctaggtgtg    2580
ggcagggacg agctggcgcg gcgtcgctgg gtgcaccgcg accacgggca gagccacgcg   2640
gcggaggac tacaactccc ggcacacccc gcgccgcccc gcctctactc ccagaaggcc    2700
gcgggggtg gaccgcctaa gagggcgtgc gctcccgaca tgccccgcgg cgcgccatta    2760
accgccagat ttgaatcgcg ggacccgttg gcagaggtgg cggcggcggc atgggtgccc   2820
cgacgttgcc ccctgcctgg cagccctttc tcaaggacca ccgcatctct acattcaaga   2880
actggccctt cttggagggc tgcgcctgca ccccggagcg ggtgagactg cccggcctcc   2940
tggggtcccc cacgcccgcc ttgccctgtc cctagcgagg ccactgtgac tgggcctcgg   3000
gggtacaagc cgcccctccc ctcccgtcct gtccccagcg aggccactgt ggctgggccc   3060
cttgggtcca ggccggcctc ccctccctgc tttgtcccca tcgaggcctt tgtggctggg   3120
cctcgggtt ccgggctgcc acgtccactc acgagctgtg ctgtcccttg cagatggccg    3180
aggctggctt catccactgc cccactgaga acagccaga cttggcccag tgtttcttct    3240
gcttcaagga gctggaaggc tgggagccag atgacgaccc catgtaagtc ttctctggcc   3300
agcctcgatg ggctttgttt tgaactgagt tgtcaaaaga tttgagttgc aaagacactt   3360
agtatgggag ggttgctttc caccctcatt gcttcttaaa cagctgttgt gaacggatac   3420
ctctctatat gctggtgcct tggtgatgct tacaacctaa ttaaatctca tttgaccaaa   3480
atgccttggg gtggacgtaa gatgcctgat gcctttcatg ttcaacagaa tacatcagca   3540
gaccctgttg ttgtgaactc ccaggaatgt ccaagtgctt tttttgagat tttttaaaaa   3600
acagtttaat tgaaatataa cctacacagc acaaaaatta ccctttgaaa gtgtgcactt   3660
cacactttcg gaggctgagg cgggcggatc acctgaggtc aggagttcaa gacctgcctg   3720
gccaacttgg cgaaaccccg tctctactaa aaatacaaaa attagccggg catggtagcg   3780
cacgcccgta atcccagcta ctcgggaggc taaggcagga gaatcgcttg aacctgggag   3840
gcggaggttg cagtgagccg agattgtgcc aatgcactcc agcctcggcg acagagcgag   3900
actccgtcat aaaaataaaa aattgaaaaa aaaaaagaa agaaagcata tacttcagtg    3960
ttgttctgga tttttttctt caagatgcct agttaatgac aatgaaattc tgtactcgga   4020
tggtatctgt ctttccacac tgtaatgcca tattctttc tcaccttttt ttctgtcgga    4080
ttcagttgct tccacagctt taattttttt cccctggaga atcaccccag ttgttttct    4140
ttttggccag aagagagtag ctgttttttt tcttagtatg tttgctatgg tggttatact   4200
gcatccccgt aatcactggg aaaagatcag tggtattctt cttgaaaatg aataagtgtt   4260
atgatatttt cagattagag ttacaactgg ctgtctttt ggactttgtg tggccatgtt    4320
ttcattgtaa tgcagttctg gtaacggtga tagtcagtta tacagggaga ctcccctagc   4380
agaaaatgag agtgtgagct aggggtccc ttggggaacc cggggcaata atgcccttct    4440
ctgcccttaa tccttacagt gggccgggca cggtggctta cgcctgtaat accagcactt   4500
tgggaggccg aggcgggcgg atcacgaggt caggagatcg agaccatctt ggctaatacg   4560
gtgaaacccc gtctccacta aaaatacaaa aaattagccg ggcgtggtgg tgggcgcctg   4620
tagtcccagc tactcgggag gctgaggcag gagaatggcg tgaacccagg aggcggagct   4680
tgcagtgagc cgagattgca ccactgcact ccagcctggg cgacagaatg agactccgtc   4740
```

```
tcaaaaaaaa aaaaaaaga aaaaaatctt tacagtggat tacataacaa ttccagtgaa    4800
atgaaattac ttcaaacagt tccttgagaa tgttggaggg atttgacatg taattccttt    4860
ggacatatac catgtaacac ttttccaact aattgctaag gaagtccaga taaaatagat    4920
acattagcca cacagatgtg gggggagatg tccacaggga gagagaaggt gctaagaggt    4980
gccatatggg aatgtggctt gggcaaagca ctgatgccat caacttcaga cttgacgtct    5040
tactcctgag gcagagcagg gtgtgcctgt ggagggcgtg gggaggtggc ccgtggggag    5100
tggactgccg ctttaatccc ttcagctgcc tttccgctgt tgttttgatt tttctagaga    5160
ggaacataaa aagcattcgt ccggttgcgc tttcctttct gtcaagaagc agtttgaaga    5220
attaacccct ggtgaatttt tgaaactgga cagagaaaga gccaagaaca aaattgtatg    5280
tattgggaat aagaactgct caaaccctgt tcaatgtctt tagcactaaa ctacctagtc    5340
cctcaaaggg actctgtgtt ttcctcagga agcattttt ttttttttct gagatagagt    5400
ttcactcttg ttgcccaggc tggagtgcaa tggtgcaatc ttggctcact gcaacctctg    5460
cctctcgggt tcaagtgatt ctcctgcctc agcctcccaa gtaactggga ttacagggaa    5520
gtgccaccac acccagctaa ttttgtatt tttagtagag atggggtttc accacattgc    5580
ccaggctggt cttgaactcc tgacctcgtg attcgcccac cttggcctcc caaagtgctg    5640
ggattacagg cgtgaaccac cacgcctggc ttttttttt ttgttctgag acacagtttc    5700
actctgttac ccaggctgga gtagggtggc ctgatctcgg atcactgcaa cctccgcctc    5760
ctgggctcaa gtgatttgcc tgcttcagcc tcccaagtag ccgagattac aggcatgtgc    5820
caccacaccc aggtaatttt tgtattttg gtagagacga ggtttcacca tgttggccag    5880
gctggttttg aactcctgac ctcaggtgat ccaccgcct cagcctccca aagtgctgag    5940
attataggtg tgagccacca cacctggcct caggaagtat ttttattttt aaatttattt    6000
atttatttga gatggagtct tgctctgtcg cccaggctag agtgcagcga cgggatctcg    6060
gctcactgca agctccgccc cccaggttca agccattctc ctgcctcagc ctcccgagta    6120
gctgggacta caggcgcccg ccaccacacc cggctaattt ttttgtattt ttagtagaga    6180
cgggttttca ccgtgttagc caggagggtc ttgatctcct gacctcgtga tctgcctgcc    6240
tcggcctccc aaagtgctgg gattacaggt gtgagccacc acacccggct atttttattt    6300
ttttgagaca gggactcact ctgtcacctg ggctgcagtg cagtggtaca ccatagctca    6360
ctgcagcctc gaactcctga gctcaagtga tcctcccacc tcatcctcac aagtaattgg    6420
gactacaggt gcacccacc atgcccacct aatttattta tttatttatt tatttatttt    6480
catagagatg agggttccct gtgttgtcca ggctggtctt gaactcctga gctcacggga    6540
tccttttgcc tgggcctccc aaagtgctga gattacaggc atgagccacc gtgcccagct    6600
aggaatcatt tttaaagccc ctaggatgtc tgtgtgattt taaagctcct ggagtgtggc    6660
cggtataagt atataccggt ataagtaaat cccacatttt gtgtcagtat ttactagaaa    6720
cttagtcatt tatctgaagt tgaaatgtaa ctgggcttta tttatttatt tatttattta    6780
tttattttta attttttttt ttgagacgag tctcactttg tcacccaggc tggagtgcag    6840
tggcacgatc tcggctcact gcaacctctg cctcccgggg tcaagcgatt ctcctgcctt    6900
agcctcccga gtagctggga ctacaggcac gcaccaccat gcctggctaa ttttgtatt    6960 tttagtagac ggggtttcac catgctggcc aagctggtct caaactcctg accttgtgat    7020
ctgcccgctt tagcctccca gagtgctggg attacaggca tgagccacca tgcgtggtct    7080
ttttaaaatt ttttgatttt ttttttttt gagacagagc cttgctctgt cgcccaggct    7140
```

```
ggagtgcagt ggcacgatct cagctcacta caagctccgc ctcccgggtt cacgccattc   7200
ttctgcctca gcctcctgag tagctgggac tacaggtgcc caccaccacg cctggctaat   7260 ttttttttggt attttattta gagacaaggt ttcatcatgt tggccaggct ggtctcaaac   7320
tcctgacctc aagtgatctg cctgcctcgg cctcccaaag cgctgagatt acaggtgtga   7380
tctactgcgc caggcctggg cgtcatatat tcttatttgc taagtctggc agccccacac   7440
agaataagta ctgggggatt ccatatcctt gtagcaaagc cctgggtgga gagtcaggag   7500
atgttgtagt tctgtctctg ccacttgcag actttgagtt taagccagtc gtgctcatgc   7560
tttccttgct aaatagaggt tagaccccct atcccatggt ttctcaggtt gcttttcagc   7620
ttgaaaattg tattcctttg tagagatcag cgtaaaataa ttctgtcctt atatgtggct   7680 ttatttttaat ttgagacaga gtgtcactca gtcgcccagg ctggagtgtg gtggtgcgat   7740
cttggctcac tgcgacctcc acctcccagg ttcaagcgat tctcgtgcct caggctccca   7800
agtagctgag attataggtg tgtgccacca ggcccagcta acttttgtat ttttagtaga   7860
gacagggttt tgccatgttg gctaagctgg tctcgaactc ctggcctcaa gtgatctgcc   7920
cgccttggca tcccaaagtg ctgggattac aggtgtgaac caccacacct ggcctcaata   7980
tagtggcttt taagtgctaa ggactgagat tgtgttttgt caggaagagg ccagttgtgg   8040
gtgaagcatg ctgtgagaga gcttgtcacc tggttgaggt tgtgggagct gcagcgtggg   8100
aactggaaag tgggctgggg atcatctttt tccaggtcag gggtcagcca gcttttctgc   8160
agcgtgccat agaccatctc ttagccctcg tgggtcagag tctctgttgc atattgtctt   8220
ttgttgtttt tcacaacctt ttagaaacat aaaaagcatt cttagcccgt gggctggaca   8280
aaaaaaggcc atgacgggct gtatggattt ggcccagcag gcccttgctt gccaagccct   8340
gttttagaca aggagcagct tgtgtgcctg gaaccatcat gggcacaggg gaggagcaga   8400
gtggatgtgg aggtgtgagc tggaaaccag gtcccagagc gctgagaaag acagagggtt   8460
tttgcccttg caagtagagc aactgaaatc tgacaccatc cagttccaga aagccctgaa   8520
gtgctggtgg acgctgcggg gtgctccgct ctagggttac agggatgaag atgcagtctg   8580 gtaggggggag tccactcacc tgttggaaga tgtgattaag aaaagtagac tttcagggcc   8640
gggcatggtg gctcacgcct gtaatcccag cactttggga ggccgaggcg ggtggatcac   8700
gaggtcagga gatcgagacc atcctggcta acatggtgaa accccgtctt tactaaaaat   8760
acaaaaaatt agctgggcgt ggtggcgggc gcctgtagtc ccagctactc gggaggctga   8820
ggcaggagaa tggcgtgaac ctgggaggtg gagcttgctg tgagccgaga tcgcgccact   8880
gcactccagc ctgggcgaca gagcgagact ccgtctcaaa aaaaaaaaa aaagtaggct   8940 ttcatgatgt gtgagctgaa ggcgcagtag gcagaagtag aggcctcagt ccctgcagga   9000
gacccctcgg tctctatctc ctgatagtca gacccagcca cactgaaaag aggggagaca   9060
ttacagcctg cgagaaaagt agggagattt aaaaactgct tggcttttat tttgaactgt   9120 ttttttttgtt tgtttgtttt ccccaattca gaatacagaa tacttttatg gatttgtttt   9180
tattacttta attttgaaac aatataatct ttttttttgtt gttttttttga cagggtct    9240 tactctgtca cccaggctga gtgcagtggt gtgatcttgg ctcacctcag cctcgacccc   9300
ctgggctcaa atgattctcc cacctcagct tcccaagtag ctgggaccac aggtgcgtgt   9360
gttgcgctat acaaatcctg aagacaagga tgctgttgct ggtgatgctg ggattccca   9420 agatcccaga tttgatggca ggatgcccct gtctgctgcc ttgccagggt gccaggaggg   9480
```

```
cgctgctgtg gaagctgagg cccggccatc cagggcgatg cattgggcgc tgattcttgt   9540
tcctgctgct gcctcggtgc ttagcttttg aaacaatgaa ataaattaga accagtgtga   9600
aaatcgatca gggaataaat ttaatgtgga aataaactga acaacttagt tcttcataag   9660
agtttacttg gtaaatactt gtgatgagga caaaacgaag cactagaagg agaggcgagt   9720
tgtagacctg ggtggcagga gtgttttgtt tgttttcttt ggcagggtct tgctctgttg   9780
ctcaggctgg agtacagtgg cacaatcaca gctcactata gcctcgacct cctggactca   9840
agcaatcctc ctgcctcagc ctcccagtag ctgggactac aggcgcatgc caccatgcct   9900
ggctaatttt aaattttttt ttttctcttt tttgagatgg aatctcactc tgtcgcccag   9960
gctggagtgc agtggcgtga tctcggctga cggcaagctc cgcctcccag gttcactcca  10020
ttcgcctgcc tcagcctccc aagtagctgg gactacaggc gctgggatta caaacccaaa  10080
cccaaagtgc tgggattaca ggcgtgagcc actgcacccg gcctgttttg tctttcaata  10140
gcaagagttg tgtttgcttc gcccctacct ttagtggaaa aatgtataaa atggagatat  10200
tgacctccac attggggtgg ttaaattata gcatgtatgc aaaggagctt cgctaattta  10260
aggcttttt gaaagagaag aaactgaata atccatgtgt gtatatatat tttaaaagcc  10320
atggtcatct ttccatatca gtaaagctga ggctccctgg gactgcagag ttgtccatca  10380
cagtccatta taagtgcgct gctgggccag gtgcagtggc ttgtgcctga atcccagcac  10440
tttgggaggc caaggcagga ggattcattg agcccaggag ttttgaggcg agcctgggca  10500
atgtggccag acctcatctc ttcaaaaaat acacaaaaaa ttagccaggc atggtggcac  10560
gtgcctgtag tctcagctac tcaggaggct gaggtgggag gatcactttg agccttgcag  10620
gtcaaagctg cagtaagcca tgatcttgcc actgcattcc agcctggatg acagagcgag  10680
accctgtctc taaaaaaaaa aaaaccaaa cggtgcactg ttttcttttt tcttatcaat  10740
ttattatttt taaattaaat tttcttttaa taatttataa attataaatt tatattaaaa  10800
aatgacaaat ttttattact tatacatgag gtaaaactta ggatatataa agtacatatt  10860
gaaaagtaat ttttttggctg gcacagtggc tcacacctgt aatcccagca ctttgggagg  10920
ccgtggcggg cagatcacat gagatcatga gttcgagacc aacctgacca acatggagag  10980
accccatctc tactaaaaat acaaaattag ccggggtggt ggcgcatgcc tgtaatccca  11040
gctactcggg aggctgaggc aggagaatct cttgaacccg ggaggcagag gttgcggtga  11100
gccaagatcg tgcctttgca caccagccta ggcaacaaga gcgaaagtcc gtctcaaaaa  11160
aaaagtaatt ttttttaagt taacctctgt cagcaaacaa atttaaccca ataaaggtct  11220
ttgttttta atgtagtaga ggagttaggg tttataaaaa atatggtagg aaggggtc  11280
cctggatttg ctaatgtgat tgtcatttgc cccttaggag agagctctgt tagcagaatg  11340
aaaaaattgg aagccagatt caggaggga ctggaagcaa agaatttct gttcgaggaa  11400
gagcctgatg tttgccaggg tctgtttaac tggacatgaa gaggaaggct ctggactttc  11460
ctccaggagt ttcaggagaa aggtagggca gtggttaaga gcagagctct gcctagacta  11520
gctgggtgc ctagactagc tggggtgccc agactagctg gggtgcctag actagctggg  11580
tactttgagt ggctccttca gcctggacct cggtttcctc acctgtatag tagagatatg  11640
ggagcaccca gcgcaggatc actgtgaaca taaatcagtt aatggaggaa gcaggtagag  11700
tggtgctggg tgcataccaa gcactccgtc agtgtttcct gttattcgat gattaggagg  11760
cagcttaaac tagagggagt tgagctgaat caggatgttt gtcccaggta gctgggaatc  11820
tgcctagccc agtgcccagt ttatttaggt gctctctcag tgttccctga ttgttttttc  11880
```

```
ctttgtcatc ttatctacag gatgtgactg ggaagctctg gtttcagtgt catgtgtcta   11940
ttctttattt ccaggcaaag gaaaccaaca ataagaagaa agaatttgag gaaactgcga   12000
agaaagtgcg ccgtgccatc gagcagctgg ctgccatgga ttgaggcctc tggccggagc   12060
tgcctggtcc cagagtggct gcaccacttc cagggtttat tccctggtgc caccagcctt   12120
cctgtgggcc ccttagcaat gtcttaggaa aggagatcaa cattttcaaa ttagatgttt   12180
caactgtgct cctgttttgt cttgaaagtg gcaccagagg tgcttctgcc tgtgcagcgg   12240
gtgctgctgg taacagtggc tgcttctctc tctctctctc ttttttgggg gctcattttt   12300
gctgttttga ttcccgggct taccaggtga gaagtgaggg aggaagaagg cagtgtccct   12360
tttgctagag ctgacagctt tgttcgcgtg ggcagagcct tccacagtga atgtgtctgg   12420
acctcatgtt gttgaggctg tcacagtcct gagtgtggac ttggcaggtg cctgttgaat   12480
ctgagctgca ggttccttat ctgtcacacc tgtgcctcct cagaggacag tttttttgtt   12540
gttgtgtttt tttgttttttt tttttggta gatgcatgac ttgtgtgtga tgagagaatg   12600
gagacagagt ccctggctcc tctactgttt aacaacatgg cttttcttatt ttgtttgaat   12660
tgttaattca cagaatagca caaactacaa ttaaaactaa gcacaaagcc attctaagtc   12720
attgggaaa cggggtgaac ttcaggtgga tgaggagaca gaatagagtg ataggaagcg   12780
tctggcagat actccttttg ccactgctgt gtgattagac aggcccagtg agccgcgggg   12840
cacatgctgg ccgctcctcc ctcagaaaaa ggcagtggcc taaatccttt ttaaatgact   12900
tggctcgatg ctgtggggga ctggctgggc tgctgcaggc cgtgtgtctg tcagcccaac   12960
cttcacatct gtcacgttct ccacacgggg gagagacgca gtccgcccag gtccccgctt   13020
tctttggagg cagcagctcc cgcagggctg aagtctggcg taagatgatg gatttgattc   13080
gccctcctcc ctgtcataga gctgcagggt ggattgttac agcttcgctg gaaacctctg   13140
gaggtcatct cggctgttcc tgagaaataa aaagcctgtc atttcaaaca ctgctgtgga   13200
ccctactggg tttttaaaat attgtcagtt tttcatcgtc gtccctagcc tgccaacagc   13260
catctgccca gacagccgca gtgaggatga gcgtcctggc agagacgcag ttgtctctgg   13320
gcgcttgcca gagccacgaa ccccagacct gtttgtatca tccgggctcc ttccgggcag   13380
aaacaactga aaatgcactt cagacccact tattatgcc acatctgagt cggcctgaga   13440
tagactttc cctctaaact gggagaatat cacagtggtt tttgttagca gaaaatgcac   13500
tccagcctct gtactcatct aagctgctta ttttttgatat ttgtgtcagt ctgtaaatgg   13560
atacttcact ttaataactg ttgcttagta attggctttg tagagaagct ggaaaaaaat   13620
ggttttgtct tcaactcctt tgcatgccag gcggtgatgt ggatctcggc ttctgtgagc   13680
ctgtgctgtg ggcagggctg agctggagcc gcccctctca gcccgcctgc cacggccttt   13740
ccttaaaggc catccttaaa accagaccct catggctgcc agcacctgaa agcttcctcg   13800
acatctgtta ataaagccgt aggcccttgt ctaagcgcaa ccgcctagac tttctttcag   13860
atacatgtcc acatgtccat ttttcaggtt ctctaagttg gagtggagtc tgggaagggt   13920
tgtgaatgag gcttctgggc tatgggtgag gttccaatgg caggttagag cccctcgggc   13980
caactgccat cctggaaagt agagacagca gtgcccgctg cccagaagag accagcaagc   14040
caaactggag cccccattgc aggctgtcgc catgtggaaa gagtaactca caattgccaa   14100
taaagtctca tgtggtttta tctactttttt ttttctttttt cttttttttt gagacaaggc   14160
cttgccctcc caggctggag tgcagtggaa tgaccacagc tcaccgcaac ctcaaattct   14220
```

```
tgcgttcaag tgaacctccc actttagcct cccaagtagc tgggactaca ggcgcacgcc   14280
atcacacccg gctaattgaa aaattttttt ttttgtttag atggaatctc actttgttgc   14340
ccaggctggt ctcaaactcc tgggctcaag tgatcatcct gcttcagcgt ccgacttgtt   14400
ggtattatag gcgtgagcca ctgggcctga cctagctacc attttttaat gcagaaatga   14460
agacttgtag aaatgaaata acttgtccag gatagtcgaa taagtaactt ttagagctgg   14520
gatttgaacc caggcaatct ggctccagag ctgggccctc actgctgaag gacactgtca   14580
gcttgggagg gtggctatgg tcggctgtct gattctaggg agtgagggct gtctttaaag   14640 cacccccattc cattttcaga cagctttgtc agaaaggctg tcatatggag ctgacacctg   14700
cctccccaag gcttccatag atcctctctg tacattgtaa ccttttattt tgaaatgaaa   14760
attcacagga agttgtaagg ctagtacagg ggatcc                             14796

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
aaggaccacc gcatctctac a                                             21

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
ccaagtctgg ctcgttctca gt                                            22

<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6
cgaggctggc ttcatccact gcc                                           23

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                               20
```

```
<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                  20

<210> SEQ ID NO 10
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 10
cgagaggcgg acgggaccg                                                   19

<210> SEQ ID NO 11
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 11
cgagaggcgg acgggaccgt t                                                21

<210> SEQ ID NO 12
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 12
ttgctctccg cctgccctgg c                                                21

<210> SEQ ID NO 13
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 13
gctctccgcc tgccctggc                                                   19

<210> SEQ ID NO 14
<211> LENGTH: 1619
<212> TYPE: DNA
<213> ORGANISM: Artificial Sequence
<220> FEATURE:
<223> OTHER INFORMATION: H. sapien

<400> SEQUENCE: 14
ccgccagatt tgaatcgcgg gacccgttgg cagaggtggc ggcggcggca tgggtgcccc      60
gacgttgccc cctgcctggc agcccttcct caaggaccac cgcatctcta cattcaagaa    120
ctggcccttc ttggagggct gcgctgcac cccggagcgg atggccgagg ctggcttcat    180
ccactgcccc actgagaacg agccagactt ggcccagtgt ttcttctgct tcaaggagct    240
```

```
ggaaggctgg gagccagatg acgaccccat agaggaacat aaaaagcatt cgtccggttg      300
cgctttcctt tctgtcaaga agcagtttga agaattaacc cttggtgaat ttttgaaact      360
ggacagagaa agagccaaga acaaaattgc aaaggaaacc aacaataaga agaaagaatt      420
tgaggaaact gcgaagaaag tgcgccgtgc catcgagcag ctggctgcca tggattgagg      480
cctctggccg gagctgcctg gtcccagagt ggctgcacca cttccagggt ttattccctg      540
gtgccaccag ccttcctgtg ggccccttag caatgtctta ggaaaggaga tcaacatttt      600
caaattagat gtttcaactg tgctcctgtt ttgtcttgaa agtggcacca gaggtgcttc      660
tgcctgtgca gcgggtgctg ctggtaacag tggctgcttc tctctctctc tctctttttt      720
gggggctcat ttttgctgtt ttgattcccg ggcttaccag gtgagaagtg agggaggaag      780
aaggcagtgt cccttttgct agagctgaca gctttgttcg cgtgggcaga gccttccaca      840
gtgaatgtgt ctggacctca tgttgttgag gctgtcacag tcctgagtgt ggacttggca      900
ggtgcctgtt gaatctgagc tgcaggttcc ttatctgtca cacctgtgcc tcctcagagg      960 acagttttt tgttgttgtg tttttttgtt ttttttttt ggtagatgca tgacttgtgt    1020
gtgatgagag aatggagaca gagtccctgg ctcctctact gtttaacaac atggctttct     1080
tattttgttt gaattgttaa ttcacagaat agcacaaact acaattaaaa ctaagcacaa      1140
agccattcta agtcattggg gaaacggggt gaacttcagg tggatgagga gacagaatag     1200
agtgatagga agcgtctggc agatactcct tttgccactg ctgtgtgatt agacaggccc     1260
agtgagccgc ggggcacatg ctggccgctc ctccctcaga aaaaggcagt ggcctaaatc     1320
ctttttaaat gacttggctc gatgctgtgg gggactggct gggctgctgc aggccgtgtg     1380
tctgtcagcc caaccttcac atctgtcacg ttctccacac gggggagaga cgcagtccgc     1440
ccaggtcccc gctttctttg gaggcagcag ctcccgcagg gctgaagtct ggcgtaagat     1500
gatggatttg attcgccctc ctccctgtca tagagctgca gggtggattg ttacagcttc     1560
gctggaaacc tctggaggtc atctcggctg ttcctgagaa ataaaaagcc tgtcatttc      1619

<210> SEQ ID NO 15
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 15
agggcugcca ggcaggggggc                                                 20

<210> SEQ ID NO 16
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 16
gccccugccu ggcagcccu                                                   19

<210> SEQ ID NO 17
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 17
```

-continued auccauggca gccagcugcu    20

<210> SEQ ID NO 18
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 18
agcagcuggc ugccauggau    20

<210> SEQ ID NO 19
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 19
aacccuggaa guggugcagc    20

<210> SEQ ID NO 20
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 20
gcugcaccac uuccaggguu    20

<210> SEQ ID NO 21
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 21
aggcuggugg caccagggaa    20

<210> SEQ ID NO 22
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 22
uucccuggug ccaccagccu    20

<210> SEQ ID NO 23
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 23
auuugaaaau guugaucucc    20

<210> SEQ ID NO 24
<211> LENGTH: 20
<212> TYPE: RNA

-continued

```
<213> ORGANISM: Artificial Sequence
<220> FEATURE:
<223> OTHER INFORMATION: Oligomeric Compound

<400> SEQUENCE: 24
ggagaucaac auuuucaaau                                                    20

<210> SEQ ID NO 25
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 25
agcacaguug aaacaucuaa                                                    20

<210> SEQ ID NO 26
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 26
uuagauguuu caacgugcu                                                     20

<210> SEQ ID NO 27
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 27
agaagcaccu cuggugccac                                                    20

<210> SEQ ID NO 28
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 28
guggcaccag aggugcuucu                                                    20

<210> SEQ ID NO 29
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 29
ucccucacuu cucaccuggu                                                    20

<210> SEQ ID NO 30
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 30
accaggugag aagugaggga                                                    20
```

```
<210> SEQ ID NO 31
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 31
gcaaaaggga cacugccuuc                                               20

<210> SEQ ID NO 32
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 32
gaaggcagug ucccuuuugc                                               20

<210> SEQ ID NO 33
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 33
aggcucugcc cacgcgaaca                                               20

<210> SEQ ID NO 34
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 34
uguucgcgug ggcagagccu                                               20

<210> SEQ ID NO 35
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 35
caacaugagg uccagacaca                                               20

<210> SEQ ID NO 36
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 36
ugugucugga ccucauguug                                               20

<210> SEQ ID NO 37
<211> LENGTH: 20
<212> TYPE: RNA
<213> ORGANISM: Artificial Sequence
<220> FEATURE:
```

<223> OTHER INFORMATION: Oligomeric Compound

<400> SEQUENCE: 37
aguccacacu caggacugug					20

<210> SEQ ID NO 38
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 38
cacaguccug aguguggacu					20

<210> SEQ ID NO 39
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 39
uaaggaaccu gcagcucaga					20

<210> SEQ ID NO 40
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 40
ucugagcugc agguuccuua					20

<210> SEQ ID NO 41
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 41
cagggacucu gucuccauuc					20

<210> SEQ ID NO 42
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 42
gaauggagac agagucccug					20

<210> SEQ ID NO 43
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 43
aacaaaauaa gaaagccaug					20

```
<210> SEQ ID NO 44
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 44
cauggcuuuc uuauuuuguu                                               20

<210> SEQ ID NO 45
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 45
gcuauucugu gaauuaacaa                                               20

<210> SEQ ID NO 46
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 46
uuguuaauuc acagaauagc                                               20

<210> SEQ ID NO 47
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 47
aguuugugcu auucugugaa                                               20

<210> SEQ ID NO 48
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 48
uucacagaau agcacaaacu                                               20

<210> SEQ ID NO 49
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 49
agaauggcuu ugugcuuagu                                               20

<210> SEQ ID NO 50
<211> LENGTH: 20
<212> TYPE: RNA
<213> ORGANISM: Artificial Sequence
<220> FEATURE:
<223> OTHER INFORMATION: Oligomeric Compound
```

-continued

```
<400> SEQUENCE: 50
acuaagcaca aagccauucu                                              20

<210> SEQ ID NO 51
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 51
uccaccugaa guucaccccg                                              20

<210> SEQ ID NO 52
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 52
cggggugaac uucaggugga                                              20

<210> SEQ ID NO 53
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 53
aaggaguauc ugccagacgc                                              20

<210> SEQ ID NO 54
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 54
gcgucuggca gauacuccuu                                              20

<210> SEQ ID NO 55
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 55
uaaucacaca gcaguggcaa                                              20

<210> SEQ ID NO 56
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 56
uugccacugc ugugugauua                                              20

<210> SEQ ID NO 57
<211> LENGTH: 20
```

```
<212> TYPE: RNA
<213> ORGANISM: Artificial Sequence
<220> FEATURE:
<223> OTHER INFORMATION: Oligomeric Compound

<400> SEQUENCE: 57
gugccccgcg gcucacuggg                                              20

<210> SEQ ID NO 58
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 58
cccagugagc cgcggggcac                                              20

<210> SEQ ID NO 59
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 59
aaaggauuua ggccacugcc                                              20

<210> SEQ ID NO 60
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 60
ggcaguggcc uaaauccuuu                                              20

<210> SEQ ID NO 61
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 61
acagcaucga gccaagucau                                              20

<210> SEQ ID NO 62
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 62
augacuuggc ucgaugcugu                                              20

<210> SEQ ID NO 63
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 63
```

-continued

| | |
|---|---|
| acagacacac ggccugcagc | 20 |

<210> SEQ ID NO 64
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 64

| | |
|---|---|
| gcugcaggcc gugugucugu | 20 |

<210> SEQ ID NO 65
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 65

| | |
|---|---|
| gaacgugaca gaugugaagg | 20 |

<210> SEQ ID NO 66
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 66

| | |
|---|---|
| ccuucacauc ugcacguuc | 20 |

<210> SEQ ID NO 67
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 67

| | |
|---|---|
| uccaucaucu uacgccagac | 20 |

<210> SEQ ID NO 68
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 68

| | |
|---|---|
| gucuggcgua agaugaugga | 20 |

<210> SEQ ID NO 69
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 69

| | |
|---|---|
| ggcgaaucaa auccaucauc | 20 |

<210> SEQ ID NO 70
<211> LENGTH: 20
<212> TYPE: RNA
<213> ORGANISM: Artificial Sequence

```
<220> FEATURE:
<223> OTHER INFORMATION: Oligomeric Compound

<400> SEQUENCE: 70
gaugauggau uugauucgcc                                                   20

<210> SEQ ID NO 71
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 71
auccacccug cagcucuaug                                                   20

<210> SEQ ID NO 72
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 72
cauagagcug caggguggau                                                   20

<210> SEQ ID NO 73
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 73
gccgagauga ccuccagagg                                                   20

<210> SEQ ID NO 74
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 74
ccucuggagg ucaucucggc                                                   20

<210> SEQ ID NO 75
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 75
uuugaaaaug uugaucuccu t                                                 21

<210> SEQ ID NO 76
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 76
ggagaucaac auuuucaaat t                                                 21
```

-continued

<210> SEQ ID NO 77
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 77
acaaaauaag aaagccaugt t                                                  21

<210> SEQ ID NO 78
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 78
cauggcuuuc uuauuuugut t                                                  21

<210> SEQ ID NO 79
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 79
aaggauuuag gccacugcct t                                                  21

<210> SEQ ID NO 80
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 80
ggcaguggcc uaaauccuut t                                                  21

<210> SEQ ID NO 81
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 81
uuugaaaaug uugaucucc                                                     19

<210> SEQ ID NO 82
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 82
uuugaaaaug uugaucucct t                                                  21

<210> SEQ ID NO 83
<211> LENGTH: 19
<212> TYPE: DNA
<213> ORGANISM: Artificial Sequence
<220> FEATURE:
<223> OTHER INFORMATION: Oligomeric Compound

```
<400> SEQUENCE: 83
ggagaucaac auuuucaaa                                              19

<210> SEQ ID NO 84
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 84
ggagaucaac auuuucaaat t                                           21

<210> SEQ ID NO 85
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 85
uuugaaaaug uugaucuccu                                             20

<210> SEQ ID NO 86
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 86
uuugaaaaug uugaucuccu u                                           21

<210> SEQ ID NO 87
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 87
aggagaucaa cauuuucaaa                                             20

<210> SEQ ID NO 88
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 88
aauuugaaaa uguugaucuc c                                           21

<210> SEQ ID NO 89
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 89
ucgcgggacc cguuggcag                                              19

<210> SEQ ID NO 90
```

```
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 90
cugccaacgg gucccgcga                                                    19

<210> SEQ ID NO 91
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 91
ggaccaccgc aucucuaca                                                    19

<210> SEQ ID NO 92
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 92
uguagagaug cggguggucc                                                   19

<210> SEQ ID NO 93
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 93
cuggcccuuc uuggagggc                                                    19

<210> SEQ ID NO 94
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 94
gcccuccaag aagggccag                                                    19

<210> SEQ ID NO 95
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 95
ggcuucaucc acugcccca                                                    19

<210> SEQ ID NO 96
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 96
```

-continued ugggggcagug gaugaagcc                                          19

<210> SEQ ID NO 97
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 97
cgagccagac uuggcccag                                           19

<210> SEQ ID NO 98
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 98
cugggccaag ucuggcucg                                           19

<210> SEQ ID NO 99
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 99
ggagcuggaa ggcugggag                                           19

<210> SEQ ID NO 100
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 100
cucccagccu uccagcucc                                           19

<210> SEQ ID NO 101
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 101
aaagcauucg uccgguugc                                           19

<210> SEQ ID NO 102
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 102
gcaaccggac gaaugcuuu                                           19

<210> SEQ ID NO 103
<211> LENGTH: 19
<212> TYPE: RNA

```
<213> ORGANISM: Artificial Sequence
<220> FEATURE:
<223> OTHER INFORMATION: Oligomeric Compound

<400> SEQUENCE: 103
cauaaaaagc auucguccg                                                   19

<210> SEQ ID NO 104
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 104
cggacgaaug cuuuuuaug                                                   19

<210> SEQ ID NO 105
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 105
gaauuaaccc uuggugaau                                                   19

<210> SEQ ID NO 106
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 106
auucaccaag gguuaauuc                                                   19

<210> SEQ ID NO 107
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 107
acuggacaga gaaagagcc                                                   19

<210> SEQ ID NO 108
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 108
ggcucuuucu cuguccagu                                                   19

<210> SEQ ID NO 109
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 109
gaaagagcca agaacaaaa                                                   19
```

<210> SEQ ID NO 110
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 110 uuuguucuu ggcucuuuc                                                     19

<210> SEQ ID NO 111
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 111
gagccaagaa caaaauugc                                                    19

<210> SEQ ID NO 112
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 112
gcaauuuugu ucuuggcuc                                                    19

<210> SEQ ID NO 113
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 113
uugcaaagga aaccaacaa                                                    19

<210> SEQ ID NO 114
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 114
uuguugguuu ccuuugcaa                                                    19

<210> SEQ ID NO 115
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 115
ccaacaauaa gaagaaaga                                                    19

<210> SEQ ID NO 116
<211> LENGTH: 19
<212> TYPE: RNA
<213> ORGANISM: Artificial Sequence
<220> FEATURE:

```
<223> OTHER INFORMATION: Oligomeric Compound

<400> SEQUENCE: 116 ucuucuucu uauuguugg                                                    19

<210> SEQ ID NO 117
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 117
gaagaaagaa uuugaggaa                                                   19

<210> SEQ ID NO 118
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 118
uuccucaaau ucuuucuuc                                                   19

<210> SEQ ID NO 119
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 119
cugcgaagaa agugcgccg                                                   19

<210> SEQ ID NO 120
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 120
cggcgcacuu ucuucgcag                                                   19

<210> SEQ ID NO 121
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 121
ggagaucaac auuuucaaa                                                   19

<210> SEQ ID NO 122
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 122
uuugaaaaug uugaucucc                                                   19
```

```
<210> SEQ ID NO 123
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 123
cugugcuccu guuugucu                                                   19

<210> SEQ ID NO 124
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 124
agacaaaaca ggagcacag                                                  19

<210> SEQ ID NO 125
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 125
guggcaccag aggugcuuc                                                  19

<210> SEQ ID NO 126
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 126
gaagcaccuc uggugccac                                                  19

<210> SEQ ID NO 127
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 127
gaaggcagug ucccuuuug                                                  19

<210> SEQ ID NO 128
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 128
caaaagggac acugccuuc                                                  19

<210> SEQ ID NO 129
<211> LENGTH: 19
<212> TYPE: RNA
<213> ORGANISM: Artificial Sequence
<220> FEATURE:
<223> OTHER INFORMATION: Oligomeric Compound
```

```
<400> SEQUENCE: 129
gaugcaugac uugugugug                                              19

<210> SEQ ID NO 130
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 130
cacacacaag ucaugcauc                                              19

<210> SEQ ID NO 131
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 131
uggagacaga gucccuggc                                              19

<210> SEQ ID NO 132
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 132
gccagggacu cugucucca                                              19

<210> SEQ ID NO 133
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 133
cauggcuuuc uuauuuugu                                              19

<210> SEQ ID NO 134
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 134
acaaaauaag aaagccaug                                              19

<210> SEQ ID NO 135
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 135
uuguuaauuc acagaauag                                              19

<210> SEQ ID NO 136
<211> LENGTH: 19
```

-continued

```
<212> TYPE: RNA
<213> ORGANISM: Artificial Sequence
<220> FEATURE:
<223> OTHER INFORMATION: Oligomeric Compound

<400> SEQUENCE: 136 cuauucgug aauuaacaa                                                19

<210> SEQ ID NO 137
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 137
cuacaauuaa aacuaagca                                               19

<210> SEQ ID NO 138
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 138
ugcuuaguuu uaauuguag                                               19

<210> SEQ ID NO 139
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 139
acuaagcaca aagccauuc                                               19

<210> SEQ ID NO 140
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 140
gaauggcuuu gugcuuagu                                               19

<210> SEQ ID NO 141
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 141
uagagugaua ggaagcguc                                               19

<210> SEQ ID NO 142
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 142
```
gacgcuuccu aucacucua         19

<210> SEQ ID NO 143
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 143
gcgucuggca gauacuccu         19

<210> SEQ ID NO 144
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 144
aggaguaucu gccagacgc         19

<210> SEQ ID NO 145
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 145
aaggcagugg ccuaaaucc         19

<210> SEQ ID NO 146
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 146
ggauuuaggc cacugccuu         19

<210> SEQ ID NO 147
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 147
ggcaguggcc uaaauccuu         19

<210> SEQ ID NO 148
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 148
aaggauuuag gccacugcc         19

<210> SEQ ID NO 149
<211> LENGTH: 19
<212> TYPE: RNA
<213> ORGANISM: Artificial Sequence

```
<220> FEATURE:
<223> OTHER INFORMATION: Oligomeric Compound

<400> SEQUENCE: 149
augacuuggc ucgaugcug                                                    19

<210> SEQ ID NO 150
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 150
cagcaucgag ccaagucau                                                    19

<210> SEQ ID NO 151
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 151
ccuucacauc ugucacguu                                                    19

<210> SEQ ID NO 152
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 152
aacgugacag augugaagg                                                    19

<210> SEQ ID NO 153
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 153
uucacagaau agcacaaac                                                    19

<210> SEQ ID NO 154
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 154
guuugugcua uucugugaa                                                    19

<210> SEQ ID NO 155
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 155
gccugcaccc cggagcgga                                                    19
```

```
<210> SEQ ID NO 156
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 156
uccgcuccgg ggugcaggc                                                    19

<210> SEQ ID NO 157
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 157
cauaaaaagc auucguccg                                                    19

<210> SEQ ID NO 158
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 158
cggacgaaug cuuuuuaug                                                    19

<210> SEQ ID NO 159
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 159
agcagcuggc ugccaugga                                                    19

<210> SEQ ID NO 160
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 160
uccauggcag ccagcugcu                                                    19

<210> SEQ ID NO 161
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 161
gcugcaccac uuccagggu                                                    19

<210> SEQ ID NO 162
<211> LENGTH: 19
<212> TYPE: RNA
<213> ORGANISM: Artificial Sequence
<220> FEATURE:
<223> OTHER INFORMATION: Oligomeric Compound
```

```
<400> SEQUENCE: 162
acccuggaag uggugcagc                                                19

<210> SEQ ID NO 163
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 163
uucccuggug ccaccagcc                                                19

<210> SEQ ID NO 164
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 164
ggcugguggc accagggaa                                                19

<210> SEQ ID NO 165
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 165
ugggccccuu agcaauguc                                                19

<210> SEQ ID NO 166
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 166
gacauugcua agggggccca                                               19

<210> SEQ ID NO 167
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 167
aggaaaggag aucaacauu                                                19

<210> SEQ ID NO 168
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 168
aauguugauc uccuuuccu                                                19

<210> SEQ ID NO 169
```

```
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 169
uuagauguuu caacugugc                                                    19

<210> SEQ ID NO 170
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 170
gcacaguuga aacaucuaa                                                    19

<210> SEQ ID NO 171
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 171
caguggcugc uucucucuc                                                    19

<210> SEQ ID NO 172
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 172
gagagagaag cagccacug                                                    19

<210> SEQ ID NO 173
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 173
cucauuuuug cuguuuuga                                                    19

<210> SEQ ID NO 174
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 174
ucaaaacagc aaaaaugag                                                    19

<210> SEQ ID NO 175
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 175
```

-continued uguucgcgug ggcagagcc                                                    19

<210> SEQ ID NO 176
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 176
ggcucugccc acgcgaaca                                                    19

<210> SEQ ID NO 177
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 177
ugugucugga ccucauguu                                                    19

<210> SEQ ID NO 178
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 178
aacaugaggu ccagacaca                                                    19

<210> SEQ ID NO 179
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 179
cacaguccug aguguggac                                                    19

<210> SEQ ID NO 180
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 180
guccacacuc aggacugug                                                    19

<210> SEQ ID NO 181
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 181
uggacuuggc aggugccug                                                    19

<210> SEQ ID NO 182
<211> LENGTH: 19
<212> TYPE: RNA

```
<213> ORGANISM: Artificial Sequence
<220> FEATURE:
<223> OTHER INFORMATION: Oligomeric Compound

<400> SEQUENCE: 182
caggcaccug ccaagucca                                            19

<210> SEQ ID NO 183
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 183
ucugagcugc agguuccuu                                            19

<210> SEQ ID NO 184
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 184
aaggaaccug cagcucaga                                            19

<210> SEQ ID NO 185
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 185
gugccuccuc agaggacag                                            19

<210> SEQ ID NO 186
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 186
cuguccucug aggaggcac                                            19

<210> SEQ ID NO 187
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 187
guuguugugu uuuuuuguu                                            19

<210> SEQ ID NO 188
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 188
aacaaaaaaa cacaacaac                                            19
```

```
<210> SEQ ID NO 189
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 189
acuaagcaca aagccauuc                                                      19

<210> SEQ ID NO 190
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 190
gaauggcuuu gugcuuagu                                                      19

<210> SEQ ID NO 191
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 191
gccauucuaa gucauuggg                                                      19

<210> SEQ ID NO 192
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 192
cccaaugacu uagaauggc                                                      19

<210> SEQ ID NO 193
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 193
gucauugggg aaacggggu                                                      19

<210> SEQ ID NO 194
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 194
accccguuuc cccaaugac                                                      19

<210> SEQ ID NO 195
<211> LENGTH: 19
<212> TYPE: RNA
<213> ORGANISM: Artificial Sequence
<220> FEATURE:
```

```
<223> OTHER INFORMATION: Oligomeric Compound

<400> SEQUENCE: 195
cggggugaac uucaggugg                                                   19

<210> SEQ ID NO 196
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 196
ccaccugaag uuccccg                                                     19

<210> SEQ ID NO 197
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 197 gccccccugcc uggcagccc                                                  19

<210> SEQ ID NO 198
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 198
gggcugccag gcaggggc                                                    19

<210> SEQ ID NO 199
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 199
guccgcccag gucccgcu                                                    19

<210> SEQ ID NO 200
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 200
agcggggacc ugggcggac                                                   19

<210> SEQ ID NO 201
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 201
gucuggcgua agaugaugg                                                   19
```

```
<210> SEQ ID NO 202
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 202
ccaucaucuu acgccagac                                                        19

<210> SEQ ID NO 203
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 203
gaugauggau uugauucgc                                                        19

<210> SEQ ID NO 204
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 204
gcgaaucaaa uccaucauc                                                        19

<210> SEQ ID NO 205
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 205
ccucuggagg ucaucucgg                                                        19

<210> SEQ ID NO 206
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 206
ccgagaugac cuccagagg                                                        19

<210> SEQ ID NO 207
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 207
auuugaaucg cgggacccg                                                        19

<210> SEQ ID NO 208
<211> LENGTH: 19
<212> TYPE: RNA
<213> ORGANISM: Artificial Sequence
<220> FEATURE:
<223> OTHER INFORMATION: Oligomeric Compound
```

```
<400> SEQUENCE: 208
cgggucccgc gauucaaau                                              19

<210> SEQ ID NO 209
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 209
cggcaugggu gccccgacg                                              19

<210> SEQ ID NO 210
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 210
cgucggggca cccaugccg                                              19

<210> SEQ ID NO 211
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 211
ggcccagugu uucuucugc                                              19

<210> SEQ ID NO 212
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 212
gcagaagaaa cacugggcc                                              19

<210> SEQ ID NO 213
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 213
ugcagcgggu gcugcuggu                                              19

<210> SEQ ID NO 214
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 214
accagcagca cccgcugca                                              19

<210> SEQ ID NO 215
<211> LENGTH: 19
```

```
<212> TYPE: RNA
<213> ORGANISM: Artificial Sequence
<220> FEATURE:
<223> OTHER INFORMATION: Oligomeric Compound

<400> SEQUENCE: 215
accaggugag aagugaggg                                                    19

<210> SEQ ID NO 216
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 216
cccucacuuc ucaccuggu                                                    19

<210> SEQ ID NO 217
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 217
uugccacugc ugugugauu                                                    19

<210> SEQ ID NO 218
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 218
aaucacacag caguggcaa                                                    19

<210> SEQ ID NO 219
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 219
cuggccgcuc cucccucag                                                    19

<210> SEQ ID NO 220
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 220
cugagggagg agcggccag                                                    19

<210> SEQ ID NO 221
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 221
```
cccagugagc cgcggggca                                          19

<210> SEQ ID NO 222
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 222
ugccccgcgg cucacuggg                                          19

<210> SEQ ID NO 223
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 223
gcugcaggcc gugugucug                                          19

<210> SEQ ID NO 224
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 224
cagacacacg gccugcagc                                          19

<210> SEQ ID NO 225
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 225
cauagagcug cagggugga                                          19

<210> SEQ ID NO 226
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 226
uccacccugc agcucuaug                                          19

<210> SEQ ID NO 227
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 227
auuguuacag cuucgcugg                                          19

<210> SEQ ID NO 228
<211> LENGTH: 19
<212> TYPE: RNA
<213> ORGANISM: Artificial Sequence

```
<220> FEATURE:
<223> OTHER INFORMATION: Oligomeric Compound

<400> SEQUENCE: 228
ccagcgaagc uguaacaau                                                        19

<210> SEQ ID NO 229
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 229
agaaauaaaa agccuguca                                                        19

<210> SEQ ID NO 230
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 230
ugacaggcuu uuuauuucu                                                        19

<210> SEQ ID NO 231
<211> LENGTH: 22
<212> TYPE: DNA
<213> ORGANISM: Artificial Sequence
<220> FEATURE:
<223> OTHER INFORMATION: PCR Primer

<400> SEQUENCE: 231
gcaccacttc cagggtttat tc                                                    22

<210> SEQ ID NO 232
<211> LENGTH: 26
<212> TYPE: DNA
<213> ORGANISM: Artificial Sequence
<220> FEATURE:
<223> OTHER INFORMATION: PCR Primer

<400> SEQUENCE: 232
tctcctttcc taagacattg ctaagg                                                26

<210> SEQ ID NO 233
<211> LENGTH: 22
<212> TYPE: DNA
<213> ORGANISM: Artificial Sequence
<220> FEATURE:
<223> OTHER INFORMATION: PCR Probe

<400> SEQUENCE: 233
tggtgccacc agccttcctg tg                                                    22
```